(12) United States Patent
Wilson et al.

(10) Patent No.: US 11,865,187 B2
(45) Date of Patent: *Jan. 9, 2024

(54) METHODS AND COMPOSITIONS FOR TREATING METASTATIC BREAST CANCER AND OTHER CANCERS IN THE BRAIN

(71) Applicant: The Trustees of the University of Pennsylvania, Philadelphia, PA (US)

(72) Inventors: James M. Wilson, Philadelphia, PA (US); William Thomas Rothwell, Philadelphia, PA (US); Christian Hinderer, New Orleans, LA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 509 days.

This patent is subject to a terminal disclaimer.

(21) Appl. No.: 16/986,946

(22) Filed: Aug. 6, 2020

(65) Prior Publication Data

US 2020/0368368 A1 Nov. 26, 2020

Related U.S. Application Data

(63) Continuation of application No. 15/306,413, filed as application No. PCT/US2015/027491 on Apr. 24, 2015, now Pat. No. 10,780,182.

(60) Provisional application No. 61/984,686, filed on Apr. 25, 2014.

(51) Int. Cl.
*A61K 48/00* (2006.01)
*C07K 16/32* (2006.01)
*A61K 9/00* (2006.01)

(52) U.S. Cl.
CPC .......... *A61K 48/005* (2013.01); *A61K 9/0085* (2013.01); *C07K 16/32* (2013.01); *C07K 2317/24* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,139,941 A | 8/1992 | Muzyczka et al. |
| 5,741,683 A | 4/1998 | Zhou et al. |
| 5,821,337 A | 10/1998 | Carter et al. |
| 6,054,297 A | 4/2000 | Carter et al. |
| 6,057,152 A | 5/2000 | Samulski et al. |
| 6,204,059 B1 | 3/2001 | Samulski et al. |
| 6,268,213 B1 | 7/2001 | Samulski et al. |
| 6,491,907 B1 | 12/2002 | Rabinowitz et al. |
| 6,596,535 B1 | 7/2003 | Carter et al. |
| 6,660,514 B1 | 12/2003 | Zolotukhin et al. |
| 6,951,753 B2 | 10/2005 | Shenk et al. |
| 7,094,604 B2 | 8/2006 | Snyder et al. |
| 7,125,717 B2 | 10/2006 | Carter et al. |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,456,683 B2 | 11/2008 | Takano et al. |
| 7,465,583 B2 | 12/2008 | Samulski et al. |
| 7,588,772 B2 | 9/2009 | Kay et al. |
| 7,601,335 B2 | 10/2009 | Mccutcheon et al. |
| 7,790,449 B2 | 9/2010 | Gao et al. |
| 7,906,111 B2 | 3/2011 | Wilson et al. |
| 8,187,601 B2 | 5/2012 | Weng et al. |
| 8,524,678 B2 | 9/2013 | Watkins et al. |
| 8,802,093 B2 | 8/2014 | Johnson et al. |
| 9,102,949 B2 | 8/2015 | Gao et al. |
| 2003/0086924 A1 | 5/2003 | Sliwkowski et al. |
| 2006/0018899 A1 | 1/2006 | Kao et al. |
| 2006/0136184 A1 | 6/2006 | Gustafsson et al. |
| 2008/0118501 A1 | 5/2008 | Schindler et al. |
| 2008/0138349 A1 | 6/2008 | Stavenhagen et al. |
| 2008/0241103 A1 | 10/2008 | Qian et al. |
| 2008/0269149 A1 | 10/2008 | Bowles et al. |
| 2010/0322931 A1 | 12/2010 | Harding et al. |
| 2010/0330076 A1 | 12/2010 | Georgiou et al. |
| 2011/0097323 A1 | 4/2011 | Johnson et al. |
| 2011/0236353 A1 | 9/2011 | Wilson et al. |
| 2012/0058102 A1* | 3/2012 | Wilson ............... A61P 19/04 424/94.6 |
| 2012/0177605 A1* | 7/2012 | Kaspar ............... A61K 48/005 435/320.1 |

(Continued)

FOREIGN PATENT DOCUMENTS

| | | |
|---|---|---|
| JP | 2013-531471 | 8/2013 |
| WO | WO-2003/042397 | 5/2003 |

(Continued)

OTHER PUBLICATIONS

Bendell et al, Central nervous system metastases in women who receive trastuzumab-based therapy for metastatic breast carcinoma. Cancer. Jun. 15, 2003;97(12):2972-7 (May 29 2003).

(Continued)

*Primary Examiner* — Allison M Fox
*Assistant Examiner* — Kimberly A Aron
(74) *Attorney, Agent, or Firm* — Howson & Howson; Cathy A. Kodroff

(57) ABSTRACT

A composition comprising at least one AAV vector formulated for central nervous system delivery is described. The composition comprises at least one expression cassette which contains sequences encoding an anti-neoplastic immunoglobulin construct for delivery to the brain operably linked to expression control sequences therefor and a pharmaceutically acceptable carrier. The anti-neoplastic immunoglobulin construct may be an immunoglobulin modified to have decreased or no measurable affinity for neonatal Fc receptor (FcRn). Also provided are methods of using these constructs in preparing pharmaceutical compositions and uses thereof in anti-neoplastic regimens, particularly for primary and/or metastatic cancers of the brain.

16 Claims, 2 Drawing Sheets

Specification includes a Sequence Listing.

(56) References Cited

U.S. PATENT DOCUMENTS

| | | | |
|---|---|---|---|
| 2013/0136729 A1 | 5/2013 | French et al. |
| 2013/0189225 A1 | 7/2013 | Voit et al. |
| 2013/0195801 A1 | 8/2013 | Gao et al. |
| 2013/0273650 A1 | 10/2013 | Wu et al. |
| 2013/0287736 A1 | 10/2013 | Passini et al. |
| 2014/0032186 A1 | 1/2014 | Gustafsson et al. |
| 2017/0008970 A1 | 1/2017 | Babcook et al. |

FOREIGN PATENT DOCUMENTS

| | | |
|---|---|---|
| WO | WO-2005/033321 | 4/2005 |
| WO | WO-2006/110689 | 10/2006 |
| WO | WO-2010/111367 A1 | 9/2010 |
| WO | WO-2010/119991 A3 | 10/2010 |
| WO | WO-2011/126808 | 10/2011 |
| WO | WO-2011/133890 A1 | 10/2011 |
| WO | WO-2011/143318 A2 | 11/2011 |
| WO | WO-2011/160119 A2 | 12/2011 |
| WO | WO-2012/020006 A2 | 2/2012 |
| WO | WO-2012/031198 A2 | 3/2012 |
| WO | WO-2012/125124 A1 | 9/2012 |
| WO | WO-2012/138975 A1 | 10/2012 |
| WO | WO-2013/037961 A1 | 3/2013 |
| WO | WO-2013/046704 A2 | 4/2013 |
| WO | WO-2013/049493 | 4/2013 |
| WO | WO-2013/076186 | 5/2013 |
| WO | WO-2013/155222 | 10/2013 |
| WO | WO-2013/190059 A1 | 12/2013 |
| WO | WO-2014/025813 A1 | 2/2014 |
| WO | WO-2014/043480 A1 | 3/2014 |
| WO | WO-2014/043480 A1 | 3/2014 |
| WO | WO-2015/012924 | 1/2015 |
| WO | WO-2015/164723 | 10/2015 |

OTHER PUBLICATIONS

Carter et al. "Humanization of an anti-p185HER2 antibody for human cancer therapy." Proceedings of the National Academy of Sciences 89.10 (1992): 4285-4289. (May 1992).

Cooper et al, Efflux of monoclonal antibodies from rat brain by neonatal Fc receptro, FCRN. Brain Res Oct. 9, 2013 vol. 1534 p. 13-21 (Epub Aug. 23, 2013).

Coprini et al, "A VSV-G pseudotyped last generation lentiviral vector mediates high level and persistent gene transfer in models of airway epithelium in vitro and in vivo." Viruses 2.8 (2010): 1577-1588. (Epub Aug. 2, 2010).

Deane et al, Clearance of amyloid-beta peptide across the blood-brain barrier: implication for therapies in Alxheimer's disease. CNS Neurol Disord Drug Targets Mar. 2009 vol. 8 No. 1 pp. 16-30.

Distefano et al, "The natural history of breast cancer patients with brain metastases." Cancer 44.5 (1979): 1913-1918. (Nov. 1979).

Edelman et al, "The covalent structure of an entire γG immunoglobulin. molecule." Proceedings of the National Academy of Sciences 63.1 (1969): 78-85. (May 1969).

Gahoual et al, "Rapid and multi-level characterization of trastuzumab using sheathless capillary electrophoresis-tandem mass spectrometry." MAbs. vol. 5. No. 3. Taylor & Francis, 2013. 479-90. (Epub Apr. 5, 2013).

Glamann et al. "Characterization of a macaque recombinant monoclonal antibody that binds to a CD4-induced epitope and neutralizes simian immunodeficiency virus." Journal of virology 74.15 (2000): 7158-7163. (Aug. 2000).

Glascock et al. "Delivery of therapeutic agents through intracerebroventricular (ICV) and intravenous (IV) injection in mice." JoVE (Journal of Visualized Experiments) 56 (2011): e2968-e2968.(Oct. 3, 2011).

Gray et al. "Global CNS gene delivery and evasion of anti-AAV-neutralizing antibodies by intrathecal AAV administration in non-human primates." Gene therapy 20.4 (2013): 450-459. (Epub Jan. 10, 2013).

Hachiya et al, "Gene transfer in human skin with different pseudotyped HIV-based vectors." Gene therapy 14.8 (2007): 648-656. (Epub Feb. 1, 2007).

Hall et al, Long-term survival with metastatic cancer to the brain. Med Oncol. Nov. 2000;17(4):279-86.

Jiang et al. "A novel peptide isolated from a phage display peptide library with trastuzumab can mimic antigen epitope of HER-2." Journal of Biological Chemistry 280.6 (2005): 4656-4662. Epub Nov. 9, 2004.

Kodack et al. "Combined targeting of 1-HER2 and VEGFR2 for effective treatment of HER2-amplified breast cancer brain metastases." Proceedings of the National Academy of Sciences 109.45 (2012): E3119-E3127. (Epub Oct. 15, 2012).

Kuo et al. "Neonatal Fc receptor and IgG-based therapeutics." MAbs. vol. 3. No. 5. Taylor & Francis, 2011. 422-430 (Epub Sep. 1, 2011).

Lazar et al, "Engineered antibody Fc variants with enhanced effector function." Proceedings of the National Academy of Sciences of the United States of America 103.11 (2006): 4005-4010. (Mar 14, 2006).

Lock et al, "Rapid, simple, and versatile manufacturing of recombinant adeno-associated viral vectors at scale." Human gene therapy 21.10 (2010): 1259-1271. (Published online Sep. 24, 2010).

Martinez-Aranda et al, Development of a Preclinical Therapeutic Model of Human Brain Metastasis with Chemoradiotherapy. Int J Mol Sci. 2013;14:8306-8327 (Published: Apr. 16, 2013).

McCarty et al, "Self-complementary recombinant adeno-associated virus (scAAV) vectors promote efficient transduction independently of DNA synthesis", Gene Therapy, Aug. 2001, vol. 8, No. 16, pp. 1248-1254 (Aug. 2001).

Moore, et al, "Engineered Fc variant antibodies with enhanced ability to recruit complement and mediate effector functions." MAbs. vol. 2. No. 2. Taylor & Francis, 2010. 181-189 (Mar. 2010).

Nakayama et al. "Antitumor activity of TAK-285, an investigational, non-Pgp substrate HER2/EGFR kinase inhibitor, in cultured tumor cells, mouse and rat xenograft tumors, and in an HER2-positive brain metastasis model." J Cancer 4.7 (2013): 557-65. (Published online Aug. 16, 2013).

Nanni et al. "Multiorgan metastasis of human HER-2+ breast cancer in Rag2—/—; Il2rg—/— mice and treatment with PI3K inhibitor." PLoS One 7.6 (2012): e39626. (Epub Jun. 21, 2012).

Natsume, et al, "Improving effector functions of antibodies for cancer treatment: Enhancing ADCC and CDC." Drug Des Devel Ther 3 (2009): 7-16. (pub online Sep. 21, 2009).

Nu et al, Brain metastases: the HER2 paradigm. Clin Cancer Res. Mar. 15, 2007;13(6):1648-55 (Published Mar. 15, 2007).

Palmieri et al, Her-2 overexpression increases the metastatic outgrowth of breast cancer cells in the brain. Cancer Res. May 1, 2007;67(9):4190-8 (May 1, 2007).

Park et al. "Ultrasound-mediated blood-brain/blood-tumor barrier disruption improves outcomes with trastuzumab in a breast cancer brain metastasis model." Journal of controlled release 163.3 (2012): 277-284.(Epub Sep. 18, 2012).

Pienkowski et al. Trastuzumab treatment in patients with breast cancer and metastatic CNS disease. Ann Oncol. May 2010; 21(5):917-24 (Aug. 28, 2009).

Shields et al,"High resolution mapping of the binding site on human IgG1 for FcγRI, FcγRII, FcγRIII, and FcRn and design of IgG1 variants with improved binding to the FcγR." Journal of Biological Chemistry 276.9 (2001): 6591-6604. (Epub Nov. 28, 2000).

Shojima et al. "Application of intrathecal trastuzumab for treatment of meningeal carcinomatosis in HER2-overexpressing metastatic breast cancer." Journal of Clinical Oncology 26.90150 (2008): 1138-1138. (May 1, 2006).

Lee-Hoeflich et al., A central role for HER3 in HER2-amplified breast cancer: implications for targeted therapy. Cancer Res. Jul. 15, 2008;68(14):5878-87. doi: 10.1158/0008-5472.CAN-8-0380. PubMed PMID: 18632642. (Published Jul. 15, 2008).

Stavenhagen et al, Fc optimization of therapeutic antibodies enhances their ability to kill tumor cells in vitro and controls tumor expansion in vivo via low-affinity activating Fcγ receptors. Cancer Research, 2007 67:8882-8890 (Published Sep. 15, 2007).

(56) References Cited

OTHER PUBLICATIONS

Thomson et al, Nucl. Acids. Res., "A comprehensive comparison of multiple sequence alignments", 27(13):2682-2690 (1999). (Jul. 1, 1999).
Zagouri et al, Intrathecal administration of trastuzumab for the treatment of meningeal carcinomatosis in HER2-positive metastatic breast cancer: a systematic review and pooled analysis. Breast Cancer Res Treat. May 2013;139(1):13-22 (Epub Apr. 16, 2013).
Zhang et al., 2009, "Adenovirus-adeno-associated virus hybrid for large-scale recombinant adeno-associated virus production," Human Gene Therapy 20:922-929 (Jul. 20, 2009).
Radcliffe et al, "Multiple gene products from a single vector:'self-cleaving'2A peptides." Gene Therapy 11.23 (2004): 1673-1673.
Cooper et al, "Efflux of monoclonal antibodies from rat brain by neonatal Fc receptor, FcRn." Brain Res. Oct. 9, 2013;1534:13-21. doi: 10.1016/j.brainres.2013.08.035. Epub Aug. 23, 2013.
Zagouri et al, "Intrathecal administration of trastuzumab for the treatment of meningeal carcinomatosis in HER2-positive metastatic breast cancer: a systematic review and pooled analysis." Breast Cancer Res Treat. May 2013;139(1):13-22. doi: 10.1007/s10549-013-2525-y. Epub Apr. 16, 2013.
Samaranch et al, "Adeno-associated virus serotype 9 transduction in the central nervous system of nonhuman primates." Hum Gene Ther. Apr. 2012;23(4):382-9. doi: 10.1089/hum.2011.200. Epub Mar. 28, 2012.
Wang et al, "Persistent expression of biologically active anti-HER2 antibody by AAVrh.10-mediated gene transfer." Cancer Gene Ther. Aug. 2010;17(8):559-70. doi: 10.1038/cgt.2010.11. Epub May 7, 2010.
Deane et al, "Clearance of amyloid-beta peptide across the blood-brain barrier: implication for therapies in Alzheimer's disease." CNS Neurol Disord Drug Targets. Mar. 2009;8(1):16-30. (Mar. 2009).
Ghetie et al, "Multiple roles for the major histocompatibility complex class I-related receptor FcRn." Annu Rev Immunol. 2000;18:739-66. (Apr. 2000).
Hinderer et al, "Widespread gene transfer in the central nervous system of cynomolgus macaques following delivery of AAV9 into the cisterna magna." Mol Ther Methods Clin Dev. Dec. 10, 2014;1:14051. doi: 10.1038/mtm.2014.51. eCollection 2014. (Dec. 2014).
Kurihara, Tenbo (Review), Isotope News, vol. 703:8-12, Nov. 2012.
Matumot et al., Search for new biomarkers for predicting therapeutic effects in patients receiving trastuzumab, Kinkidai I Shi (Medical Journal of Kinki University), vol. 34(3):13A, Mar. 2009.
Okawa et al., Molecular targeted drug treatment in breast cancer, Satsu Byo Shi (The Journal of Sapporo City General Hospital), vol. 72(1):29-33, Oct. 2012.
Borvak J et al. Functional expression of the MHC class I-related receptor, FcRn, In endothelial cells of mice. Int Immunol. Sep. 1998;10(9):1289-98. Published: Sep. 1, 1998.
Bousquet G, et al. Intrathecal Trastuzumab Halts Progression of CNS Metastases in Breast Cancer. J Clin Oncol. Jun. 1, 2016;34(16):e151-5. doi: 10.1200/JCO.2012.44.8894. Epub Dec. 29, 2014.
Carter P, et al. Humanization of an anti-p185HER2 antibody for human cancer therapy. Proc Natl Acad Sci U S A. May 15, 1992;89(10):4285-9. (Published online May 15, 1992.).
Cearley CN et al. Transduction characteristics of adeno-associated virus vectors expressing cap serotypes 7, 8, 9, and Rh10 in the mouse brain. Mol Ther. Mar. 2006;13(3):528-37. Epub Jan. 18, 2006.
Colozza M et al, Extended survival of a HER-2-positive metastatic breast cancer patient with brain metastases also treated with intrathecal trastuzumab. Cancer Chemother Pharmacol. May 2009;63(6):1157-9. doi: 10.1007/s00280-008-0859-7. Epub Nov. 6, 2008.
Deane R, et al. IgG-assisted age-dependent clearance of Alzheimer's amyloid beta peptide by the blood-brain barrier neonatal Fc receptor. J Neurosci. Dec. 14, 2005;25(50):11495-503. (Dec. 14, 2005.).
Delano WL, et al. Convergent solutions to binding at a protein-protein interface. Science. Feb. 18, 2000;287(5456):1279-83. Feb. 2000.
Distefano A, et al. The natural history of breast cancer patients with brain metastases. Cancer. Nov. 1979;44(5):1913-8. (Nov. 1979).
FDA approval brings first gene therapy to the United States—CAR T-cell therapy approved to treat certain children and young adults with B-cell acute lymphoblastic leukemia, released Aug. 30, 2017, https://www.fda.gov/NewsEvents/Newsroom/PressAnnouncements/ucm574058.htm.
FDA approves CAR-T cell therapy to treat adults with certain types of large B-cell lymphoma—Yescarta is the second gene therapy product approved in the U.S. released Oct. 18, 2017. https://www.fda.gov/NewsEvents/Newsroom/PressAnnouncements/ucm581216.htm.
Gahoual R, et al. Rapid and multi-level characterization of trastuzumab using sheathless capillary electrophoresis-tandem mass spectrometry. MAbs. May-Jun. 2013;5(3):479-90. doi: 10.4161/mabs.23995. (Epub Apr. 5, 2013).
Ghetie V et al. FcRn: the MHC class I-related receptor that is more than an IgG transporter. Immunol Today. Dec. 1997;18(12):592-8. (Dec. 1997).
Gradishar WJ. Emerging approaches for treating HER2-positive metastatic breast cancer beyond trastuzumab. Annals of Oncology, vol. 24, Issue 10, Oct. 1, 2013, pp. 2492-2500, Published: Jul. 4, 2013.
Hall WA et al. Long-term survival with metastatic cancer to the brain. Med Oncol. Nov. 2000;17(4):279-86. (Nov. 2000).
Herceptin® (trastuzumab), Highlights of prescribing information, Product Label, 32 pages, revised Nov. 2013.
Hinderer, C. (2015). Intrathecal adeno-associated virus vector delivery for mucopolysaccharidosis type I (Order No. 10003677). Available from ProQuest Dissertations & Theses Global. (1761165511). Hum Gene Ther Methods. Apr. 2015;26(2):43-4. doi: 10.1089/hgtb.2015.041. (Mar. 24, 2015).
Johnson PR et al, Vector-mediated gene transfer engenders long-lived neutralizing activity and protection against SIV infection in monkeys. Nat Med. Aug. 2009;15(8):901-6. doi: 10.1038/nm.1967. Epub May 17, 2009.
Kadcyla™ (ado-trastuzumab emtansine), Product Label and Important Drug Information, 5 pages, revised Aug. 2013.
Kodack DP, et al. Combined targeting of HER2 and VEGFR2 for effective treatment of HER2-amplified breast cancer brain metastases. Proc Natl Acad Sci U S A. Nov. 6, 2012;109(45):E3119-27. doi: 10.1073/pnas.1216078109. Epub Oct. 15, 2012.
Kristoffersen E. K. FcRn and IgG in human choroid plexus. Scand. J. Immunol. 45, p. 447, abstract # 78, in Abstracts of Papers Presented First published: Apr. 1997.
Limberis MP, et al. Intranasal antibody gene transfer in mice and ferrets elicits broad protection against pandemic influenza. Sci Transl Med. May 29, 2013;5(187):187ra72. doi: 10.1126/scitranslmed.3006299. (May 2013).
Lin NU, et al. Brain metastases: the HER2 paradigm. Clin Cancer Res. Mar. 15, 2007;13(6):1648-55. (Published Mar. 2007).
Lun MP, et al. Development and functions of the choroid plexus-cerebrospinal fluid system. Nat Rev Neurosci. Aug. 2015;16(8):445-57. doi: 10.1038/nrn3921. Epub Jul. 15, 2015.
Lutterotti A et al, Getting specific: monoclonal antibodies in multiple sclerosis. Lancet Neurol. Jun. 2008;7(6):538-47. doi: 10.1016/S1474-4422(08)70110-8. (May 2008).
Martin WL et al. Crystal structure at 2.8 A of an FcRn/heterodimeric Fc complex: mechanism of pH-dependent binding. Mol Cell. Apr. 2001;7(4):867-77. (Apr. 2001).
Martínez-Aranda A, et al. Development of a preclinical therapeutic model of human brain metastasis with chemoradiotherapy. Int J Mol Sci. Apr. 16, 2013;14(4):8306-27. doi: 10.3390/ijms14048306. (Published: Apr. 16, 2013).
McCarthy KM et al. Bidirectional transcytosis of IgG by the rat neonatal Fc receptor expressed in a rat kidney cell line: a system to study protein transport across epithelia. J Cell Sci. Apr. 2000;113 (Pt 7):1277-85. (Published online Apr. 1, 2000.).

(56) References Cited

OTHER PUBLICATIONS

Medesan C et al. Delineation of the amino acid residues involved in transcytosis and catabolism of mouse IgG1. J Immunol. Mar. 1, 1997;158(5):2211-7. (Published online Mar. 1, 1997.).

Mehta et al. Therapeutic approaches for HER2-positive brain metastases: circumventing the blood-brain barrier. Cancer Treat Rev. May 2013;39(3):261-9. doi: 10.1016/j.ctrv.2012.05.006. Epub Jun. 22, 2012.

Melnick JL, et al. Association of 20-Millimicron Particles with Adenoviruses. J Bacteriol. Jul. 1965;90(1):271-4. (Jul. 1965).

Nakayama A et al. Antitumor Activity of TAK-285, an Investigational, Non-Pgp Substrate HER2/EGFR Kinase Inhibitor, in Cultured Tumor Cells, Mouse and Rat Xenograft Tumors, and in an HER2-Positive Brain Metastasis Model. J Cancer. Aug. 16, 2013;4(7):557-65. doi: 10.7150/jca.6689. eCollection 2013. (Published Aug. 16, 2013).

Ogivri (trastuzumab-dkst), Highlights of prescribing information, Product Label, 39 pages, revised Dec. 2017.

Palmieri D, et al. Her-2 overexpression increases the metastatic outgrowth of breast cancer cells in the brain. Cancer Res. May 1, 2007;67(9):4190-8. (Published first May 4, 2007.)

Park EJ, et al. Ultrasound-mediated blood-brain/blood-tumor barrier disruption improves outcomes with trastuzumab in a breast cancer brain metastasis model. J Control Release. Nov. 10, 2012;163(3):277-84. doi: 10.1016/j.jconrel.2012.09.007. Epub Sep. 18, 2012.

Perjeta® (pertuzumab), Highlights of prescribing information, Product Label, 24 pages, revised Sep. 2013.

Petkova SB, et al. Enhanced half-life of genetically engineered human IgG1 antibodies in a humanized FcRn mouse model: potential application in humorally mediated autoimmune disease. Int Immunol. Dec. 2006;18(12):1759-69. Epub Oct. 31, 2006.

Philippidis A, FDA Advisory Panel Unanimously Recommends Approval of Spark Therapeutics' Gene Therapy Luxturna, GEN News Highlights, Oct 2017. https://www.genengnews.com/gen-news-highlights/fda-advisory-panel-unanimously-recommends-approval-of-spark-therapeutics-gene-therapy-luxturna/81255043.

Pieńkowski T et al. Trastuzumab treatment in patients with breast cancer and metastatic CNS disease. Ann Oncol. May 2010;21(5):917-24. doi: 10.1093/annonc/mdp353. Epub Aug. 28, 2009.

Popov S et al. The stoichiometry and affinity of the interaction of murine Fc fragments with the MHC class I-related receptor, FcRn. Mol Immunol. Apr. 1996;33(6):521-30. (Apr. 1996).

Roopenian DC, et al. FcRn: the neonatal Fc receptor comes of age. Nat Rev Immunol. Sep. 2007;7(9):715-25. Epub Aug. 17, 2007.

Rubenstein JL et al. Phase I study of intraventricular administration of rituximab in patients with recurrent CNS and intraocular lymphoma. J Clin Oncol. Apr. 10, 2007;25(11):1350-6. Epub Feb. 20, 2007.

Schlachetzki F et al. Expression of the neonatal Fc receptor (FcRn) at the blood-brain barrier. J Neurochem. Apr. 2002;81(1):203-6. (First published: Mar. 25, 2002).

Shields RL et al. High resolution mapping of the binding site on human IgG1 for Fc gamma RI, Fc gamma RII, Fc gamma RIII, and FcRn and design of IgG1 variants with improved binding to the Fc gamma R. J Biol Chem. Mar. 2, 2001;276(9):6591-604. (First Published on Nov. 28, 2000).

Spector NL and Blackwell KL. Understanding the mechanisms behind trastuzumab therapy for human epidermal growth factor receptor 2-positive breast cancer. J Clin Oncol. Dec. 1, 2009;27(34):5838-47. doi: 10.1200/JCO.2009.22.1507. Epub Nov. 2, 2009.

Kabat EA, et al. Sequences of proteins of immunological interest. Bethesda, MD : U.S. Dept. of Health and Human Services, Public Health Service, National Institutes of Health, 1991.

Sperduto et al. Summary report on the graded prognostic assessment: an accurate and facile diagnosis-specific tool to estimate survival for patients with brain metastases. J Clin Oncol. Feb. 1, 2012;30(4):419-25. doi: 10.1200/JCO.2011.38.0527. Epub Dec. 27, 2011.

Telleman P et al. The role of the Brambell receptor (FcRB) in liver: protection of endocytosed immunoglobulin G (IgG) from catabolism in hepatocytes rather than transport of IgG to bile. Immunology. Jun. 2000;100(2):245-51. First published: Jun. 2000.

Zhang Y, et al. Mediated efflux of IgG molecules from brain to blood across the blood-brain barrier. J Neuroimmunol. Mar. 1, 2001;114(1-2):168-72. (Available online Feb. 28, 2001.).

Eigenbrot C, et al. X-ray structures of the antigen-binding domains from three variants of humanized anti-p185HER2 antibody 4D5 and comparison with molecular modeling. J Mol Biol. Feb. 20, 1993;229(4):969-95. (Feb. 1993).

"Adjuvant Breast Cancer Treatment," Web page <http://www.herceptin.com/breast/adjuvant>, 6 page, Mar. 1, 2014, retrieved from Internet Archive Wayback Machine <hhttps://web.archive.org/web/20140301014849/http://www.herceptin.com/breast/adjuvant> on Feb. 5, 2018).

Bell P, et al. Motor neuron transduction after intracisternal delivery of AAV9 in a cynomolgus macaque. Hum Gene Ther Methods. Apr. 2015;26(2):43-4. doi: 10.1089/hgtb.2015.041. (Mar. 24, 2015).

Medicines in Development Biologics, 2013 Report, pp. 1-87, a publication of PhRMA's Communications & Public Affairs Department. (202) 835-3460 (Apr. 8, 2013).

Masat E, et al. Humoral immunity to AAV vectors in gene therapy: challenges and potential solutions. Discov Med. Jun. 2013;15(85):379-89. Published on Jun. 27, 2013.

Pegram M, et al. Biological rationale for HER2/neu (c-erbB2) as a target for monoclonal antibody therapy. Semin Oncol. Oct. 2000;27(5 Suppl 9):13-9.

Rothwell, William Thomas. Intrathecal AAV9.Trastuzumab Tumor Prophylaxis and Treatment in a Murine Xenograft Model of HER2+0 Breast Cancer Brain Metastases. Dissertation/thesis number/Order No. 10642010. Available from ProQuest Dissertations & Theses Global. ProQuest document ID: 2010480763. Publication year 2017. Retrieved from https://www.proquest.com/products-services/dissertations/ on Jun. 21, 2018.

Rothwell, et al. 274. Intrathecal AAV9.trastuzumab for Prophylaxis and Treatment of HER2+ Breast Cancer Brain Metastases. Molecular Therapy vol. 25 No. 5S1, p. 129, Abstract 274. May 2017.

Trastuzumab, International Nonproprietary Names for Pharmaceutical Substances (INN), WHO Drug Information vol. 12, No. 2, 1998. Recommended INN: List 40, p. 203.

Trastuzumab emtansine, International Nonproprietary Names for Pharmaceutical Substances (INN), WHO Drug Information vol. 24, No. 2, 2010. Proposed INN: List 103, p. 172-173.

Trastuzumab duocarmazine, International Nonproprietary Names for Pharmaceutical Substances (INN), WHO Drug Information, vol. 30, No. 2, 2016. Proposed INN: List 115, p. 324-325.

Trastuzumab deruxtecan, International Nonproprietary Names for Pharmaceutical Substances (INN), WHO Drug Information vol. 30, No. 4, 2016. Proposed INN: List 116, p. 680-682.

Trastuzumab beta, International Nonproprietary Names for Pharmaceutical Substances (INN), WHO Drug Information vol. 31, No. 4, 2017. Proposed INN: List 118, p. 721-722.

Biotechnology Breakthrough in Breast Cancer Wins FDA Approval,— New Therapy for a Quarter of Women with Metastatic Breast Cancer; Testing for Protein Overexpression Critical. Retrieved from <https://www.gene.com/media/press-releases/4763/1998-09-25/biotechnology-breakthrough-in-breast-can> Sep. 1998: South San Francisco, California.

FDA Approves Herceptin for the Adjuvant Treatment of HER2-Positive Node-Positive Breast Cancer. Retrieved from <https://www.gene.com/media/press-releases/10207/2006-11-16/fda-approves-herceptin-for-the-adjuvant-> Nov. 16, 2006. South San Francisco, California.

Common Cancer Types, webpage <https://www.cancer.gov/types/common-cancers>, Jul. 21, 2017, 2 pages, retrieved from Internet Archive Wayback Machine <https://web.archive.org/web/20170721184555/https://www.cancer.gov/types/common-cancers>.

Kymriah (tisagenlecleucel) Prescribing information, N.P. Corporation, Editor.: East Hanover, New Jersey, USA. Revised Aug. 2017.

FDA Advisory Committee Unanimously Recommends Approval of Investigational Luxturna™ (voretigene neparvovec) for Patients with Biallelic RPE65-mediated Inherited Retinal Disease, in Inves-

(56) References Cited

OTHER PUBLICATIONS tigational Luxturna has the potential to be both the first pharmacologic treatment for an inherited retinal disease (IRD) and the first gene therapy for a genetic disease in the United States. 2017, Globe Newswire: Philadelphia. retrieved from https://globenewswire.com/news-release/2017/10/12/1145222/0/en/FDA-Advisory-Committee-Unanimously-Recommends-Approval-of-Investigational-LUXTURNA-voretigene-neparvovec-for-Patients-with-Biallelic-RPE65-mediated-Inherited-Retinal-Disease.html on Jul. 25, 2018. 6 pages. Oct. 12, 2017.

Kaal, E.C. and C.J. Vecht, CNS complications of breast cancer: current and emerging treatment options. CNS Drugs, 2007. 21(7): p. 559-79.

McKeage, K. and C.M. Perry, Trastuzumab: a review of its use in the treatment of metastatic breast cancer overexpressing HER2. Drugs, 2002. 62(1): p. 209-43.

Sendur, M.A.N.,et al, Cardiotoxicity of novel HER2-targeted therapies. Current Medical Research and Opinion, 2013. 29(8): p. 1015-1024. Epub Jun. 7, 2013.

Sandberg, D.I., et al., Ommaya reservoirs for the treatment of leptomeningeal metastases. Neurosurgery, 2000. 47(1): p. 49-54; discussion 54-5. Jul. 2000.

Abuqayyas, L. and J.P. Balthasar, Investigation of the role of FcgammaR and FcRn in mAb distribution to the brain. Mol Pharm, 2013. 10(5): p. 1505-13. Epub Jul. 2012.

Adler, M.D., A.E. Comi, and A.R. Walker, Acute hemorrhagic complication of diagnostic lumbar puncture. Pediatr Emerg Care, 2001. 17(3): p. 184-8. Jun. 2001.

Alstadhaug, K.B., et al., Post-lumbar puncture headache. Tidsskr Nor Laegeforen, 2012. 132(7): p. 818-21. Apr. 2012.

Arendt, K., et al., Atraumatic lumbar puncture needles: after all these years, are we still missing the point? Neurologist, 2009. 15(1): p. 17-20. Publication Date: Jan. 1, 2009.

Arnould, L., et al., Trastuzumab-based treatment of HER2-positive breast cancer: An antibody-dependent cellular cytotoxicity mechanism? Br J Cancer, 2006. 94(2): p. 259-67. Published: Jan. 10, 2006.

Asanuma, H., et al., Survivin expression is regulated by coexpression of human epidermal growth factor receptor 2 and epidermal growth factor receptor via phosphatidylinositol 3-kinase/AKT signaling pathway in breast cancer cells. Cancer Res, 2005. 65(23): p. 11018-25. Dec. 2005.

Azambuja, E.D., et al., Trastuzumab-Associated Cardiac Events at 8 Years of Median Follow-Up in the Herceptin Adjuvant Trial (BIG 1-01). Journal of Clinical Oncology, 2014. 32(20): p. 2159-2165. Epub Jun. 9, 2014.

Bachelot, T., et al., Lapatinib plus capecitabine in patients with previously untreated brain metastases from HER2-positive metastatic breast cancer (LANDSCAPE): a singlegroup phase 2 study. The Lancet Oncology, 2013. 14(1): p. 64-71. Epub Nov. 2, 2012.

Bacus, S.S., et al., AKT2 is frequently upregulated in HER-2/neu-positive breast cancers and may contribute to tumor aggressiveness by enhancing cell survival. Oncogene, 2002. 21(22): p. 3532-40. Published: May 15, 2002.

Baer, E.T., Post-dural puncture bacterial meningitis. Anesthesiology, 2006. 105(2): p. 381-93. Aug. 2006.

Balazs, A.B., et al., Antibody-based protection against HIV infection by vectored immunoprophylaxis. Nature, 2011. 481(7379): p. 81-4. Published: Nov. 30, 2011.

Bantel-Schaal, U., B. Hub, and J. Kartenbeck, Endocytosis of adeno-associated virus type 5 leads to accumulation of virus particles in the Golgi compartment. J Virol, 2002. 76(5): p. 2340-9. Mar. 2002.

Barnholtz-Sloan, J.S., et al., Incidence proportions of brain metastases in patients diagnosed (1973 to 2001) in the Metropolitan Detroit Cancer Surveillance. System. J Clin Oncol, 2004. 22(14): p. 2865-72. Jul. 2004.

Bartel, M., D. Schaffer, and H. Buning, Enhancing the Clinical Potential of AAV Vectors by Capsid Engineering to Evade Pre-Existing Immunity. Front Microbiol, 2011. 2: p. 204. Oct. 4, 2011.

Bartlett, J.S., R. Wilcher, and R.J. Samulski, Infectious entry pathway of adeno-associated virus and adeno-associated virus vectors. J Virol, 2000. 74(6): p. 2777-85. Mar. 2000.

Bartolotti, M., E. Franceschi, and A.A. Brandes, Treatment of brain metastases from HER-2-positive breast cancer: current status and new concepts. Future Oncol, 2013. 9(11): p. 1653-64. Published Online:Oct. 24, 2013.

Baselga, J., Clinical trials of Herceptin® (trastuzumab). Eur J Cancer, 2001. 37 Suppl 1: p. S18-24. Jan. 2001.

Baselga, J., Phase I and II clinical trials of trastuzumab. Ann Oncol, 2001. 12 Suppl 1: p. S49-55. Published: Mar. 1, 2001.

Basurto Ona, X., D. Osorio, and X. Bonfill Cosp, Drug therapy for treating post-dural puncture headache. Cochrane Database of Systematic Reviews, Jul. 15, 2015;(7):CD007887. doi: 10.1002/14651858. CD007887.pub3. First published: Jul. 15, 2015.

Bell, C.L., et al., The AAV9 receptor and its modification to improve in vivo lung gene transfer in mice. J. Clin. Invest., 2011. 121(6): p. 2427-35. Epub May 16, 2011.

Bell, P., et al., Analysis of tumors arising in male B6C3F1 mice with and without AAV vector delivery to liver. Mol Ther, 2006. 14(1): p. 34-44. Epub May 6, 2006.

Bergman, I., et al., Pharmacokinetics of IgG and IgM anti-ganglioside antibodies in rats and monkeys after intrathecal administration. J Pharmacol Exp Ther, 1998. 284(1): p. 111-5. Jan. 1998.

Berns, K.I. and R.M. Linden, The cryptic life style of adeno-associated virus. Bioessays, 1995. 17(3): p. 237-45. Mar. 1995.

Bevan, A.K., et al., Systemic gene delivery in large species for targeting spinal cord, brain, and peripheral tissues for pediatric disorders. Mol Ther, 2011. 19(11): p. 1971-80. Epub Aug. 2, 2011.

Bezov, D., R.B. Lipton, and S. Ashina, Post-dural puncture headache: part I diagnosis, epidemiology, etiology, and pathophysiology. Headache, 2010. 50(7): p. 1144-52. Epub Jun. 2010.

Bleyer, W.A., et al., The Ommaya reservoir: newly recognized complications and recommendations for insertion and use. Cancer, 1978. 41(6): p. 2431-7. Jun. 1978.

Boutin, S., et al., Prevalence of serum IgG and neutralizing factors against adenoassociated virus (AAV) types 1, 2, 5, 6, 8, and 9 in the healthy population: implications for gene therapy using AAV vectors. Hum Gene Ther, 2010. 21(6): p. 704-12. Published Online:Apr. 28, 2010.

Braen, A.P., et al., A 4-week intrathecal toxicity and pharmacokinetic study with trastuzumab in cynomolgus monkeys. Int J Toxicol, 2010. 29(3): p. 259-67. First Published May 6, 2010.

Brandt, D.S., Intrathecal trastuzumab: 46 months and no progression. Community Oncology, 2012. 9: p. 3. Publish date: Jul. 1, 2012.

Brinker, T., et al., A new look at cerebrospinal fluid circulation. Fluids Barriers CNS, 2014. 11: p. 10. Published: May 1, 2014.

Brufsky, A.M., et al., Central nervous system metastases in patients with HER2-positive metastatic breast cancer: incidence, treatment, and survival in patients from registHER. Clin Cancer Res, 2011. 17(14): p. 4834-43. Published first Jul. 17, 2011.

Bruhns, P., Properties of mouse and human IgG receptors and their contribution to disease models. Blood, 2012. 119(24): p. 5640-9. Epub Apr. 25, 2012.

Bryant, L.M., et al., Lessons learned from the clinical development and market authorization of Glybera. Hum Gene Ther Clin Dev, 2013. 24(2): p. 55-64. Published Online:May 13, 2013.

Calcedo, R. and J.M. Wilson, Humoral Immune Response to AAV. Front Immunol, 2013. 4: p. 341. Oct. 18, 2013.

Calcedo, R., et al., Worldwide epidemiology of neutralizing antibodies to adenoassociated viruses. J Infect Dis, 2009. 199(3): p. 381-90. Published: Feb. 1, 2009.

Calias, P., et al., Intrathecal delivery of protein therapeutics to the brain: a critical reassessment. Pharmacol Ther, 2014. 144(2): p. 114-22. Epub May 20, 2014.

Camann, W.R., et al., Effects of oral caffeine on postdural puncture headache. A doubleblind, placebo-controlled trial. Anesth Analg, 1990. 70(2): p. 181-4. Feb. 1990.

GlobeNewswire, Cascadian Therapeutics' Lead Candidate, Tucatinib, Receives Orphan Drug Designation from FDA for Treatment of Breast Cancer Patients with Brain Metastases. Retrieved from <https://globenewswire.com/news-release/2017/06/08/1010332/0/en/Cascadian-Therapeutics-Lead-Candidate-Tucatinib-Receives-

(56) References Cited

OTHER PUBLICATIONS

Orphan-Drug-Designation-from-FDA-for-Treatment-of-Breast-Cancer-Patients-with-Brain-Metastases.html>. 2 pages. Jun. 8, 2017.
Castle, M.J., et al., Long-distance axonal transport of AAV9 is driven by dynein and kinesin-2 and is trafficked in a highly motile Rab7-positive compartment. Mol Ther, 2014. 22(3): p. 554-66. Epub Oct. 8, 2013.
Chapman, P.H., E.R. Cosman, and M.A. Arnold, The relationship between ventricular fluid pressure and body position in normal subjects and subjects with shunts: a telemetric study. Neurosurgery, 1990. 26(2): p. 181-9. Feb. 1990.
Chng, J., et al., Cleavage efficient 2A peptides for high level monoclonal antibody expression in CHO cells. mAbs, 2015. 7(2): p. 403-412. Published online: Jan. 26, 2015.
Clayton, A.J., et al., Incidence of cerebral metastases in patients treated with trastuzumab for metastatic breast cancer. Br J Cancer, 2004. 91(4):639-43. Published: Jul. 20, 2004.
Clynes, R.A., et al., Inhibitory Fc receptors modulate in vivo cytotoxicity against tumor targets. Nat Med, 2000. 6(4): p. 443-6. Published: Apr. 1, 2000.
Coiffier, B., et al., CHOP chemotherapy plus rituximab compared with CHOP alone in elderly patients with diffuse large-B-cell lymphoma. N Engl J Med, 2002. 346(4): p. 235-42. Jan. 24, 2002.
Coiffier, B., Rituximab in combination with CHOP improves survival in elderly patients with aggressive non-Hodgkin's lymphoma. Semin Oncol, 2002. 29(2 Suppl 6): p. 18-22. Apr. 2002.
Conroy, P.H., et al., Real-time ultrasound-guided spinal anaesthesia: a prospective observational study of a new approach. Anesthesiol Res Pract, 2013. 2013: p. 525818. Epub Jan. 10, 2013.
Cote, G.M., D.B. Sawyer, and B.A. Chabner, ERBB2 inhibition and heart failure. N Engl J Med, 2012. 367(22): p. 2150-3. Nov. 29, 2012.
Crock, C., et al., Headache after lumbar puncture: randomised crossover trial of 22-gauge versus 25-gauge needles. Arch Dis Child, 2014. 99(3): p. 203-7. Epub 2013.
Crone, S.A. and K.F. Lee, Gene targeting reveals multiple essential functions of The neuregulin signaling system during development of the neuroendocrine and nervous systems. Ann N Y Acad Sci, 2002. 971: p. 547-53. Oct. 2002.
Dawood, S., et al., Prognosis of Women With Metastatic Breast Cancer by HER2 Status and Trastuzumab Treatment: An Institutional-Based Review. Journal of Clinical Oncology, 2010. 28(1): p. 92-98. Epub Nov. 23, 2009.
Dayton, R.D., D.B. Wang, and R.L. Klein, The advent of AAV9 expands applications for brain and spinal cord gene delivery. Expert Opin Biol Ther, 2012. 12(6): p. 757-66. Epub Apr. 20, 2012.
De Azambuja, E., et al., Trastuzumab-associated cardiac events at 8 years of median follow-up in the Herceptin Adjuvant trial (BIG 1-01). J Clin Oncol, 2014. 32(20): p. 2159-65. Epub Jun. 9, 2014.
De Keulenaer, G.W., K. Doggen, and K. Lemmens, The Vulnerability of the Heart As a Pluricellular Paracrine Organ. Lessons From Unexpected Triggers of Heart Failure in Targeted ErbB2 Anticancer Therapy, 2010. 106(1): p. 35-46. 2010.
Deangelis, L.M., Current diagnosis and treatment of leptomeningeal metastasis. J Neurooncol, 1998. 38(2-3): p. 245-52. Jun.-Jul. 1998.
Dieras, V. and T. Bachelot, The success story of trastuzumab emtansine, a targeted therapy in HER2-positive breast cancer. Target Oncol, 2014. 9(2): p. 111-22. Epub Jul. 14, 2013.
Ding, W., et al., rAAV2 traffics through both the late and the recycling endosomes in a dose-dependent fashion. Mol Ther, 2006. 13(4): p. 671-82. Epub Jan. 25, 2006.
Dodge, P.R. and M.N. Swartz Bacterial Meningitis—a Review of Selected Aspects. New England Journal of Medicine, 1965. 272(19): p. 1003-1010. May 1965.
Dumitrescu, C. and D. Lossignol, Intrathecal Trastuzumab Treatment of the Neoplastic Meningitis due to Breast Cancer: A Case Report and Review of the Literature. Case Rep Oncol Med, 2013. 2013: p. 154674. Epub Jan. 28, 2013.
Eiermann, W. and G. International Herceptin Study, Trastuzumab combined with chemotherapy for the treatment of HER2-positive metastatic breast cancer: pivotal trial data. Ann Oncol, 2001. 12 Suppl 1: p. S57-62. Published: Mar. 1, 2001.
Eric Althoff and Fiona Phillips, Novartis receives first ever FDA approval for a CAR-T cell therapy, Kymriah(TM) (CTL019), for children and young adults with B-cell ALL that is refractory or has relapsed at least twice. retrieved from <https://www.novartis.com/news/media-releases/novartis-receives-first-ever-fda-approval-car-t-cell-therapy-kymriahtm-ctl019> Apr. 2017, Novartis Corporate Media Relations Basel. 10 pages.
Eskey, C.J. and C.S. Ogilvy, Fluoroscopy-guided lumbar puncture: decreased frequency of traumatic tap and implications for the assessment of CT-negative acute subarachnoid hemorrhage. AJNR Am J Neuroradiol, 2001. 22(3): p. 571-6. Published online Mar. 1, 2001.
Evans, R.W., et al., Assessment: prevention of post-lumbar puncture headaches: report of the therapeutics and technology assessment subcommittee of the american academy of neurology. Neurology, 2000. 55(7): p. 909-14. Oct 2000.
Federici, T., et al., Robust spinal motor neuron transduction following intrathecal delivery of AAV9 in pigs. Gene Ther, 2012. 19(8): p. 852-9. Epub Sep. 15, 2011.
Fendly, B.M., et al., Characterization of murine monoclonal antibodies reactive to either the human epidermal growth factor receptor or HER2/neu gene product. Cancer Res, 1990. 50(5): p. 1550-8. Mar. 1990.
Ferrario, C., et al., Intrathecal trastuzumab and thiotepa for leptomeningeal spread of breast cancer. Ann Oncol, 2009. 20(4): p. 792-5. Epub Feb. 17, 2009.
Flotte, T.R., et al., Phase 2 clinical trial of a recombinant adeno-associated viral vector expressing alpha1-antitrypsin: interim results. Hum Gene Ther, 2011. 22(10): p. 1239-47. Published Online:May 24, 2011.
Foust, K.D., et al., Intravascular AAV9 preferentially targets neonatal neurons and adult astrocytes. Nat Biotechnol, 2009. 27(1): p. 59-65. Epub Dec. 21, 2008.
Foust, K.D., et al., Rescue of the spinal muscular atrophy phenotype in a mouse model by early postnatal delivery of SMN. Nat Biotechnol, 2010. 28(3): p. 271-4. Epub Feb. 28, 2010.
Gabos, Z., et al., Prognostic significance of human epidermal growth factor receptor positivity for the development of brain metastasis after newly diagnosed breast cancer. J Clin Oncol, 2006. 24(36): p. 5658-63. Epub Nov. 13, 2006.
Gaedcke, J., et al., Predominance of the basal type and HER-2/neu type in brain metastasis from breast cancer. Mod Pathol, 2007. 20(8): p. 864-70. Epub Jun. 1, 2007.
Gakhar, G., et al., Hydronephrosis and urine retention in estrogen-implanted athymic nude mice. Vet Pathol, 2009. 46(3): p. 505-8. Epub Jan. 27, 2009.
Gao, G., et al., Adeno-associated viruses undergo substantial evolution in primates during natural infections. Proc Natl Acad Sci U S A, 2003. 100(10): p. 6081-6. Epub Apr. 25, 2003.
Gao, G., et al., Clades of Adeno-associated viruses are widely disseminated in human tissues. J Virol, 2004. 78(12): p. 6381-8. Jun. 2004.
Gao, G.P., et al., Novel adeno-associated viruses from rhesus monkeys as vectors for human gene therapy. Proc Natl Acad Sci U S A, 2002. 99(18): p. 11854-9. Epub Aug. 21, 2002.
Garcia-Rivello, H., et al., Dilated cardiomyopathy in Erb-b4-deficient ventricular muscle. Am J Physiol Heart Circ Physiol, 2005. 289(3): p. H1153-60. Epub Apr. 29, 2005.
Gennari, R., et al., Pilot study of the mechanism of action of preoperative trastuzumab in patients with primary operable breast tumors overexpressing HER2. Clin Cancer Res, 2004. 10(17): p. 5650-5. Published first Sep. 8, 2004.
Gladstone, J.P., et al., Spontaneous CSF leak treated with percutaneous CT-guided fibrin glue. Neurology, 2005. 64(10): p. 1818-9. First published May 23, 2005.
Glantz, M.J., et al., a randomized, blinded, placebo-controlled trial of divalproex sodium prophylaxis in adults with newly diagnosed brain tumors. Neurology, 1996. 46(4): p. 985-91. Apr. 1996.

(56) References Cited

OTHER PUBLICATIONS

Gori, S., et al., Central nervous system metastases in HER-2 positive metastatic breast cancer patients treated with trastuzumab: incidence, survival, and risk factors. Oncologist, 2007. 12(7): p. 766-73. Jul. 2007.
Gower, D.J. and V.C. Gower, Infected Ommaya reservoirs. Neurosurgery, 1988. 22(6 Pt 1): p. 1116. Jun. 1988.
Graus-Porta, D., et al., ErbB-2, the preferred heterodimerization partner of all ErbB receptors, is a mediator of lateral signaling. EMBO J, 1997. 16(7): p. 1647-55.
Gray, S.J., et al., Preclinical differences of intravascular AAV9 delivery to neurons and glia: a comparative study of adult mice and nonhuman primates. Mol Ther, 2011. 19(6): p. 1058-69. Epub Apr. 12, 2011.
Grossi, P.M., et al., Efficacy of intracerebral microinfusion of trastuzumab in an athymic rat model of intracerebral metastatic breast cancer. Clin Cancer Res, 2003. 9(15): p. 5514-20. Nov. 2003.
Guarneri, V., et al., Long-Term Cardiac Tolerability of Trastuzumab in Metastatic Breast Cancer: The M.D. Anderson Cancer Center Experience. Journal of Clinical Oncology, 2006. 24(25): p. 4107-4115. Epub Aug. 14, 2006.
Gulia, S., S. Gupta, and A. Singh, Intrathecal trastuzumab for leptomeningeal carcinomatosis in patients with human epidermal growth factor receptor 2 positive breast cancer. Indian Journal of Medical and Paediatric Oncology, 2016. 37(3): p. 196-198. Jul.-Sep. 2016.
Gupta, S., Trials and tribulations. Nature, 2017. 548(7666): p. S28-S31. Published: Aug. 9, 2017.
Halbert, C.L., et al., Prevalence of neutralizing antibodies against adeno-associated virus (AAV) types 2, 5, and 6 in cystic fibrosis and normal populations: Implications for gene therapy using AAV vectors. Hum Gene Ther, 2006. 17(4): p. 440-7. Mar. 2006.
Halcrow, S.J., P.J. Crawford, and A.W. Craft, Epidermoid spinal cord tumour after lumbar puncture. Arch Dis Child, 1985. 60(10): p. 978-9. Oct. 1985.
Hatfalvi, B.I., Postulated mechanisms for postdural puncture headache and review of laboratory models. Clinical experience. Reg Anesth, 1995. 20(4): p. 329-36. Jul.-Aug. 1995.
Hinderer, C., et al., Intrathecal gene therapy corrects CNS pathology in a feline model of mucopolysaccharidosis I. Mol Ther, 2014. 22(12): p. 2018-27. Epub Jul. 16, 2014.
Hinderer, C., et al., Widespread gene transfer in the central nervous system of cynomolgus macaques following delivery of AAV9 into the cisterna magna. Mol Ther Methods Clin Dev, 2014. 1: p. 14051. Dec. 2014.
Hofer, S., et al., Intrathecal trastuzumab: dose matters. Acta Oncol, 2012. 51(7): p. 955-6. Epub Apr. 23, 2012.
Hollebecque, A., et al., First case report of intrathecal panitumumab for treatment of meningeal carcinomatousis in an EGFR mutant lung adenocarcinoma patient. Lung Cancer, 2013. 80(1): p. 113-114. Epub Jan. 23, 2013.
Hurlbut, G.D., et al., Preexisting immunity and low expression in primates highlight translational challenges for liver-directed AAV8-mediated gene therapy. Mol Ther, 2010.18(11): p. 1983-94. Epub Aug. 24, 2010.
Izumi, Y., et al., Tumour biology: Herceptin acts as an anti-angiogenic cocktail. Nature, 2002. 416(6878): p. 279-280. Published: Mar. 21, 2002.
Janin, G.B.A.A., Passage of Humanized Monoclonal Antibodies Across the Blood-Brain Barrier: Relevance in the Treatment of Cancer Brain Metastases? Journal of Applied Biopharmaceutics and Pharmacokinetics, 2014. 2: 50-58. Published on Jan. 28, 2015.
Johnson K., S.D. Lumbar Puncture: Technique, indications, contraindications, and complications in adults. 11 pages, retrieved from https://web.archive.org/web/20141013000811/http://www.uptodate.com:80/contents/lumbar-puncture-technique-indications-contraindications-and-complications-in-adults, topic last update Sep. 2013.
Jones, R.J., The role of recumbency in the prevention and treatment of postspinal headache. Anesth Analg, 1974. 53(5): p. 788-96. Sep. 1974.

Kennecke H, et al. Metastatic behavior of breast cancer subtypes. J Clin Oncol. Jul. 10, 2010;28(20):3271-7. doi: 10.1200/JCO.2009.25.9820. Epub May 24, 2010.
Kim, H.J., et al., Clinical outcome of central nervous system metastases from breast cancer: differences in survival depending on systemic treatment. J Neurooncol, 2012. 106(2): p. 303-13. Epub Sep. 22, 2011.
Kirsch, D.G., et al., Survival after brain metastases from breast cancer in the trastuzumab era. J Clin Oncol, 2005. 23(9): p. 2114-6; author reply 2116-7. Mar. 2005.
Klein, R.L., D.B. Wang, and M.A. King, Versatile somatic gene transfer for modeling neurodegenerative diseases. Neurotox Res, 2009. 16(3): p. 329-42. Epub Aug. 11, 2009.
Koo, T. and I.A. Kim, Brain metastasis in human epidermal growth factor receptor 2-positive breast cancer: from biology to treatment. Radiat Oncol J, 2016. 34(1): p. 1-9. Epub Mar. 30, 2016.
Kordbacheh, T., W.Y. Law, and I.E. Smith, Sanctuary site leptomeningeal metastases in HER-2 positive breast cancer: a review in the era of trastuzumab. Breast, 2016. 26: p. 54-58. Epub Jan. 22, 2016.
Laufman, L.R. and K.F. Forsthoefel, Use of intrathecal trastuzumab in a patient with carcinomatous meningitis. Clin Breast Cancer, 2001. 2(3): p. 235. Available online Aug. 27, 2011.
Lavi, R., et al., Standard vs atraumatic Whitacre needle for diagnostic lumbar puncture: a randomized trial. Neurology, 2006. 67(8): p. 1492-4. First published Oct. 23, 2006.
Le Rhun, E., S. Taillibert, and M.C. Chamberlain, Carcinomatous. meningitis: Leptomeningeal metastases in solid tumors. Surg Neurol Int, 2013. 4(Suppl 4): p. S265-88. May 2013.
Lee, Y.T., Breast carcinoma: pattern of metastasis at autopsy. J Surg Oncol, 1983. 23(3): p. 175-80. Jul. 1983.
Lentz, T.B., S.J. Gray, and R.J. Samulski, Viral vectors for gene delivery to the central nervous system. Neurobiol Dis, 2012. 48(2): p. 179-88. Epub Oct. 7, 2011.
Leone, J.P., et al., Prognostic factors and survival according to tumour subtype in women presenting with breast cancer brain metastases at initial diagnosis. Eur J Cancer, 2017. 74: p. 17-25. Epub Feb. 6, 2017.
Levin-Allerhand, J.A., K. Sokol, and J.D. Smith, Safe and effective method for chronic 17beta-estradiol administration to mice. Contemp Top Lab Anim Sci, 2003. 42(6): p. 33-5. Nov. 2003.
Lewis, G.D., et al., Differential responses of human tumor cell lines to anti-p185HER2 monoclonal antibodies. Cancer Immunol Immunother, 1993. 37(4): p. 255-63. Sep. 1993.
Leyland-Jones, B., Human epidermal growth factor receptor 2-positive breast cancer and central nervous system metastases. J Clin Oncol, 2009. 27(31): p. 5278-86. Epub Sep. 21, 2009.
Lin, N.U., Breast cancer brain metastases: new directions in systemic therapy. ecancermedicalscience, 2013. 7: p. 307. Published online Apr. 18, 2013.
Lin, N.U., J.R. Bellon, and E.P. Winer, CNS metastases in breast cancer. J Clin Oncol, 2004. 22(17): p. 3608-17. Sep. 2004.
Loibl, S. and L. Gianni, HER2-positive breast cancer. Lancet, 2017. 389(10087): p. 2415-2429. Epub Dec. 7, 2016.
Lu, N.T., et al., Intrathecal trastuzumab: immunotherapy improves the prognosis of leptomeningeal metastases in HER-2+ breast cancer patient. J Immunother Cancer, 2015. 3: p. 41. Published: Sep. 15, 2015.
Maersch, S., et al., Optimization of stealth adeno-associated virus vectors by randomization of immunogenic epitopes. Virology, 2010. 397(1): p. 167-75. Epub Nov. 18, 2009.
Maheshri, N., et al., Directed evolution of adeno-associated virus yields enhanced gene delivery vectors. Nat Biotechnol, 2006. 24(2): p. 198-204. Epub Jan. 22, 2006.
Makino, K., et al., Upregulation of IKKalpha/IKKbeta by integrin-linked kinase is required for HER2/neu-induced NF-kappaB antiapoptotic pathway. Oncogene, 2004. 23(21): p. 3883-7. May 2004.
Mantarro, S., et al., Risk of severe cardiotoxicity following treatment with trastuzumab: a meta-analysis of randomized and cohort studies of 29,000 women with breast cancer. Intern Emerg Med, 2016. 11(1): p. 123-40. Epub Dec. 28, 2015.

(56) References Cited

OTHER PUBLICATIONS

Martin, A.M., et al., Brain Metastases in Newly Diagnosed Breast Cancer: A Population-Based Study. JAMA Oncol, Aug. 1;3(8):1069-1077. doi: 10.1001/jamaoncol.2017.0001. Aug. 2017.
Mayer, E.L. and N.U. Lin, Long Term Follow-Up of National Surgical Adjuvant Breast and Bowel Project Trial B-31: How Well Can We Predict Cardiac Toxicity With Trastuzumab? Journal of Clinical Oncology, 2012. 30(31): p. 3. Epub Sep. 17, 2012.
McCown, T.J., Adeno-Associated Virus (AAV) Vectors in the CNS. Curr Gene Ther, 2011. 11(3): p. 181-8. Jun. 2011.
McCurdy, V.J., et al., Sustained normalization of neurological disease after intracranial gene therapy in a feline model. Sci Transl Med, 2014. 6(231): p. 231ra48. Apr. 2014.
McDonald, J.V. and T.E. Klump, Intraspinal epidermoid tumors caused by lumbar puncture. Arch Neurol, 1986. 43(9): p. 936-9. Sep. 1986.
Mead, P.A., et al., Ommaya reservoir infections: a 16-year retrospective analysis. J Infect, 2014. 68(3): p. 225-30. Epub Dec. 2013.
Mechleb, B., et al., Late onset Ommaya reservoir infection due to *Staphylococcus aureus*: case report and review of Ommaya Infections. J Infect, 2003. 46(3): p. 196-8. Available online Jan. 29, 2003.
Mego, M., et al., Intrathecal administration of trastuzumab with cytarabine and methotrexate in breast cancer patients with leptomeningeal carcinomatosis. Breast, 2011. 20(5): p. 478-80. Epub Jun. 23, 2011.
Miller, K.D., et al., Occult central nervous system involvement in patients with metastatic breast cancer: prevalence, predictive factors and impact on overall survival. Ann Oncol, 2003. 14(7): p. 1072-7. Jul. 2003.
Mingozzi, F., et al., Prevalence and pharmacological modulation of humoral immunity to AAV vectors in gene transfer to synovial tissue. Gene Ther, 2013. 20(4): p. 417-24. Epub Jul. 12, 2012.
Mir, O., et al., High-dose intrathecal trastuzumab for leptomeningeal metastases secondary to HER-2 overexpressing breast cancer. Ann Oncol, 2008. 19(11): p. 1978-80. Epub Oct. 9, 2008.
Miyake, N., et al., Global gene transfer into the CNS across the BBB after neonatal systemic delivery of single-stranded AAV vectors. Brain Res, 2011. 1389: p. 19-26. Epub Mar. 2011.
Moja, L., et al., Trastuzumab containing regimens for early breast cancer. Cochrane Database of Systematic Reviews, Apr. 18, 2012;(4):CD006243. doi: 10.1002/14651858.CD006243.pub2. First published: Apr. 18, 2012.
Molina, M.A., et al., Trastuzumab (herceptin), a humanized anti-Her2 receptor monoclonal antibody, inhibits basal and activated Her2 ectodomain cleavage in breast cancer cells. Cancer Res, 2001. 61(12): p. 4744-9. Jun. 2001.
Monteilhet, V., et al., A 10 patient case report on the impact of plasmapheresis. upon neutralizing factors against adeno-associated virus (AAV) types 1, 2, 6, and 8. Mol Ther, 2011. 19(11): p. 2084-91. Epub May 31, 2011.
Morikawa, A., et al., Characteristics and Outcomes of Patients With Breast Cancer With Leptomeningeal Metastasis. Clin Breast Cancer, 2017. 17(1): p. 23-28. Epub Jul. 25, 2016.
Mustacchi, G., et al., HER2-positive metastatic breast cancer: a changing scenario. Crit Rev Oncol Hematol, 2015. 95(1): p. 78-87. Epub Feb. 20, 2015.
Nadler, L.M., et al., Serotherapy of a patient with a monoclonal antibody directed against a human lymphoma-associated antigen. Cancer Res, 1980. 40(9): p. 3147-54. Sep. 1980.
Nathwani, A.C., et al., Long-term safety and efficacy of factor IX gene therapy in hemophilia B. N Engl J Med, 2014. 371(21): p. 1994-2004. Nov. 20, 2014.
Niikura, N., et al., Changes in tumor expression of HER2 and hormone receptors. status after neoadjuvant chemotherapy in 21,755 patients from the Japanese breast cancer registry. Ann Oncol, 2016. 27(3): p. 480-7. Epub Dec. 23, 2015.
Nonnenmacher, M. and T. Weber, Adeno-associated virus 2 infection requires endocytosis through the CLIC/GEEC pathway. Cell Host Microbe, 2011. 10(6): p. 563-76. Published: Dec. 14, 2011.
Oliveira, M., et al., Complete response in HER2+ leptomeningeal carcinomatosis from breast cancer with intrathecal trastuzumab. Breast Cancer Res Treat, 2011. 127(3): p. 841-4. Epub Mar. 3, 2011.
Onitilo, A.A., J.M. Engel, and R.V. Stankowski, Cardiovascular toxicity associated with adjuvant trastuzumab therapy: prevalence, patient characteristics, and risk factors. Therapeutic Advances in Drug Safety, 2014. 5(4): p. 154-166. Aug. 2014.
Overdijk, M.B., et al., Crosstalk between Human IgG Isotypes and Murine. Effector Cells. The Journal of Immunology, 2012. Epub Sep. 5, 2012.
Ozcelik, C., et al., Conditional mutation of the ErbB2 (HER2) receptor in cardiomyocytes leads to dilated cardiomyopathy. Proc Natl Acad Sci U S A, 2002. 99(13): p. 8880-5. Epub Jun. 18, 2002.
Paech, M.J., et al., the volume of blood for epidural blood patch in obstetrics: a randomized, blinded clinical trial. Anesth Analg, 2011. 113(1): p. 126-33. Epub May 19, 2011.
Park, I.H., et al., Concordant HER2 status between metastatic breast cancer cells in CSF and primary breast cancer tissue. Breast Cancer Research and Treatment, 2010. 123(1): p. 125-128. Epub Nov. 15, 2009.
Park, I.H., et al., Trastuzumab treatment beyond brain progression in HER2-positive metastatic breast cancer. Ann Oncol, 2009. 20(1): p. 56-62. Epub Jul. 29, 2008.
Park, J.W., et al., Unraveling the biologic and clinical complexities of HER2. Clin Breast Cancer, 2008. 8(5): p. 392-401. Oct. 2008.
Park, W.Y., et al., Intrathecal Trastuzumab Treatment in Patients with Breast Cancer and Leptomeningeal Carcinomatosis. Cancer Res Treat, 2016. 48(2): p. 843-7. Epub Mar. 2, 2015.
Park, Y., et al., Current status of therapy for breast cancer worldwide and in Japan. World J Clin Oncol, 2011. 2(2): p. 125-34. Published online Feb. 10, 2011.
Patanaphan, V., O.M. Salazar, and R. Risco, Breast cancer: metastatic patterns and their prognosis. South Med J, 1988. 81(9): p. 1109-12. Sep. 1988.
Pearse, G., et al., Urinary retention and cystitis associated with subcutaneous estradiol pellets in female nude mice. Toxicol Pathol, 2009. 37(2): p. 227-34. Epub Jan. 29, 2009.
Peltola, J., et al., Spinal epidural haematoma complicating diagnostic lumbar puncture. Lancet, 1996. 347(8994): p. 131. Jan. 1996.
Pentassuglia, L. and D.B. Sawyer, The role of Neuregulin-1beta/ ErbB signaling in the heart. Exp Cell Res, 2009. 315(4): p. 627-37. Epub Sep. 3, 2008.
Perrin, R.G., et al., Experience with Ommaya reservoir in 120 consecutive patients with meningeal malignancy. Can J Neurol Sci, 1990. 17(2): p. 190-2. May 1990.
Pestalozzi, B.C., et al., Identifying breast cancer patients at risk for Central Nervous System (CNS) metastases in trials of the International Breast Cancer Study Group (IBCSG). Annals of Oncology, 2006. 17(6): p. 935-944. Epub Apr. 7, 2006.
Pietras, R.J., et al., Monoclonal antibody to HER-2/neureceptor modulates repair of radiation-induced DNA damage and enhances radiosensitivity of human breast cancer cells overexpressing this oncogene. Cancer Res, 1999. 59(6): p. 1347-55. Mar. 1999.
Pietras, R.J., et al., Remission of human breast cancer xenografts on therapy with humanized monoclonal antibody to HER-2 receptor and DNA-reactive drugs. Oncogene, 1998. 17(17): p. 2235-49. Oct. 1998.
Pillay, S., et al., An essential receptor for adeno-associated virus infection. Nature, 2016. 530(7588): p. 108-12. . Epub Jan. 27, 2016.
Pinkas-Kramarski, R., et al., Diversification of Neu differentiation factor and epidermal growth factor signaling by combinatorial receptor interactions. EMBO J, 1996. 15(10): p. 2452-67. May 1996
Pivot, X., et al., Cerebel (EGF111438): A Phase III, Randomized, Open-Label Study of Lapatinib Plus Capecitabine Versus Trastuzumab Plus Capecitabine in Patients With Human Epidermal Growth Factor Receptor 2-Positive Metastatic. Breast. Cancer. Journal of Clinical Oncology, 2015. 33(14): p. 1564-1573. Epub Jan. 20, 2015.
Platini, C., J. Long, and S. Walter, Meningeal carcinomatosis from breast cancer treated with intrathecal trastuzumab. Lancet Oncol, 2006. 7(9): p. 778-80. Published: Sep. 2006.
Pluchart, H., et al., Long-Term Survivor with Intrathecal and Intravenous. Trastuzumab Treatment in Metastatic Breast Cancer. Target Oncol, 2016. 11(5): p. 687-691. First Online: Apr. 4, 2016.

(56) References Cited

OTHER PUBLICATIONS

Ramakrishna, N., et al., Recommendations on disease management for patients with advanced human epidermal growth factor receptor 2-positive breast cancer and brain metastases: American Society of Clinical Oncology clinical practice guideline. J Clin Oncol, 2014. 32(19): p. 2100-8. Epub May 5, 2014

Reyes, F., et al., ACVBP versus CHOP plus radiotherapy for localized aggressive. lymphoma. N Engl J Med, 2005. 352(12): p. 1197-205. Mar. 2005.

Rivera, V.M., et al., Long-term pharmacologically regulated expression of erythropoietin in primates following AAV-mediated gene transfer. Blood, 2005. 105(4): p. 1424-30. Epub Oct. 26, 2004.

Romond, E.H., et al., Seven-Year Follow-Up Assessment of Cardiac Function in NSABP B-31, a Randomized Trial Comparing Doxorubicin and Cyclophosphamide. Followed by Paclitaxel (ACP) With ACP Plus Trastuzumab As Adjuvant Therapy for Patients With Node-Positive, Human Epidermal Growth Factor Receptor 2-Positive Breast Cancer. Journal of Clinical Oncology, 2012. 30(31): p. 3792-3799. Epub Sep. 17, 2012.

Romond, E.H., et al., Trastuzumab plus adjuvant chemotherapy for operable HER2-positive breast cancer. N Engl J Med, 2005. 353(16): p. 1673-84. Oct. 2005.

Rubenstein, J.L., et al., Multicenter phase 1 trial of intraventricular immunochemotherapy in recurrent CNS lymphoma. Blood, 2013. 121(5): p. 745-751. Epub Nov. 29, 2012.

Sahebjam, S., et al., Experimental Treatments for Leptomeningeal Metastases From Solid Malignancies. Cancer Control, 2017. 24(1): p. 42-46. Jan. 2017.

Samaranch, L., et al., Strong cortical and spinal cord transduction after AAV7 and AAV9 delivery into the cerebrospinal fluid of nonhuman primates. Hum Gene Ther, 2013. 24(5): p. 526-32. Mar. 2013.

Schuster, D.J., et al., Biodistribution of adeno-associated virus serotype 9 (AAV9) vector after intrathecal and intravenous delivery in mouse. Front Neuroanat, 2014. 8: p. 42. Jun. 2014.

Shaikh, F., et al., Ultrasound imaging for lumbar punctures and epidural catheterisations: systematic review and meta-analysis. BMJ, 2013. 346: p. f1720. (Published Mar. 26, 2013).

Shenoy, C., et al., Cardiovascular Complications of Breast Cancer Therapy in Older Adults. The Oncologist, 2011. 16(8): p. 1138-1143.Epub Jul. 7, 2011.

Shi, Y., et al., Trastuzumab triggers phagocytic killing of high HER2 cancer cells in vitro and in vivo by interaction with Fcgamma receptors on macrophages. J Immunol, 2015. 194(9): p. 4379-86. Epub Mar. 20, 2015.

Slamon, D.J., et al., Human breast cancer: correlation of relapse and survival with amplification of the HER-2/neu oncogene. Science, 1987. 235(4785): p. 177-82. Jan. 1987.

Slamon, D.J., et al., Use of chemotherapy plus a monoclonal antibody against HER2 for metastatic breast cancer that overexpresses HER2. N Engl J Med, 2001. 344(11): p. 783- 92. Mar. 2001.

Sonntag, F., et al., Adeno-associated virus type 2 capsids with externalized VP1/VP2 trafficking domains are generated prior to passage through the cytoplasm and are maintained until uncoating occurs in the nucleus. J Virol, 2006. 80(22): p. 11040-54. Epub Sep. 6, 2006.

Souglakos, J., et al., Central nervous system relapse in patients with breast cancer is associated with advanced stages, with the presence of circulating occult. tumor cells and with the HER2/neu status. Breast Cancer Research, 2006. 8(4): p. R36. Published: Jul. 17, 2006.

Stemmler, H.J., et al., Application of intrathecal trastuzumab (Herceptintrade mark) for treatment of meningeal carcinomatosis in HER2-overexpressing metastatic breast cancer. Oncol Rep, 2006. 15(5): p. 1373-7. Published online on: May 1, 2006.

Stemmler, H.J., et al., Characteristics of patients with brain metastases receiving trastuzumab for HER2 overexpressing metastatic breast cancer. Breast, 2006. 15(2): p. 219-25. Epub Jul. 18, 2005.

Stemmler, H.J., et al., Intrathecal trastuzumab (Herceptin) and methotrexate for meningeal carcinomatosis in HER2-overexpressing metastatic breast cancer: a case report. Anticancer Drugs, 2008. 19(8): p. 832-6. Sep. 2008.

Stemmler, H.J., et al., Ratio of trastuzumab levels in serum and cerebrospinal. fluid is altered in HER2-positive breast cancer patients with brain metastases and impairment of blood-brain barrier. Anticancer Drugs, 2007. 18(1): p. 23-8. Jan. 2007.

Szvalb, A.D., et al., Ommaya reservoir-related infections: clinical manifestations and treatment outcomes. J Infect, 2014. 68(3): p. 216-24. Epub Dec. 17, 2013.

Tsukada, Y., et al., Central nervous system metastasis from breast carcinoma. Autopsy study. Cancer, 1983. 52(12): p. 2349-54. Dec. 1983.

Vermeulen, M. and J. Van Gijn, The diagnosis of subarachnoid haemorrhage. J Neurol Neurosurg Psychiatry, 1990. 53(5): p. 365-72. May 1990.

Vite, C.H., et al., Effective gene therapy for an inherited CNS disease in a large animal model. Ann Neurol, 2005. 57(3): p. 355-64. First published: Feb. 24, 2005.

Vogel, C.L., et al., Efficacy and safety of trastuzumab as a single agent in first-line treatment of HER2-overexpressing metastatic breast cancer. J Clin Oncol, 2002. 20(3): p. 719-26. Feb. 1, 2002.

Von Minckwitz, G., et al., Adjuvant Pertuzumab and Trastuzumab in Early HER2-Positive Breast Cancer. N Engl J Med, 2017. 377(2): p. 122-131. Epub 2017 Jun 5. Published on Jun. 5, 2017, and updated on Jul. 13, 2017.

Vu, T. and F.X. Claret, Trastuzumab: updated mechanisms of action and resistance in breast cancer. Front Oncol, 2012. 2: p. 62. Published online: Jun. 18, 2012.

Wang, D.B., et al., Expansive gene transfer in the rat CNS rapidly produces amyotrophic lateral sclerosis relevant sequelae when TDP-43 is overexpressed. Mol Ther, 2010. 18(12): p. 2064-74. Epub Sep. 28, 2010.

Wang, L., et al., Impact of pre-existing immunity on gene transfer to nonhuman primate liver with adeno-associated virus 8 vectors. Hum Gene Ther, 2011. 22(11): p. 1389-401. Published online: Apr. 8, 2011.

Wang, L., et al., Sustained correction of disease in naive and AAV2-pretreated hemophilia B dogs: AAV2/8-mediated, liver-directed gene therapy. Blood, 2005. 105(8): p. 3079-86. Epub Jan. 6, 2005.

Weil, R.J., et al., Breast cancer metastasis to the central nervous system. Am J. Pathol, 2005. 167(4): p. 913-20. Oct. 2005.

Weiner, G.J., Rituximab: mechanism of action. Seminars in hematology, 2010. 47(2): p. 115-123. Available online Mar. 27, 2010.

Wolff, A.C., et al., Recommendations for Human Epidermal Growth Factor Receptor 2 Testing in Breast Cancer: American Society of Clinical Oncology/College of American Pathologists Clinical Practice Guideline Update. Journal of Clinical Oncology, 2013. 31(31): p. 3997-4013. Epub Oct. 7, 2013.

Xia, W., et al., Regulation of survivin by ErbB2 signaling: therapeutic implications. For ErbB2-overexpressing breast cancers. Cancer Res, 2006. 66(3): p. 1640-7. Published first Feb. 1, 2006.

Xia, W., et al., Truncated ErbB2 receptor (p95ErbB2) is regulated by heregulin. through heterodimer formation with ErbB3 yet remains sensitive to the dual. EGFR/ErbB2 kinase inhibitor GW572016. Oncogene, 2004. 23(3): p. 646-53. Published: Jan. 22, 2004.

Yakes, F.M., et al., Herceptin-induced inhibition of phosphatidylinositol-3 kinase and Akt Is required for antibody-mediated effects on p27, cyclin D1, and antitumor action. Cancer Res, 2002. 62(14): p. 4132-41. Published first Jul. 15, 2002.

Yarden, Y. and M.X. Sliwkowski, Untangling the ErbB signalling network. Nat Rev Mol Cell Biol, 2001. 2(2): p. 127-37. Published: Feb. 1, 2001.

Yust-Katz, S., et al., Breast cancer and leptomeningeal disease (LMD): hormone receptor status influences time to development of LMD and survival from LMD diagnosis. J Neurooncol, 2013. 114(2): p. 229-35. Published online: Jun. 12, 2013.

Yau, T., et al., Incidence, pattern and timing of brain metastases among patients with advanced breast cancer treated with trastuzumab. Acta Oncol, 2006. 45(2): p. 196-201.

(56) References Cited

OTHER PUBLICATIONS

Medicines in Development Biologics, 2013 Report, pp. 1-87, a publication of PhRMA's Communications & Public Affairs Department. (Feb. 7, 2013).
Rudikoff et al., Single amino acid substitution altering antigen-binding specificity PNAS, vol. 79(6):1979-1983, Mar. 1982.
Su et al., the role of Antibody Vκ Framework 3 region towards Antigen binding: Effects on recombinant production and Protein L binding, Scientific Reports, vol. 7:3766, Jun. 2017.
Drug Information of Pertuzumab (Accession No. DB06366) retrieved from: https://www.drugbank.ca/drugs/DB06366 on Jan. 25, 2017.
Drug Information of Trastuzumab (Accession No. DB00072 (BTD00098, BIOD00098)) retrieved from: https://www.drugbank.ca/drugs/DB00072 on Jan. 25, 2017.
International Search Report and Written Opinion of the International Searching Authority /US issued on PCT/US2015/027491 dated Sep. 21, 2015.
Extended European search report issued in the corresponding European Patent Application No. 15782834.4, dated Sep. 27, 2017.
Communication pursuant to Article 94(3) EPC issued in the corresponding European Patent Application No. 15782834.4, dated Feb. 21, 2019.
Office Action issued in the corresponding Japanese Patent Application No. 2016-564061, dated Feb. 13, 2019, with an unofficial translation provided by Japanese Agent.
Response filed on Apr. 23, 2018 in reply to the Oct. 13, 2017 Communication requesting Applicant's comment dated Sep. 27, 2017 extended European search report issued in the corresponding European Patent Application No. 15782834.4.
Office Action issued in the corresponding Japanese Patent Application No. 2016-564061, dated Oct. 9, 2019, with an unofficial translation provided by Japanese Agent.
Communication issued in corresponding European Patent Application No. 15782834.4, dated Apr. 30, 2020.
Non-Final Office Action dated Mar. 27, 2018 issued in corresponding U.S. Appl. No. 15/306,413, and Response filed Jul. 27, 2018.
Final Office Action dated Nov. 29, 2018 issued in corresponding U.S. Appl. No. 15/306,413, and Response filed Mar. 29, 2019.
Non-Final Office Action dated Nov. 7, 2019 issued in corresponding U.S. Appl. No. 15/306,413, and Response filed Feb. 26, 2020.
Nahta, R., and Esteva, FJ., Trastuzumab: triumphs and tribulations, Oncogene, vol. 26(25):3637-43, May 2007.
Office Action dated Dec. 14, 2021 issued in corresponding Japanese Patent Application No. 2020-019623, with English translation provided by local Agent.
Communication dated Mar. 29, 2022 issued in corresponding European Patent Application No. 15782834.4.
Final Rejection and Decision of Dismissal of Amendment dated Oct. 26, 2022 issued in corresponding Japanese Patent Application No. 2020-019623, with English translation provided by local Agent.
Pre-Trial Re-examination Report dated May 17, 2023 issued in corresponding Japanese Patent Application No. 2020-019623, with English translation provided by local Agent.

\* cited by examiner

FIG. 1

```
001        011        021        031        041        051        061        071        081
myrmqllsci alslalvtns evqlvesggg lvqpggslrl scaasgfnik dtyihwvrqa pgkglewvar iyptngytry adsvkgrfti
                     001        011        021        031        041        051        060

091        101        111        121        131        141        151        161        171
sadtskntay lqmnslraed tavyycsrwg gdgfyamdyw gggtlvtvss astkgpsvfp lapsskstsg gtaalgclvk dyfpepvtvs
070        080        087        097        104        118        128        138        148

181        191        201        211        221        231        241        251        261
wnsgaltsgv htfpavlqss glyslssvvt vpssslgtqt yicnvnhkps ntkvdkkvep kscdkthtcp pcpapellgg psvflfppkp
158        168        178        188        198        208        218        228        238

271        281        291        301        311        321        331        341        351
kdtlmisrtp evtcvvvdvs hedpevkfnw yvdgvevhna ktkpreeqyn styrvvsvlt vlhqdwlngk eykckvsnka lpapiektis
248        258        268        278        288        298        308        318        328

361        371        381        391        401        411        421        431        441
kakgqprepq vytlppsree mtknqvsltc lvkgfypsdi avewesngqp ennykttppv ldsdgsffly skltvdksrw qqgnvfscsv
338        348        358        368        378        388        398        408        418

451        461
mhealhnhyt qkslslspg
428        438
```

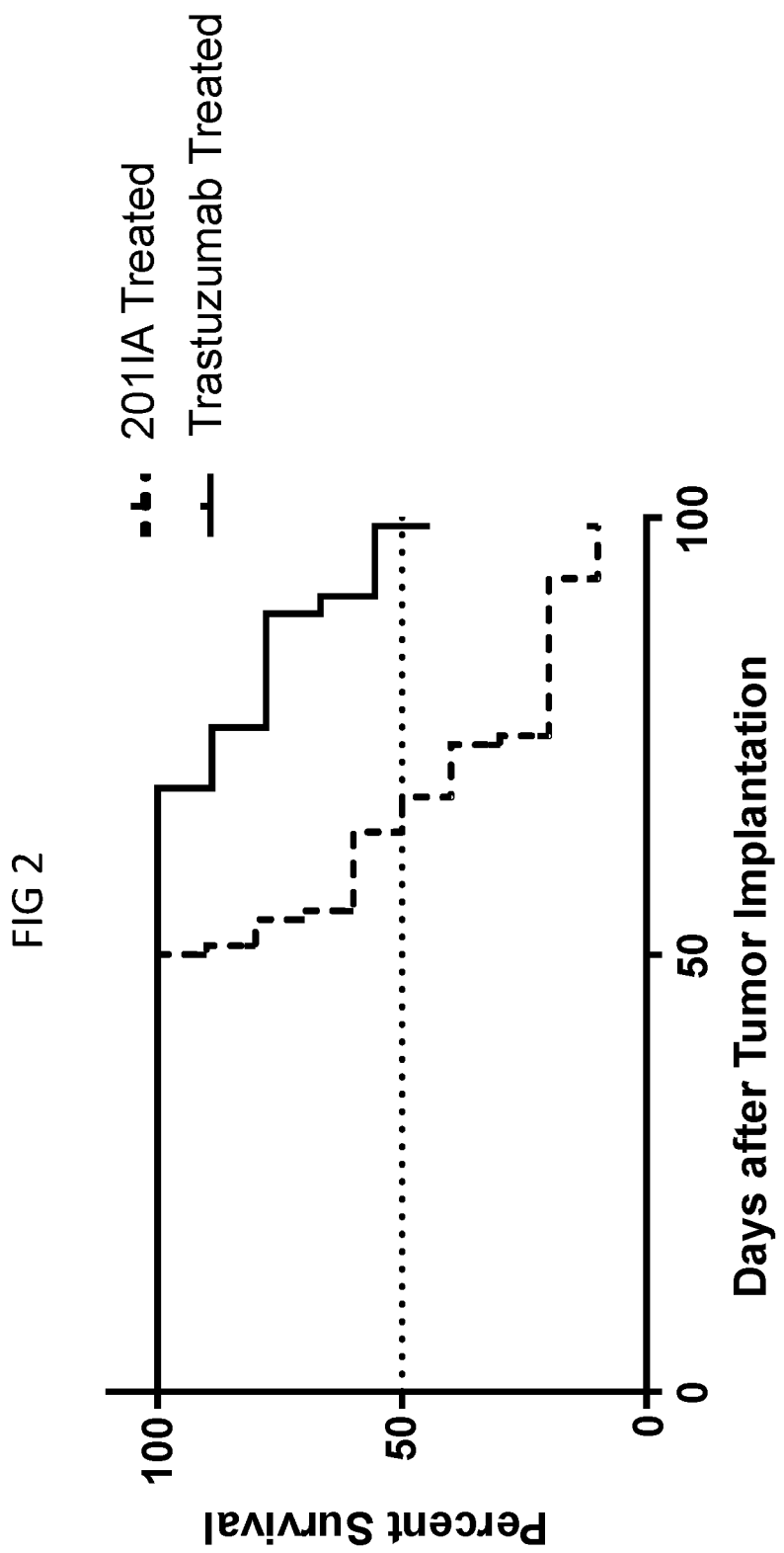

METHODS AND COMPOSITIONS FOR TREATING METASTATIC BREAST CANCER AND OTHER CANCERS IN THE BRAIN

BACKGROUND OF THE INVENTION

Brain metastases are a common and devastating sequelae of breast cancer for which treatment options are few and inadequate. 6-16% of breast cancer patients develop central nervous system (CNS) metastases. These patients have a 20% one-year and 1.3% five-year median survival from the time of diagnosis. DiStefano A, et al, Cancer. 1979; 44:1913-1918; Takakura K, et al, Metastatic tumors of the central nervous system. Tokyo: Igaku-Shoin, 1982; Hall W A, et al, Long-term survival with metastatic cancer to the brain. Med Oncol. 2000 November; 17(4):279-86; Pieńkowski T, Zielinski C C. Trastuzumab treatment in patients with breast cancer and metastatic CNS disease. Ann Oncol. 2010 May; 21(5):917-24. Surgical resection of brain metastases is often infeasible, and chemotherapeutic agents are mostly excluded from the CNS by the blood brain barrier (BBB) [Nakayama A, et al, Antitumor Activity of TAK-285, an Investigational, Non-Pgp Substrate HER2/EGFR Kinase Inhibitor, in Cultured Tumor Cells, Mouse and Rat Xenograft Tumors, and in an HER2-Positive Brain Metastasis Model, J Cancer. 2013 Aug. 16; 4(7)]. Alternative therapies to treat breast cancer brain metastases are needed.

Breast cancers that overexpress the HER2 receptor tyrosine kinase have a high propensity to metastasize to the CNS and comprise 25-30% of all breast cancer cases [Bendell J C, et al, Central nervous system metastases in women who receive trastuzumab-based therapy for metastatic breast carcinoma. Cancer. 2003 Jun. 15; 97(12):2972-7]. Trastuzumab (Herceptin®) is a first-line therapeutic immunoglobulin G (IgG) monoclonal antibody (mAb) directed toward HER2; this antibody has been reported to significantly improve survival of patients with HER2 positive disease [Lin N U, et al, Brain metastases: the HER2 paradigm. Clin Cancer Res. 2007 Mar. 15; 13(6):1648-55; Palmieri D, et al, Her-2 overexpression increases the metastatic outgrowth of breast cancer cells in the brain. Cancer Res. 2007 May 1; 67(9): 4190-8]. However, patients that benefit from trastuzumab often experience simultaneous progression of CNS disease because mAbs do not cross the BBB [Nakayama, cited above]. Injecting trastuzumab directly into the CNS has been proven to be safe, and intrathecal administration of trastuzumab to patients with leptomeningeal carcinomatosis has been reported to increase overall survival from 2 to 13.5 months [Zagouri F, et al, Intrathecal administration of trastuzumab for the treatment of meningeal carcinomatosis in HER2-positive metastatic breast cancer: a systematic review and pooled analysis. Breast Cancer Res Treat. 2013 May; 139(1):13-22]. Leptomeningeal carcinomatosis is associated with an impaired, rather than an intact, blood-brain barrier. Park, E-J, et al, J Controlled Release, 163 (2012), 277-284 report that focused ultrasound bursts combined with circulating microbubbles can temporarily permeabilize both the blood brain barrier and the blood tumor barrier for trastuzumab.

While current therapies have led to an improved control of the systemic disease, treatment of metastatic dissemination of human breast cancer into the CNS is a great therapeutic challenge.

SUMMARY OF THE INVENTION

An anti-neoplastic composition is provided which comprises at least one AAV vector formulated for delivery to the central nervous system, wherein said composition comprises at least one expression cassette which contains sequences encoding an anti-neoplastic immunoglobulin product for delivery to the CNS operably linked to expression control sequences therefor and a pharmaceutically acceptable carrier. In one example, the anti-neoplastic immunoglobulin construct comprises an immunoglobulin modified to have decreased or no measurable affinity for neonatal Fc receptor (FcRn). Suitably, this composition is effective for use in retarding the growth of a tumor in the brain and/or for reducing tumor size and/or for increasing progression-free survival of the subject.

In one aspect, a composition as provided herein comprises an AAV viral vector having an AAV9 capsid and having packaged therein an expression cassette encoding an anti-Her2 IgG antibody or a functional fragment thereof which comprises an anti-Her2 heavy chain which has disrupted binding for FcRn.

In another aspect, a method for retarding the growth of a tumor in the brain is provided, which involves administering a composition as described herein to the central nervous system e.g., intrathecally. In one aspect, the composition is administered in the absence of chemical or physical disruption of the blood brain barrier.

In yet another aspect, the invention provides a method for treating a neoplasm in the brain by administering a composition as described herein to a subject in need thereof.

In yet another aspect, the invention provides an anti-neoplastic regimen comprising administering a composition as described herein in combination with an antibody or other biologic drug, a small molecule anti-neoplastic agent, radiation, and/or a chemotherapeutic agent.

Still other aspects and advantages of the invention will be readily apparent from the following detailed description of the invention.

BRIEF DESCRIPTION OF THE DRAWINGS

FIG. 1 provides the amino acid sequence of the heavy chain of the polypeptide of trastuzumab, with the sequence listing numbering [SEQ ID NO:25] above the sequence and the conventional Eu (IMGT) numbering below the sequence.

FIG. 2 provides a survival curve of mice given $1 \times 10^{11}$ GC ICV of AAV9.trastuzumab or AAV9.2011A prophylactically, then implanted with BT474-M1.ffluc tumor cells in the brain 21 days after vector administration. The median survival of 2011A group (sham treatment) is shown to be 66 days, whereas the median survival of the group treated with AAV9.trastuzumab is 99 days, a 33% increase in survival rate.

DETAILED DESCRIPTION OF THE INVENTION

The compositions and regimens described herein are useful for delivery of anti-neoplastic immunoglobulin constructs to the central nervous system. Compositions described herein comprising AAV-Ig are well suited for central nervous system (CNS) cancers (neoplasms), and particularly for those located in the brain.

As used herein, the term "CNS neoplasms" includes primary or metastatic cancers, which may be located in the brain (intracranial), meninges (connective tissue layer covering brain and spinal cord), or spinal cord. Examples of primary CNS cancers could be gliomas (which may include glioblastoma (also known as glioblastoma multiforme), astrocytomas, oligodendrogliomas, and ependymomas, and mixed gliomas), meningiomas, medulloblastomas, neuromas, and primary CNS lymphoma (in the brain, spinal cord, or meninges), among others. Examples of metastatic cancers include those originating in another tissue or organ, e.g., breast, lung, lymphoma, leukemia, melanoma (skin cancer), colon, kidney, prostate, or other types that metastasize to brain.

As used herein, an "anti-neoplastic" immunoglobulin construct (including antibody or antibody fragment as defined herein) encodes a polypeptide-based moiety which binds to a cell-surface antigen or receptor located on a cancer cell or solid tumor and which inhibits or prevents the growth and spread of tumors, or malignant cells in a non-solid tumor, and optionally, reduces the size of tumors. The anti-neoplastic immunoglobulin polypeptides can function by a number of mechanisms, e.g., inhibiting tumor cell growth by blocking a growth factor receptor, cross-linking cell membrane antigens to deliver signals that control the cell cycle, blocking angiogenesis, blocking DNA repair post chemotherapy, or even inducing cell death. Alternatively, they can influence tumor growth indirectly by activating host immune effector functions such as antibody-dependent and complement-mediated cell cytotoxicity. In one embodiment, the anti-neoplastic effect of the compositions and regimens described herein can be measured by reduction of tumor size and/or by an increased progression-free survival rate as compared to subjects which are untreated or treated with other regimens.

The term "immunoglobulin" is used herein to include antibodies, functional fragments thereof, and immunoadhesins. Antibodies may exist in a variety of forms including, for example, polyclonal antibodies, monoclonal antibodies, camelized single domain antibodies, intracellular antibodies ("intrabodies"), recombinant antibodies, multispecific antibody, antibody fragments, such as, Fv, Fab, F(ab)$_2$, F(ab)$_3$, Fab', Fab'-SH, F(ab')$_2$, single chain variable fragment antibodies (scFv), tandem/bis-scFv, Fc, pFc', scFvFc (or scFv-Fc), disulfide Fv (dsfv), bispecific antibodies (bc-scFv) such as BiTE antibodies; camelid antibodies, resurfaced antibodies, humanized antibodies, fully human antibodies, single-domain antibody (sdAb, also known as NANOBODY®), chimeric antibodies, chimeric antibodies comprising at least one human constant region, and the like. "Antibody fragment" refers to at least a portion of the variable region of the immunoglobulin that binds to its target, e.g., the tumor cell.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

As used herein, an "expression cassette" refers to a nucleic acid molecule which comprises an immunoglobulin gene(s) (e.g., an immunoglobulin variable region, an immunoglobulin constant region, a full-length light chain, a full-length heavy chain or another fragment of an immunoglobulin construct), promoter, and may include other regulatory sequences therefor, which cassette may be delivered via a genetic element (e.g., a plasmid) to a packaging host cell and packaged into the capsid of a viral vector (e.g., a viral particle). Typically, such an expression cassette for generating a viral vector contains the immunoglobulin sequences described herein flanked by packaging signals of the viral genome and other expression control sequences such as those described herein.

As described above, the term "about" when used to modify a numerical value means a variation of ±10%, unless otherwise specified.

As used throughout this specification and the claims, the terms "comprise" and "contain" and its variants including, "comprises", "comprising", "contains" and "containing", among other variants, is inclusive of other components, elements, integers, steps and the like. The term "consists of" or "consisting of" are exclusive of other components, elements, integers, steps and the like.

For expression from an AAV vector, the amino acid sequences for an anti-neoplastic immunoglobulin construct are selected from those which have been published, those which are commercially available, and the coding sequences described herein. Anti-neoplastic immunoglobulins as described herein may target a human epidermal growth factor receptor (HER), such as HER2. An example of trastuzumab is a recombinant IgG1 kappa, humanized monoclonal antibody that selectively binds with high affinity in a cell-based assay (Kd=5 nM) to the extracellular domain of the human epidermal growth factor receptor protein. The commercially available product is produced in CHO cell culture. See, e.g., web site: drugbank.ca/drugs/DB00072. The amino acid sequences of the trastuzumab light chains 1 and 2 and heavy chains 1 and 2, as well as sequences obtained from a study of the x-ray structure of trastuzumab, are provided on this database at accession number DB00072, which sequences are incorporated herein by reference. See, also, 212-Pb-TCMC-trastuzumab [Areva Med, Bethesda, MD]. Another antibody of interest includes, e.g., pertuzumab, a recombinant humanized monoclonal antibody that targets the extracellular dimerization domain (Subdomain II) of the human epidermal growth factor receptor 2 protein (HER2). It consists of two heavy chains and two lights chains that have 448 and 214 residues respectively. FDA approved Jun. 8, 2012. The amino acid sequences of its heavy chain and light chain are provided, e.g., in web site: drugbank.ca/drugs/DB06366 (synonyms include 2C4, MOAB 2C4, monoclonal antibody 2C4, and rhuMAb-2C4) on this database at accession number DB06366. In addition to HER2, other HER targets may be selected.

For example, MM-121/SAR256212 is a fully human monoclonal antibody that targets the HER3 receptor [Merrimack's Network Biology] and which has been reported to be useful in the treatment of non-small cell lung cancer (NSCLC), breast cancer and ovarian cancer. SAR256212 is an investigational fully human monoclonal antibody that targets the HER3 (ErbB3) receptor [Sanofi Oncology]. Another anti-Her3/EGFR antibody is RG7597 [Genentech], described as being useful in head and neck cancers. Another antibody, margetuximab (or MGAH22), a next-generation, Fc-optimized monoclonal antibody (mAb) that targets HER [MacroGenics], may also be utilized.

Alternatively, other human epithelial cell surface markers and/or other tumor receptors or antigens may be targeted. Examples of other cell surface marker targets include, e.g., 5T4, CA-125, CEA (e.g., targeted by labetuzumab), CD3, CD19, CD20 (e.g., targeted by rituximab), CD22 (e.g., targeted by epratuzumab or veltuzumab), CD30, CD33, CD40, CD44, CD51 (also integrin av133), CD133 (e.g., glioblastoma cells), CTLA-4 (e.g., Ipilimumab used in treatment of, e.g., neuroblastoma), Chemokine (C-X-C Motif) Receptor 2 (CXCR2) (expressed in different regions in brain; e.g., Anti-CXCR2 (extracellular) antibody #ACR-012 (Alomene Labs)); EpCAM, fibroblast activation protein (FAP) [see, e.g., WO 2012020006 A2, brain cancers], folate receptor alpha (e.g., pediatric ependymal brain tumors, head and neck cancers), fibroblast growth factor receptor 1 (FGFR1) (see, et al, WO2012125124A1 for discussion treatment of cancers with anti-FGFR1 antibodies), FGFR2 (see, e.g., antibodies described in WO2013076186A and WO2011143318A2), FGFR3 (see, e.g., antibodies described in U.S. Pat. No. 8,187,601 and WO2010111367A1), FGFR4 (see, e.g., anti-FGFR4 antibodies described in WO2012138975A1), hepatocyte growth factor (HGF) (see, e.g., antibodies in WO2010119991A3), integrin IGF-1 receptor, gangioloside GD2 (see, e.g., antibodies described in WO2011160119A2), ganglioside GD3, transmembrane glycoprotein NMB (GPNMB) (associated with gliomas, among others and target of the antibody glembatumumab (CR011), mucin, MUC1, phosphatidylserine (e.g., targeted by bavituximab, Peregrine Pharmaceuticals, Inc], prostatic carcinoma cells, PD-L1 (e.g., nivolumab (BMS-936558, MDX-1106, ONO-4538), a fully human gG4, e.g., metastatic melanoma], platelet-derived growth factor receptor, alpha (PDGFR α) or CD140, tumor associated glycoprotein 72 (TAG-72), tenascin C, tumor necrosis factor (TNF) receptor (TRAIL-R2), vascular endothelial growth factor (VEGF)-A (e.g., targeted by bevacizumab) and VEGFR2 (e.g., targeted by ramucirumab). Other antibodies and their targets include, e.g., APN301 (hu14.19-IL2), a monoclonal antibody [malignant melanoma and neuroblastoma in children, Apeiron Biologics, Vienna, Austria]. See, also, e.g., monoclonal antibody, 8H9, which has been described as being useful for the treatment of solid tumors, including metastatic brain cancer. The monoclonal antibody 8H9 is a mouse IgG1 antibody with specificity for the B7H3 antigen [United Therapeutics Corporation]. This mouse antibody can be humanized. Still other immunoglobulin constructs targeting the B7-H3 and/or the B7-H4 antigen may be used in the invention. Another antibody is S58 (anti-GD2, neuroblastoma). Cotara™ [Perregrince Pharmaceuticals] is a monoclonal antibody described for treatment of recurrent glioblastoma. Other antibodies may include, e.g., avastin, ficlatuzumab, medi-575, and olaratumab. Still other immunoglobulin constructs or monoclonal antibodies may be selected for use in the invention. See, e.g., Medicines in Development Biologics, 2013 Report, pp. 1-87, a publication of PhRMA's Communications & Public Affairs Department. (202) 835-3460, which is incorporated by reference herein.

Once the target and immunoglobulin are selected, the coding sequences for the selected immunoglobulin (e.g., heavy and/or light chain(s)) may be obtained and/or synthesized. Methods for sequencing a protein, peptide, or polypeptide (e.g., as an immunoglobulin) are known to those of skill in the art. Once the sequence of a protein is known, there are web-based and commercially available computer programs, as well as service based companies which back translate the amino acids sequences to nucleic acid coding sequences. See, e.g., backtranseq by EMBOSS, world wide web at: ebi.ac.uk/Tools/st/; Gene Infinity world wide web @ geneinfinity.org/sms/sms_backtranslation.html); ExPasy (world wide web: expasy.org/tools/). In one embodiment, the RNA and/or cDNA coding sequences are designed for optimal expression in human cells.

Codon-optimized coding regions can be designed by various different methods. This optimization may be performed using methods which are available on-line (e.g., GeneArt), published methods, or a company which provides codon optimizing services, e.g., DNA2.0 (Menlo Park, CA). One codon optimizing algorithm is described, e.g., in US International Patent Publication No. WO 2015/012924, which is incorporated by reference herein. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

The immunoglobulin genes described herein may be used to express the "wild-type", a published or commercially available, or other known constant immunoglobulin domains or can be engineered to decrease affinity for, or ablate, binding to the Fc binding site present on immunoglobulins. There are several different types of Fc receptors, which are classified based on the type of antibody that they recognize. As used herein, "FcRn" refers to the neonatal Fc receptor that binds IgG. It is similar in structure to MHC class I protein. In humans, it is encoded by the FCGRT gene. The Fc receptor is located on various cells types, including, e.g., the epithelial cells of the blood brain barrier. The term "FcRn binding domain" as used herein refers to a protein domain that directly or indirectly binds to the FcRn. The FcRn may be a mammalian FcRn. In further embodiments, the FcRn is a human FcRn. An FcRn binding domain binding directly to an FcRn is an antibody Fc region. Meanwhile, regions capable of binding to a polypeptide such as albumin or IgG, which has human FcRn-binding activity, can indirectly bind to human FcRn via albumin, IgG, or such. Thus, such a human FcRn-binding region may be a region that binds to a polypeptide having human FcRn-binding activity. The term "Fc region" as used herein refers to an FcRn-binding domain that directly binds to FcRn, a mammalian FcRn, or a human FcRn. In particular, an Fc region is an Fc region of an antibody. The Fc region may be a mammalian Fc region or more particularly a human Fc region. In particular, the Fc region may be located within the second and third constant domain of a human immunoglobulin (CH2 and CH3). Further, the Fc region may be the hinge of CH2 and CH3. In one embodiment, the immunoglobulin construct is an IgG. In a further embodiment, the Fc region is an Fc region of human IgG1. Other Ig isotypes can be used as well.

Because these binding domains are located within the constant region of an IgG heavy chain (regions CH2 and CH3), the amino acid positions provided herein for modification in trastuzumab can be readily determined by preparing an alignment with another immunoglobulin heavy chain selected for modification in order to identify the corresponding amino acid number. Methods and computer programs for preparing such alignments are available and well known to those of skill in the art. The amino acid positions referred to in this application are based upon the numbering of trastuzumab as provided in SEQ ID NO: 3 and 25 (heavy chain) and SEQ ID NO: 4 (light chain). Substitutions may also be written as (amino acid identified by single letter code)-position #-(amino acid identified by single letter code) whereby the first amino acid is the substituted amino acid and the second amino acid is the substituting amino acid at the specified position. The terms "substitution" and "substitution of an amino acid" and "amino acid substitution" as used herein refer to a replacement of an amino acid in an amino acid sequence with another one, wherein the latter is different from the replaced amino acid. Methods for replacing an amino acid are well known to the skilled in the art and include, but are not limited to, mutations of the nucleotide sequence encoding the amino acid sequence. Methods of making amino acid substitutions in IgG are described, e.g., for WO 2013/046704, which is incorporated by reference for its discussion of amino acid modification techniques, although this document describes increasing FcRn affinity, rather than decreasing or ablating binding affinity as described herein.

The term "amino acid substitution" and its synonyms described above are intended to encompass modification of an amino acid sequence by replacement of an amino acid with another, substituting amino acid. The substitution may be a conservative substitution. The term conservative, in referring to two amino acids, is intended to mean that the amino acids share a common property recognized by one of skill in the art. The term non-conservative, in referring to two amino acids, is intended to mean that the amino acids which have differences in at least one property recognized by one of skill in the art. For example, such properties may include amino acids having hydrophobic nonacidic side chains, amino acids having hydrophobic side chains (which may be further differentiated as acidic or nonacidic), amino acids having aliphatic hydrophobic side chains, amino acids having aromatic hydrophobic side chains, amino acids with polar neutral side chains, amino acids with electrically charged side chains, amino acids with electrically charged acidic side chains, and amino acids with electrically charged basic side chains. Both naturally occurring and non-naturally occurring amino acids are known in the art and may be used as substituting amino acids in embodiments. Thus, a conservative amino acid substitution may involve changing a first amino acid having a hydrophobic side chain with a different amino acid having a hydrophobic side chain; whereas a non-conservative amino acid substitution may involve changing a first amino acid with an acidic hydrophobic side chain with a different amino acid having a different side chain, e.g., a basic hydrophobic side chain or a hydrophilic side chain Still other conservative or non-conservative changes change be determined by one of skill in the art.

In still other embodiments, the substitution at a given position will be to an amino acid, or one of a group of amino acids, that will be apparent to one of skill in the art in order to accomplish an objective identified herein.

In one embodiment, an immunoglobulin construct as defined herein is engineered so that the native sequence located on the conserved region of the immunoglobulin Fc region is ablated to eliminate binding to the FcRn and to minimize or eliminate transport of the proteinaceous immunoglobulin constructs across the blood brain barrier (out of the CNS area) and into the systemic circulation. In one example, this may be accomplished by altering one or more amino acids of the FcRn-binding domain, e.g., by modification of the codon for the selected amino acid(s).

For example, the immunoglobulin may be modified in one or more of the codons encoding the amino acid reside at position Y436 (aa459 of SEQ ID NO: 25), 5254 (aa277 of SEQ ID NO:25), 1253 (aa276 of SEQ ID NO: 25), and/or H435 (aa458 of SEQ ID NO: 25) to another suitable amino acid, e.g., alanine (Ala, A). However, other positions involved in functionally binding to FcRn may be mutated, such as, e.g., T250 (aa 273 of SEQ ID NO:25), M252 (aa 275 of SEQ ID NO: 25), S254 (aa 277 of SEQ ID NO: 25), T256 (aa 279 of SEQ ID NO: 25), P257 (aa 280 of SEQ ID NO: 25), P271 (aa 294 of SEQ ID NO:25), T307 (aa 330 of SEQ ID NO:25), Q311 (aa 334 of SEQ ID NO: 25), D376 (aa 399 of SEQ ID NO: 25), E380 (aa 403 of SEQ ID NO: 25), M428 (aa 451 of SEQ ID NO: 25), and/or N434 (aa 457 of SEQ ID NO: 25), or combinations one or more of these with each other, or with the other modifications described herein. Other suitable modifications may be located at 1253 (aa 276 of SEQ ID NO: 25), S254 (aa 277 of SEQ ID NO: 25), K288 (aa 311 of SEQ ID NO: 25), V305 (aa 328 of SEQ ID NO: 25), Q311 (aa 334 of SEQ ID NO: 25), D312 (aa 335 of SEQ ID NO: 25), K317 (aa 340 of SEQ ID NO: 340), K360 (aa 383 of SEQ ID NO: 25), Q362 (aa 385 of SEQ ID NO: 25), E380 (aa 403 of SEQ ID NO: 25), 5415 (aa 438 of SEQ ID NO: 25), 5424 (aa 447 of SEQ ID NO: 25), H433 (aa 456 of SEQ ID NO: 25), N434 (aa 457 of SEQ ID NO: 25), H435 (aa 458 of SEQ ID NO: 25), and/or Y436 (aa 459 of SEQ ID NO: 25), or combinations of two or more. As described above, corresponding locations in other IgG heavy chain CH2 and CH2 may be selected. Reference to "one or more" herein is intended to encompass the individual embodiments of, for example, 1, 2, 3, 4, 5. In additional embodiments, the term "one or more" includes a number of substitutions in a polypeptide described herein that would yield at least about 85% identity, at least 90% identity, at least about 95% identity, or at least about 99% identity to the trastuzumab heavy chain variable region SEQ ID NO: 3, light chain variable region SEQ ID NO:4, heavy chain SEQ ID NO: 25 or another amino acid sequence identified herein.

In addition, mutations that enhance complement-dependent cytotoxicity (CDC) and/or antibody-dependent cell-mediated cytotoxicity (ADCC) functions may be incorporated in the trastuzamab variants described herein. In further embodiments, such a mutation facilitates the killing of the tumor cells by immune cells. Examples of suitable amino acid modifications to enhance ADCC function are described in, e.g., US Patent Publication No. 2008/0118501; A Nasume, et al, Drug Des Devel Ther, 2009, 3; 7-16, publ online Sep. 21, 2009. G A Lazar et al, Proc Natl Acad Sci, vol. 103, no. 11, p. 4005-4010 (Mar. 14, 2006); and GL Moore, et al, MAbs, 2010 March-April; 2(2): 181-189, among others.

The heavy chain amino acid numbering used herein to identify the location of the mutants is based on the EU numbering system [IMGT unique numbering, Edelman, G. M. et al., Proc. Natl. Acad. USA, 63, 78-85 (1969); web site: imgt.org/IMGTScientificChart/-Numbering/Hu_IGHGnber.html]] and refer to positions in an FcRn-binding domain, in particular in an Fc region. In a similar fashion, substitutions are indicated as for example "EU387R" or "EU440E", wherein the number given after "EU" indicates the position of the substitution according the EU numbering, and the letter after the number is the substituted amino acid given in the one letter code. Other numbering systems include, e.g., Kabat, E. A., T. T. Wu, H. M. Perry, K. S. Gottesman, C. Foeler. (1991) Sequences of Proteins of Immunological Interest. No. 91-3242 U. S. Public Health Services, National Institutes of Health, Bethesda).

In one embodiment, an anti-Her2 antibody is selected for a composition and method as described herein. In one embodiment, the selected antibody is trastuzumab. The amino acid sequences of trastuzumab have been described, e.g., in P. Carter et al, Proc Natl Acad Sci., 89:4285-4289 (May 1982). The amino acid sequence of the trastuzumab heavy chain is provided in FIG. 1, showing both the sequence listing [SEQ ID NO: 25] and EU numbering systems. The amino acid sequence of the trastuzumab heavy chain variable region is shown in [SEQ ID NO: 3] and the trastuzumab light chain variable region is provided in the appended sequence listing [SEQ ID NO: 4]. In order to express trastuzumab, a novel nucleic acid molecule has been designed which contains codons which have been selected for optimal expression of the trastuzumab polypeptides in humans. Further, the novel nucleic acid molecule includes a heterologous leader sequence for each the heavy chain and light chain of trastuzumab, which encodes the IL-2 signal leader peptide fused upstream of the heavy and chain polypeptides composed of the variable and constant regions. However, another heterologous leader sequence may be substituted for one or both of the IL-2 signal/leader peptide. Signal/leader peptides may be the same or different for each the heavy chain and light chain immunoglobulin constructs. These may be signal sequences which are natively found in an immunoglobulin (e.g., IgG), or may be from a heterologous source. Such heterologous sources may be a cytokine (e.g., IL-2, IL12, IL18, or the like), insulin, albumin, β-glucuronidase, alkaline protease or the fibronectin secretory signal peptides, amongst others. The promoter(s) can be selected from different sources, e.g., human cytomegalovirus (CMV) immediate-early enhancer/promoter, the SV40 early enhancer/promoter, the JC polymovirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter.

The expression cassette described herein may contain at least one internal ribosome binding site, i.e., an IRES, located between the coding regions of the heavy and light chains. Alternatively the heavy and light chain may be separated by a furin-2a self-cleaving peptide linker [see, e.g., Radcliffe and Mitrophanous, Gene Therapy (2004), 11, 1673-1674. The expression cassette may contain at least one enhancer, i.e., CMV enhancer. Still other enhancer elements may include, e.g., an apolipoprotein enhancer, a zebrafish enhancer, a GFAP enhancer element, and brain specific enhancers such as described in WO 2013/1555222, woodchuck post hepatitis post-transcriptional regulatory element. Additionally, or alternatively, other, e.g., the hybrid human cytomegalovirus (HCMV)-immediate early (IE)-PDGR promoter or other promoter-enhancer elements may be selected. To enhance expression the other elements can be introns (like promega intron or chimeric chicken globin-human immunoglobulin intron).

As provided herein, with respect to the numbering of the engineered nucleic acid molecule in SEQ ID NO:1, a nucleic acid sequence encoding the heavy chain polypeptide of trastuzumab is characterized by the leader sequence (1-60 of SEQ ID NO:1), nucleic acids 61 to 423 are the coding region for the immunoglobulin heavy chain (HC) variable sequence, nucleic acids 439 to 714 are the coding region for the HC constant region 1, nucleic acids 715 to 1410 are the coding region for the HC constant regions 2 and 3. The IRES is located at nucleic acids 1422-2012 of SEQ ID NO: 1 between the trastuzumab heavy chain and the leader sequence of the trastuzumab light chain coding sequence. The variable region of the trastuzumab light chain variable sequence is at nucleotides 2070-2391 of SEQ ID NO: 1; the light chain constant region is located at nucleic acids 2407 to 2711 of SEQ ID NO:1.

Also encompassed herein are nucleic acid sequences encoding the trastuzumab immunoglobulin polypeptides [e.g., the heavy chain, the light chain, or fragments thereof, which fragments may include, e.g., complementarity determining regions (CDR) 1, 2 and/or 3, a constant region (1, 2, or 3) of SEQ ID NO:1, or a sequence which is at least about 85% identical thereto, at least about 90%, at least about 95% identical thereto, or at least about 99% identical thereto to SEQ ID NO: 1, or a fragment thereof coding for an immunoglobulin polypeptide (e.g., the heavy chain, the light chain, or fragments thereof [e.g., the heavy chain, the light chain, or fragments thereof (e.g., a variable region (including, e.g., complementarity determining regions (CDR) 1, 2 and/or 3), a constant region (1, 2, or 3))], which encode polypeptides and fragments thereof having the same amino acid sequence as provided herein for the trastuzumab without any FcRN modifications.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., any one of the modified ORFs provided herein when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Generally, these programs are used at default settings, although one skilled in the art can alter these settings as needed. Alternatively, one of skill in the art can utilize another algorithm or computer program that provides at least the level of identity or alignment as that provided by the referenced algorithms and programs. This definition also refers to, or can be applied to, the compliment of a sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of an amino acid or nucleic acid sequences.

Typically, when an alignment is prepared based upon an amino acid sequence, the alignment contains insertions and deletions which are so identified with respect to a reference AAV sequence and the numbering of the amino acid residues is based upon a reference scale provided for the alignment. However, any given AAV sequence may have fewer amino acid residues than the reference scale. In the present invention, when discussing the parental sequence, the term "the same position" or the "corresponding position" refers to the amino acid located at the same residue number in each of the sequences, with respect to the reference scale for the aligned sequences. However, when taken out of the alignment, each of the proteins may have these amino acids located at different residue numbers. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCK-MAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, *Nucl. Acids. Res.*, "A comprehensive comparison of multiple sequence alignments", 27(13):2682-2690 (1999).

In another embodiment, a modified anti-Her2 antibody having its affinity for FcRn ablated and retaining effective anti-neoplastic activity is provided. One or more amino acid modifications may be selected to ablate functional binding to FcRn. In one embodiment, the mutation lowers the binding affinity of the trastuzumab immunoglobulin for FcRn to less than 10% of the native protein. Suitably, the immunoglobulins with these mutations bind substantially normally to all other Fc receptors. For example, the immunoglobulin may be modified at least one of position Y436, S254, I253, and/or H435 to an alanine or other amino acid, or combinations of one or more of these with each other, or one, two or more with one or more of the modifications described herein. However, other positions involved in functional binding to FcRn may be mutated, such as, e.g., T250 (aa 273 of SEQ ID NO:25), M252 (aa 275 of SEQ ID NO: 25), S254 (aa 278 of SEQ ID NO: 25), T256 (aa 280 of SEQ ID NO: 25), P257 (aa 281 of SEQ ID NO: 25), P271 (aa 294 of SEQ ID NO:25), T307 (aa 330 of SEQ ID NO:25), Q311 (aa 334 of SEQ ID NO: 25), D376 (aa 399 of SEQ ID NO: 25), E380 (aa 403 of SEQ ID NO: 25), M428 (aa 451 of SEQ ID NO: 25), and/or N434 (aa 457 of SEQ ID NO: 25), or combinations one or more of these with each other, or with the other modifications described herein. Other suitable modifications may be located at I253 (aa 276 of SEQ ID NO: 25), S254 (aa 278 of SEQ ID NO: 25), K288 (aa 311 of SEQ ID NO: 25), V305 (aa 328 of SEQ ID NO: 25), Q311 (aa 334 of SEQ ID NO: 25), D312 (aa 335 of SEQ ID NO: 25), K317 (aa 340 of SEQ ID NO: 340), K360 (aa 383 of SEQ ID NO: 25), Q362 (aa 385 of SEQ ID NO: 25), E380 (aa 403 of SEQ ID NO: 25), S415 (aa 438 of SEQ ID NO: 25), S424 (aa 447 of SEQ ID NO: 25), H433 (aa 456 of SEQ ID NO: 25), N434 (aa 457 of SEQ ID NO: 25), H435 (aa 458 of SEQ ID NO: 25), and/or Y436 (aa 459 of SEQ ID NO: 25), or combinations of two or more, e.g., by substitution with another amino acid which retains the desired anti-neoplastic activity. Still other mutations may be incorporated. See, e.g., Kuo and Aveson, mAbs, 3:5, 422-430 (September/October 2011) and Shield, J Biol Chem, 2001, 276: 659-6604. Once the amino acid sequence is selected, the nucleic acid sequences can be designed and/or the previously described sequences may be engineered as described above. These modifications are made by engineering the nucleic acid coding region using site directed mutagenesis or other genetic engineering techniques which are known to those of skill in the art.

Similar modifications may be engineered into another selected anti-HER2 immunoglobulin construct, or alternately, into another anti-neoplastic immunoglobulin construct as described herein.

In one embodiment, the immunoglobulin genes described herein are engineered into a genetic element (e.g., a plasmid) useful for generating AAV vectors which transfer the immunoglobulin construct sequences carried thereon. The selected vector may be delivered to a an AAV packaging cell by any suitable method, including transfection, electroporation, liposome delivery, membrane fusion techniques, high velocity DNA-coated pellets, viral infection and protoplast fusion. Stable packaging cells can also be made. The methods used to make such constructs are known to those with skill in nucleic acid manipulation and include genetic engineering, recombinant engineering, and synthetic techniques. See, e.g., Molecular Cloning: A Laboratory Manual, ed. Green and Sambrook, Cold Spring Harbor Press, Cold Spring Harbor, NY (2012).

AAV Vectors

An AAV vector as described herein can comprise one or more nucleic acid sequences, each of which encodes one or more of the heavy and/or light chain polypeptides, or other polypeptides, of an anti-neoplastic immunoglobulin construct. Suitably, a composition contains one or more AAV vectors which contain all of the polypeptides which form an anti-neoplastic construct in vivo. For example, a full-length antibody consists of four polypeptides: two identical copies of a heavy (H) chain polypeptide and two copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. In this respect, an AAV vector as described herein can comprise a single nucleic acid sequence that encodes the two heavy chain polypeptides (e.g., constant variable) and the two light chain polypeptides of an immunoglobulin construct. Alternatively, the AAV vector can comprise a first expression cassette that encodes at least one heavy chain constant polypeptides and at least one heavy chain variable polypeptide, and a second expression cassettes that encodes both light chain polypeptides of an immunoglobulin construct. In yet another embodiment, the AAV vector can comprise a first expression cassette encoding a first heavy chain polypeptide, a second expression cassette encoding a second heavy chain polypeptide, a third expression cassette encoding a first light chain polypeptide, and a fourth expression cassette encoding a second light chain polypeptide.

Typically, an expression cassette for an AAV vector comprises an AAV 5' inverted terminal repeat (ITR), the immunoglobulin construct coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used.

Where a pseudotyped AAV is to be produced, the ITRs in the expression are selected from a source which differs from the AAV source of the capsid. For example, AAV2 ITRs may be selected for use with an AAV capsid having a particular efficiency for targeting CNS or tissues or cells within the CNS. In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. However, other sources of AAV ITRs may be utilized.

The abbreviation "sc" refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

The expression cassette typically contains a promoter sequence as part of the expression control sequences, e.g., located between the selected 5' ITR sequence and the immunoglobulin construct coding sequence. Tissue specific promoters, constitutive promoters, regulatable promoters [see, e.g., WO 2011/126808 and WO 2013/04943], or a promoter responsive to physiologic cues may be used may be utilized in the vectors described herein. In addition to a promoter, an expression cassette and/or a vector may contain other appropriate transcription initiation, termination, enhancer sequences, efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product.

These control sequences are "operably linked" to the immunoglobulin construct gene sequences. As used herein, the term "operably linked" refers to both expression control sequences that are contiguous with the gene of interest and expression control sequences that act in trans or at a distance to control the gene of interest.

In one embodiment, a self-complementary AAV is provided. This viral vector may contain a Δ5' ITR and an AAV 3' ITR. In another embodiment, a single-stranded AAV viral vector is provided. Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2]. In one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

The available space for packaging may be conserved by combining more than one transcription unit into a single expression cassette, thus reducing the amount of required regulatory sequences. For example, a single promoter may direct expression of a single cDNA or RNA that encodes two or three or more genes, and translation of the downstream genes are driven by IRES sequences. In another example, a single promoter may direct expression of a cDNA or RNA that contains, in a single open reading frame (ORF), two or three or more genes separated from one another by sequences encoding a self-cleavage peptide (e.g., 2A) and/or a protease recognition site (e.g., furin). The ORF thus encodes a single polyprotein, which, either during or after translation, is cleaved into the individual proteins (such as, e.g., heavy chain and light chain) It should be noted, however, that although these IRES and polyprotein systems can be used to save AAV packaging space, they can only be used for expression of components that can be driven by the same promoter. In another alternative, the transgene capacity of AAV can be increased by providing AAV ITRs of two genomes that can anneal to form head to tail concatamers.

In the examples below, an AAV9 vector is described for expressing trastuzumab directly in the CNS to treat breast cancer CNS metastases. AAV9 vectors are described, e.g., in U.S. Pat. No. 7,906,111, which is incorporated herein by reference. However, other sources of AAV capsids and other viral elements may be selected, as may other immunoglobulin constructs and other vector elements. Methods of generating AAV vectors have been described extensively in the literature and patent documents, including, e.g., WO 2003/042397; WO 2005/033321, WO 2006/110689; U.S. Pat. No. 7,588,772 B2. The source of AAV capsids may be selected from an AAV which targets CNS, specific cells within the CNS, and/or specific cancer-associated antigens or receptors. Suitable AAV may include, e.g, AAV9 [U.S. Pat. No. 7,906,111; US 2011-0236353-A1], rh10 [WO 2003/042397] and/or hu37 [see, e.g., U.S. Pat. No. 7,906,111; US 2011-0236353-A1]. However, other AAV, including, e.g., AAV1, AAV2, AAV3, AAV4, AAV5, AAV6, AAV7, AAV8 [U.S. Pat. Nos. 7,790,449; 7,282,199] and others such as, e.g., those described in a word seems to be missing here may be selected for preparing the AAV vectors described herein.

Uses and Regimens

Suitably, the composition of the invention are designed so that AAV vectors carry the nucleic acid expression cassettes encoding the immunoglobulin constructs and regulatory sequences which direct expression of the immunoglobulin thereof in the selected cell. Following administration of the vectors into the CNS, the vectors deliver the expression cassettes to the CNS and express the proteinaceous immunoglobulin constructs in vivo. The use of compositions described herein in an anti-neoplastic method are described, as are uses of these compositions in anti-neoplastic regimens, which may optionally involve delivery of one or more other anti-neoplastic or other active agents.

As stated above, a composition may contain a single type of AAV vector as described herein which contains the expression cassette for delivering the anti-neoplastic immunoglobulin construct in vivo. Alternatively, a composition may contain two or more different AAV vectors, each of which has packaged therein different expression cassettes. For example, the two or more different AAV may have different expression cassettes which express immunoglobulin polypeptides which assemble in vivo to form a single functional immunoglobulin construct. In another example, the two or more AAV may have different expression cassettes which express immunoglobulin polypeptides for different targets, e.g., two provide for two functional immunoglobulin constructs (e.g., an anti-Her2 immunoglobulin construct and a second anti-neoplastic immunoglobulin construct). In still another alternative, the two or more different AAV may express immunoglobulin constructs directed to the same target, wherein one of the immunoglobulin constructs has been modified to ablate FcRn binding and a second immunoglobulin construct which retains its ability or has enhanced ability to bind to FcRn. Such a composition may be useful to simultaneously provide antibodies with increased retention in the brain area and antibodies for systemic delivery of the immunoglobulin construct.

Optionally, one or both of these immunoglobulin constructs described herein has enhanced ADCC activity. A regimen as described herein may comprise, in addition to one or more of the combinations described herein, further combination with one or more of an anti-neoplastic biological drug, an anti-neoplastic small molecule drug, a chemotherapeutic agent, immune enhancers, radiation, surgery, and the like. A biological drug as described herein, is based on a peptide, polypeptide, protein, enzyme, nucleic acid molecule, vector (including viral vectors), or the like.

Suitably, the compositions described herein comprise an anti-neoplastic effective amount of one or more AAV suspended in a pharmaceutically suitable carrier designed for delivery to the subject via injection, osmotic pump, intrathecal catheter, or for delivery by another device or route. In one example, the composition is formulated for intrathecal delivery. As used herein, intrathecal delivery encompasses an injection into the spinal canal, more specifically into the subarachnoid space. However, other routes of delivery may be selected and the pharmaceutically acceptable carriers for the AAV compositions including, e.g., intracranial, intranasal, intracisternal, intracerebrospinal fluid delivery, among other suitable direct or systemic routes, i.e. Ommaya reservoir.

The compositions can be formulated in dosage units to contain an amount of AAV that is in the range of about $1 \times 10^9$ genome copies (GC) to about $5 \times 10^{13}$ GC (to treat an average subject of 70 kg in body weight). In one embodiment, a spinal tap is performed in which from about 15 mL (or less) to about 40 mL CSF is removed and in which vector is admixed with the CSF and/or suspended in a compatible carrier and delivered to the subject. In one example, the vector concentration is about $3 \times 10^{13}$ GC, but other amounts such as about $1 \times 10^9$ GC, about $5 \times 10^9$ GC, about $1 \times 10^{10}$ GC, about $5 \times 10^{10}$ GC, about $1 \times 10^{11}$ GC, about $5 \times 10^{11}$ GC, about $1 \times 10^{12}$ GC, about $5 \times 10^{12}$ GC, or about $1.0 \times 10^{13}$ GC.

The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, maltose, and water. The selection of the carrier is not a limitation of the present invention. Optionally, the compositions of the invention may contain, in addition to the rAAV and carrier(s), other conventional pharmaceutical ingredients, such as preservatives, or chemical stabilizers.

In one embodiment, the compositions described herein are used in a method for retarding the growth of a tumor. In still another embodiment, the compositions described herein are useful for decreasing tumor size in a subject. In a further embodiment, the compositions described herein are useful in reducing the number of cancer cells in a non-solid tumor cancer. In another embodiment, a composition as provided herein is used in a method for increasing overall survival and/or progression-free survival in a patient. For example, the data in the Examples below demonstrates a 33% increase in survival rate in metastatic breast cancer in brain as a solo therapy over the period tested. However, even more modest increases in survival rate would be desirable. The anti-neoplastic immunoglobulin constructs are selected with a view to the neoplasm to be treated. For example, for treatment of a metastatic breast cancer in the brain, one may engineer an expression cassette for an anti-HER antibody into a recombinant AAV as described herein. Optionally, the AAV compositions as described herein are administered in the absence of an additional extrinsic pharmacological or chemical agent, or other physical disruption of the blood brain barrier.

In a combination therapy, the AAV-delivered immunoglobulin construct described herein is administered before, during, or after commencing therapy with another agent, as well as any combination thereof, i.e., before and during, before and after, during and after, or before, during and after commencing the anti-neoplastic therapy. For example, the AAV can be administered between 1 and 30 days, preferably 3 and 20 days, more preferably between 5 and 12 days before commencing radiation therapy. In another embodiment of the invention, chemotherapy is administered concurrently with or, more preferably, subsequent to AAV-mediated immunoglobulin (antibody) therapy. In still other embodiments, the compositions of the invention may be combined with other biologics, e.g., recombinant monoclonal antibody drugs, antibody-drug conjugates, or the like. Further, combinations of different AAV-delivered immunoglobulin constructs such as are discussed above may be used in such regimens.

Any suitable method or route can be used to administer an AAV-containing composition as described herein, and optionally, to co-administer anti-neoplastic agents and/or antagonists of other receptors. The anti-neoplastic agent regimens utilized according to the invention, include any regimen believed to be optimally suitable for the treatment of the patient's neoplastic condition. Different malignancies can require use of specific antitumor antibodies and specific anti-neoplastic agents, which will be determined on a patient to patient basis. Routes of administration include, for example, systemic, oral, intravenous, intraperitoneal, subcutaneous, or intramuscular administration. The dose of antagonist administered depends on numerous factors, including, for example, the type of antagonists, the type and severity tumor being treated and the route of administration of the antagonists.

The following examples are illustrative only and are not a limitation on the invention described herein.

EXAMPLES

Example 1: CNS Expression of AAV9-Mediated Delivery of GFP

Both GFP and mAbs have been expressed in the CNS of cynomolgus macaques following intracisternal injection of AAV9 vectors containing a GFP transgene under either CMV or CB7 promoters at 5×10$^{12}$ genome copies (gc)/kg. After 14 days, macaques were necropsied and histology and biodistribution studies were performed. Post-necropsy histological analysis showed broad CNS expression of GFP in cerebrum, cerebellum, choroid plexus, meninges, and spinal cord ventral horn.

In addition, 3×10$^{12}$ gc/kg of AAV9 vector containing the 201 anti-SIV immunoadhesin (201IA) transgene under the control of the CB7 promoter was injected intracisternally and CSF was taken at regular intervals to measure the concentration of the immunoadesin. The resulting level of 201IA expressed in the CSF peaked at ~600 ng/mL, plateaued at ~250 ng/mL, and remained stable at 198 days post-injection.

A. 201IA Expression Construct

The codon-optimized nucleotide sequence for rhesus macaque anti-SIV mac251 gp120 IgG-201 (Glamann et al. J Virol. 1998; 74(15):7158-7163. doi:10.1128/JVI.74.15.7158-7163.2000.Updated) immunoadhesin (201IA) was cloned into an AAV expression construct. The construct was flanked by AAV2 inverted terminal repeats and contained a CB7 promoter, a chimeric intron, and a rabbit globin polyadenylation sequence (pAAV.CB7.CI.201IA.rBG).

B. I253A Mutation of 201IA to Abrogate FcRn Binding

A nucleotide sequence 768 bp in length complementary to the 201IA gene but containing a mutation corresponding to I253A [SEQ ID NO: 24 provides the CH2.CH3 fragment with this mutation] or H453A [SEQ ID NO: 23 provides the CH2.CH3 fragment with this mutation] of the heavy chain amino acid sequence (Kabat numbering) was obtained from GeneArt (Life Technologies). The sequence was flanked by Pst1 and BstZ17I restriction sites matching those in pAAV.CB7.CI.201IA.rBG. The mutated sequences were separately cloned into a pAAV.CB7.CI.201IA.rBG by restriction digest using the enzymes indicated (NEB) and ligation (TaKaRa Inc.) as described by the manufacturers. Sanger sequencing (GeneWiz) was used to confirm complementarity of pAAV.CB7.CI.201IA.rBG [SEQ ID NO: 5 (SEQ ID NO: 6 corresponds to encoded 201IA sequence)], pAAV.CB7.CI.201IA(I253A).rBG [SEQ ID NO: 7 (encoding SEQ ID NO:8)] and pAAV.CB7.CI.201IA(H435A).rBG [SEQ ID NO: 9 (encoding SEQ ID NO:10] on either side of the desired mutation.

B. IA Expression in HEK293 Cells and Purification by Protein A

3×10$^8$ HEK293 cells (293 cells) were seeded in a 10-stack CellSTACK® (Corning) in DuLbecco's Modified Eagle's Medium (DMEM, Corning CellGro) supplemented with 10% FBS and 1% penicillin/streptomycin (DMEM complete) and incubated at 37° C. 5% $CO_2$ for 48 hours. 1 mg of pAAV.CB7.CI.201IA.rBG or pAAV.CB7.CI.201IA (I253A).rBG in TE buffer (Qiagen) was diluted in 42 mL room-temperature antibiotic and serum-free DMEM. 2 mL PEI-Max 40 KDa, linear (Polysciences) at 1 mg/mL and pH 7.1 was diluted separately in 42 mL room-temperature antibiotic and serum-free DMEM. Diluted DNA and diluted PEI were combined and incubated for 15 minutes at room temperature. The DNA-PEI mixture was added to 1 L final volume of antibiotic and serum-free DMEM. 293T cells were washed twice with sterile PBS. The DNA-PEI DMEM mixture was added and incubated with the cells for 72 hours at 37° C. 5% $CO_2$. Supernatant was harvested and centrifuged for 10 minutes at 3000×g to pellet cellular debris. Supernatant was then concentrated using Centricon® Plus—70 Centrifugal Filter Units (EMD Millipore) according to manufacturer's instructions. 201IA or 201IA(I253A) was then purified using a Protein A Antibody Purification Kit (Sigma) and quantified using a NanoDrop 2000 (Thermo Scientific). The purified IAs were then diluted to 1 mg/mL using glycerol and stored at −20° C.

C. SDS-PAGE/Western Blot Analysis of IAs

SDS-PAGE using NuPage reagents (Life Technologies) was performed according to the manufacturer's instructions. Briefly, 1 µg 201IA, 201IA(I253A), or 201IA(H453A) was purified from 293 supernatant or 201IA previously purified in-house was mixed with NuPage Sample Buffer and NuPage Reducing Agent and heated at 70° C. for 10 minutes. Precast NuPage 4-12% Bis-Tris 1 mm acrylamide gels were loaded with samples and MagicMark XP Western Protein Standard (LifeTechnologies) and run in 1× NuPage MOPS SDS Running Buffer at 200V for 1 hour. The Trans-Blot® Turbo™ 1× transfer system (BioRad) was used to transfer proteins to LF PVDF membranes. Ion reservoir stacks were wetted with 1× Trans-Blot® Turbo™ (TBT) transfer buffer for 2-3 minutes. Pre-cut LF PVDF membranes were immersed in 100% ethanol until translucent, then transferred to 1×TBT buffer for 2-3 minutes. The transfer stack was assembled and run at 1.3 A and 25 V for 7 minutes. The LF PVDF membrane was blocked overnight with gentle shaking in 1×NET buffer+2% gelatin (50 mM Tris HCL pH 7, 125 mM NaCl, 5 mM EDTA pH 8, 0.05% Triton X-100, 2% gelatin in double distilled H2O). Goat anti-human IgG polyclonal antibody conjugated to biotin (Abcam) was diluted in 1×NET+2% gelatin and incubated with the membrane at room temperature, washed with 1×NET, incubated with streptavidin-horseradish peroxidase (Abcam) diluted in 1×NET+2% gelatin, and washed with 1×NET. The Western blot was detected using SuperSignal® West Pico Chemiluminescence Substrate (Thermo Scientific) according to the manufacturer's protocol. Images were captured using the BioRad ChemiDoc™ MP Image System (Thermo Scientific) with high resolution chemiluminescence automatic settings.

D. 201IA ELISA

All procedures were conducted at room temperature unless indicated otherwise. Plates were washed with BioTek 405TS microplate washer using PBS+0.05% Tween-20. mac251 gp120 (Immune Technology Corp.) diluted to 2 µg/mL in PBS was incubated overnight on Costar® 96-well EasyWash™ ELISA assay plates (Corning) at 4° C. Plates were then blocked 201IA ELISA blocking buffer (PBS+5% heat-inactivated fetal bovine serum+1 mM EDTA+0.07% Tween-20). Diluted samples were added to plates and diluted 2-fold down the plate at least four times. Plates were incubated for 1 h at 37° C. and blocked again in 201IA ELISA blocking buffer. Plates were then incubated with AffiniPure polyclonal goat anti-human IgG-biotin (Jackson ImmunoResearch Labs) diluted in PBS then with streptavidin-horseradish peroxidase (Abcam) diluted in PBS. 3,3',5,5'-tetramethylbenzidine (TMB) substrate was used to develop the plates. After stopping the colorimetric reaction with H2SO4, plates were read using a SpectraMax M3 (Molecular Devices) plate reader at 450 nm.

Equivalent performance of 201IA or 201IA (I253A), and performance of 201(H453) purified from 293 cells as described in these examples and a 201IA standard protein produced in-house was determined by 201IA ELISA. Each IA was diluted to 50 ng/mL and assayed as described above. The 201IA used as a standard was produced as follows. RAG KO mice were injected with an AAV8.TBG.201IA vector at $3\times10^{11}$ GC/per mouse intravenously, and orbital bleeds were collected on a weekly basis for 8 weeks, mice terminated by cardiac bleed. There are generally 5 mice per group. All collected serum is pooled together and loaded on the protein A affinity column from SIGMA as described above. Generally, purified 201IA is diluted to 1 mg/ml and glycerol added so that final glycerol is about 20% for better storage.

E. AAV9 Vector Production pAAV.CB7.CI.201IA.rBG and pAAV.CB7.CI.201IA (I253A).rBG were packaged in an AAV9 capsid by triple transfection of 293 cells and purified as previously described in M. Lock et al, Hum Gene Ther. 2010 October; 21(1); 1259-1271, published online 2010 Sep. 24.

F. Expression of 201IA and 201 IA(I253A) in Brain and Serum of Mice

All animals were maintained according to NIH and USDA guidelines for the care and use of animals in research. 6-8 week-old female Rag1−/− (Jackson Labs #002216), FcRn−/− Rag1−/− (Jackson Labs #017700), or human FcRn transgenic mice (mFcRn−/− hFcRn+/+, Jackson Labs #016919) on a C57BL/6 background were obtained and kept at the University of Pennsylvania.

For vector administration, AAV9.CB7.CI.201IA.rBG or AAV9.CB7.CI.201IA(I253A).rBG was diluted in sterile PBS. For intravenous (IV) administration, vector was diluted to $1\times10^{10}$ or $1\times10^{11}$ genome copies (GC) per 100 µL. For intracerebroventricular (ICV) administration, vector was diluted to $1\times10^{10}$ GC or $1\times10^{11}$ GC per 10 µL. IV injection was performed by tail-vein injection, and ICV injection was performed free-hand as described previously (Glascock et al. J Vis Exp. 2011 Oct. 3; (56)) after isofluorane induction of anesthesia. Blood was taken at days 3, 7, 14, 21, 28, 42, 56, and a final time point of day 60 for 201IA(I253A) or day 76 for 201IA by retro-orbital bleed into Z-Gel™ microtube serum separators (Sarstedt). Blood was incubated at room temperature for 20 minutes then centrifuged for 5 minutes at 5000×g. Serum was kept at −80° C. and used in the 201IA ELISA described above in Part D to measure serum 201IA concentration.

At necropsy, mice were deeply anesthetized with 100 mg/kg ketamine and 10 mg/kg xylazine in sterile PBS to a spinal plane of anesthesia. The thoracic cavity was exposed. A 20 gauge Angiocath™ Autoguard™ IV catheter (Becton Dickenson) was inserted into the left ventricle of the heart, and the right atrium was nicked with scissors. 50 mL PBS with Heparin (10 U/mL, Sigma) was administered into the left ventricle slowly through the IV catheter using a 30 mL hand-held syringe. Fluid exiting the right atrium was clear at the end of the perfusion procedure. Brain, liver, and spleen were removed and frozen immediately on dry ice. Brain tissue extract was prepared by quartering frozen mouse brains (~100 mg brain per quarter) and immersing them in 1 mL tissue lysis buffer (25 mM Tris-HCl, 5 mM EDTA, 1% Triton™-X, 150 mM NaCl, pH 7.6). Samples were homogenized with stainless-steal beads using a TissueLyzer™ (Qiagen) at 30 Hz for 2 minutes, frozen overnight at −80° C., thawed in a room-temperature water bath, and centrifuged at 10K×g for 10 minutes at 4° C. Supernatants from each of the four sections of an individual mouse brain were combined. After gentle vortexing, the brain extracts were aliquoted and frozen at −80° C. until use. Diluted brain extracts were used in the 201IA ELISA described above to determine 201IA expression in brain.

Serum expression of each the I253A and the H435A 201IA mutants was significantly lower than the wild-type 201IA (standard) after both iv or icy administration at both tested doses ($1\times10^{10}$ GC/mouse or $1\times10^{11}$ GC/mouse). The brain extracts tested after ICV administration ($1\times10^{11}$ GC/mouse) showed expression of the I253A mutant in the brain at levels exceeding those of the wild-type (standard). Expression of H435A ($1\times10^{11}$ GC/mouse) was observed.

G. Expression of 201IA and 201 IA(I253A) in CSF and Serum of Cynomolgus Macaques Four 3-4 year-old female cynomolgus macaques weighing between 3-5 kg were housed in stainless steel caging on a 12-hour light/dark cycle at the University of Pennsylvania according to according to NIH and USDA guidelines for the care and use of animals in research. Animals were acclimatized 7 weeks prior to initiation of studies. Monkeys were given Primate Diet 5049 (PMI Feeds Inc.). Water was given ad lib from an automatic watering system.

On the day of vector administration, animals were anesthetized using ketamine (10-15 mg/kg) and dexmedetomidine (0.05-0.10 mg/kg) given intramuscularly (IM). Animals were weighed, and vital signs were recorded. The hair over the back of the head and cervical spine was shaved. The skin was sterilely prepped with betadine. The neck was flexed so that the chin was almost touching the chest (care was taken not to occlude the animal's airway). The occipital protuberance at the back of the skull and the wings of the atlas (C1) were palpated and the spinal needle or regular needle (20-24 gauge) was inserted midway between them. If bone was encountered, the needle was redirected anteriorly or posteriorly. Once in the subarachnoid space, CSF was collected via gravitational flow into a syringe or other sterile container as it welled up into the hub of the needle (up to 2 mL). Suction was not applied to the needle. Up to 2 mL of vector solution was injected using a syringe pump at 0.5 mL/minute or manually at a slow steady pace. The needle was removed and direct pressure applied to the puncture site. Two macaques received AAV9.CB7.CI.201IA.rBG.N401 and two received AAV9.CB7.CI.201IA(I253A).rBG. The dose was $1.00 \times 10^{12}$ VG per kilogram of body weight.

At least once every two weeks, animals were monitored for vital signs, clinical pathology, and immunology. Blood and lumbar CSF were collected at day 8 and 15 after the procedure, then monthly. Serum and CSF was stored at approximately −65 to −80° C. 201IA expression was evaluated by 201IA ELISA as indicated above. Changes in the blood chemistries and blood profiles of the animals were monitored by the contract facility Antech Diagnostics, Inc.

Monkeys will be euthanized at the end of their study period. The animals are first sedated with ketamine (10-15 mg/kg) and dexmedetomidine (0.05-0.10 mg/kg) IM. They are euthanized using sodium pentobarbital (80 mg/kg IV). Death is confirmed by absence of heartbeat and respiration. The animal may also be exsanguinated to assure death. Collected tissues will be placed in 10% neutral buffered formalin for histopathology. For genome copy analysis, tissue samples will be immediately frozen on dry ice and maintained at <−60° C. Samples will be directly frozen in OCT embedding medium for cryosectioning. Slides will be prepared by Cellular and Morphology Core of the Gene Therapy Program of the University of Pennsylvania. Other appropriate stains may be employed at the discretion of the study pathologist.

Example 2: Production of AAV9 Expressing Trastuzumab

A well-published murine xenograft model of breast cancer brain metastasis is used to determine if trastuzumab expressed in the CNS prolongs survival or alleviates tumor burden [Martinez-Aranda A, et al, Development of a Preclinical Therapeutic Model of Human Brain Metastasis with Chemoradiotherapy. Int J Mol Sci. 2013; 14:8306-8327]. HER2 positive human BT474 ductal carcinoma cells are transfected with luciferase and injected stereotactically into the brain parenchyma of nude mice. Tumor size will be monitored by luminescent intensity. When the tumors grow to 10 mm², the mice will be injected intraventricularly with varying concentrations of AAV9 vector carrying a trastuzumab transgene.

The transgene is created by cloning the codon-optimized nucleic acid sequences now provided in SEQ ID NO: 1, which encode the published sequences of the light and heavy variable chains of trastuzumab, into an IgG expression cassette. The constant region amino acid sequences described in WO 2015/012924, which is incorporated by reference herein, can be used. See, e.g., Carter P, et al, Humanization of an anti-p185HER2 antibody for human cancer therapy. Proc Natl Acad Sci USA. 1992 May 15; 89(10):4285-9 describing humanization of the murine mAb precursor of trastuzumab. These amino acid sequences exactly match those of the clinical product sequenced by mass spectrometry in 2013 [Gahoual R, et al, Rapid and multi-level characterization of trastuzumab using sheathless capillary electrophoresis-tandem mass spectrometry. MAbs. 2013 Apr. 5; 5(3). [Epub ahead of print]. After injection of the vector, tumor size and mouse survival will be monitored for 30 days. At necropsy pathological examination of the tumor will be conducted and level of trastuzumab expression by ELISA of brain extracts determined. The vector and method described herein should provide prolonged survival, progression-free survival, and/or regression and/or stabilization of tumor burden.

A. Trastuzumab Expression Construct

Sequences matching the WHO published sequences of the heavy and light chains of trastuzumab were obtained from GeneArt (Life Technologies). The light chain sequence was flanked by EcoRV and BsiW1 restriction sites, and the heavy chain sequence was flanked by Xba1 and Sal1 restriction sites [the nucleic acid sequence is provided in SEQ ID NO: 11, which encodes trastuzumab heavy chain variable (SEQ ID NO: 12), heavy chain constant (SEQ ID NO: 13), light chain variable (SEQ ID NO: 14), kappa chain (SEQ ID NO: 15), and Amp-R (SEQ ID NO: 16)] provides the sequences of the plasmids containing the trastuzumab heavy and light chains.

The heavy and light chain sequences were cloned into an AAV expression construct using restriction digest (NEB) and ligation (TaKaRa Inc.) using known cloning techniques. The heavy and light chain sequences were separated from each other by an F2A self-cleaving peptide. The construct was flanked by AAV2 inverted terminal repeats and contained a CMV immediate early promoter, a chimeric intron, and a SV40 polyadenylation signal, termed pAAV.CMV.CI.trastuzumab.SV40 [SEQ ID NO: 17, encoding trastuzumab heavy chain variable, heavy chain constant, light chain variable, kappa chain (SEQ ID NO: 18-21, respectively)].

B. Trastuzumab Expression in HEK293 Cells and Purification by Protein A $3 \times 10^8$ HEK293 cells [obtained from the ATCC] were seeded in a 10-stack CellSTACK® in DMEM complete at 37° C. 5% $CO_2$ for 48 hours. 1 mg of pAAV.CMV.CI.trastuzumab.SV40 (described in Part A) was diluted in 42 mL room-temperature antibiotic and serum-free DMEM. 2 mL PEI-Max 40 KDa, linear (Polysciences) at 1 mg/mL and pH 7.1 was diluted separately in 42 mL room-temperature antibiotic and serum-free DMEM. Diluted DNA and diluted PEI were combined and incubated for 15 minutes at room temperature. The DNA-PEI mixture was added to a 1 L final volume of antibiotic and serum-free DMEM. 293 cells were washed twice sterile PBS, and the cells were then incubated with the DNA-PEI DMEM mixture for 72 hours. Supernatant was harvested, centrifuged for 10 minutes at 3000×g to pellet cellular debris, and concentrated using Centricon® Plus—70 Centrifugal Filter Units (EMD Millipore) according to manufacturer's instructions. Trastuzumab was then purified using a Protein A Antibody Purification Kit (Sigma) and quantified using a NanoDrop 2000 (Thermo Scientific). The purified trastuzumab was diluted to 1 mg/mL using glycerol and stored at −20° C.

C. SDS-PAGE/Western Blot Analysis of IAs

SDS-PAGE using NuPage reagents (Life Technologies) was performed according to the manufacturer's instructions. Briefly, 1 μg trastuzumab purified from 293 supernatant as described in Part B of this Example or trastuzumab clinical product resuspended in PBS (Hoffmann-La Roche, HUP Pharmacy), was mixed with NuPage Sample Buffer and NuPage Reducing Agent and heated at 70° C. for 10 minutes. Precast NuPAGE® 4-12% gradient Bis-Tris (neutral pH) 1 mm acrylamide gels were loaded with samples and MagicMark™ XP Western Protein Standard (LifeTechnologies) and run in 1× NuPage® 3-morpholinopropane-1-sulfonic acid (MOPS) SDS Running Buffer at 200V for 1 hour. The Trans-Blot® Turbo™ 1× transfer system (BioRad)

was used to transfer proteins to low fluorescence (LF) polyvinylidene fluoride (PVDF) membranes. Ion reservoir stacks were wetted with 1× Trans-Blot® Turbo™ (TBT) transfer buffer for 2-3 minutes. Pre-cut LF PVDF membranes were immersed in 100% ethanol until translucent, then transferred to 1×TBT buffer for 2-3 minutes. The transfer stack was assembled and run at 1.3 A and 25 V for 7 minutes. The LF PVDF membrane was blocked overnight with gentle shaking in 1×NET buffer+2% gelatin (50 mM Tris HCl pH 7, 125 mM NaCl, 5 mM ethylenediaminetetraacetic acid (EDTA) pH 8, 0.05% Triton™ X-100 (Triton™ X-100 is a nonionic surfactant that has a hydrophilic polyethylene oxide chain and an aromatic hydrocarbon lipophilic or hydrophobic group), 2% gelatin in double distilled H2O). Goat anti-human IgG polyclonal antibody conjugated to biotin (Abcam) was diluted in 1×NET+2% gelatin and incubated with the membrane at room temperature, washed with 1×NET, incubated with streptavidin-horseradish peroxidase (Abcam) diluted in 1×NET+2% gelatin, and washed with 1×NET. The Western blot was detected using SuperSignal® West Pico Chemiluminescence Substrate (Thermo Scientific) according to the manufacturer's protocol. Images were captured using the BioRad ChemiDoc™ MP Image System (Thermo Scientific) with high resolution chemiluminescence automatic settings.

D. Vector Production pAAV.CMV.CI.trastuzumab.SV40 was packaged in an AAV9 capsid by triple transfection of 293 cells and purified as previously described (Lock et al, 2010, cited above).

E. Trastuzumab ELISA

A trastuzumab mimotope ELISA was developed as described previously (Jiang et al. J Biol Chem. 2005 Feb. 11; 280(6):4656-62. Epub 2004 Nov. 9). All steps were performed at room temperature unless otherwise stated. Plates were washed with a BioTek 405TS microplate washer. A peptide mimotope of the epitope of HER2 to which trastuzumab binds, LLGPYELWELSH [SEQ ID NO: 22], was obtained from the mimotopes, resuspended in DMSO, and stored at −80° C. Costar® 96-well EasyWash™ ELISA assay plates (Corning) were coated at 1 µg/mL LLGPYELWELSH [SEQ ID NO: 22] in 100 mM bicarbonate solution (pH 9.6), incubated overnight at 4° C., and blocked with trastuzumab ELISA blocking buffer (TEB, PBS+5% bovine serum albumin+1 mM EDTA+0.07% Tween-20). Samples were diluted in TEB and plated, diluted 2-fold down the ELISA plate in TEB, and incubated. Plates were then incubated with AffiniPure polyclonal goat anti-human IgG-biotin (Jackson ImmunoResearch Labs) diluted in TEB followed by streptavidin-horseradish peroxidase (Abcam) diluted in TEB. Plates were developed with TMB substrate, stopped with 2N H2SO4, then read using a SpectraMax M3 (Molecular Devices) plate reader at 450 nm.

F. Expression of 201IA and 201 IA(1253A) in Brain and Serum of Mice 6-8 week-old female Rag1−/− mice (Jackson Labs #002216) on a C57BL/6 background were obtained and kept at the University of Pennsylvania and maintained according to NIH and USDA guidelines for the care and use of animals in research.

For vector administration, pAAV.CMV.CI.trastuzumab.SV40 was diluted in sterile PBS. For intravenous (IV) administration, vector was diluted to $1\times10^{10}$ or $1\times10^{11}$ GG per 100 µL. For intracerebroventricular (ICV) administration, vector was diluted to $1\times10^{10}$ or $1\times10^{11}$ GC per 10 µL. IV injection was performed by tail-vein injection, and ICV injection was performed free-hand after isofluorane induction of anesthesia as described previously (Glascock et al.).

Blood was taken at days 3, 7, 14, 21, 28, 42, 56, and 60 post-vector administration by retro-orbital bleed into Z-Gel microtube serum separators (Sarstedt). Blood was incubated at room temperature for 20 minutes then centrifuged for 5 minutes at 5000×g. Serum was kept at −80° C. and used in the trastuzumab ELISA described above to measure serum trastuzumab concentration.

At necropsy, mice were deeply anesthetized with 100 mg/kg ketamine and 10 mg/kg xylazine in sterile PBS to a spinal plane of anesthesia. The thoracic cavity was exposed. A 20 gauge Angiocath™ Autoguard™ IV catheter (Becton Dickenson) was inserted into the left ventricle of the heart, and the right atrium was nicked with scissors. 50 mL PBS with Heparin (10 U/mL, Sigma) was administered into the left ventricle slowly through the IV catheter using a 30 mL hand-held syringe. Fluid exiting the right atrium was clear at the end of the perfusion procedure. Brain, liver, and spleen were removed and frozen immediately on dry ice.

Brain tissue extract was prepared by quartering frozen mouse brains (~100 mg brain per quarter) and immersing them in 1 mL tissue lysis buffer (25 mM Tris-HCl, 5 mM EDTA, 1% Triton-X, 150 mM NaCl, pH 7.6). Samples were homogenized with stainless-steal beads on a TissueLyzer (Qiagen) at 30 Hz for 2 minutes, frozen overnight at −80° C., thawed in a room-temperature water bath, and centrifuged at 10K×g for 10 minutes at 4 C. Supernatants from each of the four sections of a single mouse brain were combined. After gentle vortexing, the brain extract was aliquotted and frozen at −80° C. until use. Diluted brain extracts were used in the trastuzumab ELISA above to measure brain trastuzumab concentration.

These data show the steady state expression levels of >1000 µg/mL in the serum of Rag1−/− mice following intravenous vector delivery for the duration of the experiment (60 days). For the mice receiving ICV vector administration, the steady state expression level of >750 µg/mL is observed for the duration of the experiment (60 days). These amounts are believed to demonstrate expression of levels which will provide a therapeutic effect.

The brain studies revealed concentrations of between about 1200 to about 1800 µg trastuzumab in the test mice for those receiving $1\times10^{10}$ and $1\times10^{11}$ intravenous vector. There did not appear to be any significant difference between these dosage levels for iv delivery. At the same doses, greater variation was observed for the vectors delivered at these concentrations via ICV. The concentrations varied from about 1000 µg to about 2500 µg.

G. Generation of HER2+BT474-M1 Breast Cancer Cell Line Expressing Firefly Luciferase HER2+BT474.M1 human ductal carcinoma cells at passage 27 were a generous gift from Louis Chodosh and Jason Ruth. [BT474.MI cells is a subclone of BT474 that can be obtained from California Pacific Medical Center; Si Tuen Lee-Hoeflich, et al., Cancer Res Jul. 15, 2008 68; 5878.] Cells were grown in a T75 tissue culture flask (Corning) in DMEM/F12 media (Corning Cellgro) supplemented with 10% FBS and 1% penicillin/streptomycin (DMEM/F12 complete). VSVG.HIV.SIN.cPPT.CMV.ff-luciferase.WPRE lentiviral vector was obtained from the Penn Vector Core [E. Coprini et al, Viruses, August 2010, 2(8): 1577-1588.] When BT474-M1 cells were 60-70% confluent, media was aspirated, cells were washed with sterile PBS, trypsinized, and counted. $2.5\times10^5$ cells in 2 mL DMEM/F12 complete were added to the wells of a six-well tissue culture treated plate (Falcon) and incubated overnight at 37° C. 5% $CO_2$. Vector was diluted in antibiotic and serum free DMEM/F12 to $3.5\times10^8$ VG/mL, and five 2-fold serial dilutions were prepared. 1 mL of the six vector dilutions were added to corresponding wells of the 6-well plate containing PBS-washed BT474-M1 cells and 1 mL antibiotic and serum-free DMEM/F12. The plate was incubated for 48 hours at 37° C. 5% $CO_2$. Media was aspirated and replaced with DMEM/F12 complete. No cytopathology was noted by microscopy. After another 72 hours, the cells in the 3 wells that received the highest concentration of vector were washed with sterile PBS, trypsinized, mixed, and cultured in a T75 flask in DMEM/F12 complete. After 72 hours at 37° C. 5% $CO_2$, cells were trypsinized and diluted to a concentration of 1 cell per 200 μL DMEM/F12 complete. 200 μL cell suspension per well was plated in a 96-well tissue culture-treated plate (Falcon) and incubated at 37° C. 5% $CO_2$ for 6 weeks. Media was changed every 2 weeks. Two weeks after plating, wells with single colonies of clonal cells were noted by microscopy. When wells were 70% confluent with a single cluster of clonal cells, fifteen clones were selected for further expansion to 70-80% confluency in 24-well plates, then in 6-well plates, then T25 tissue culture flasks (Corning). Morphology of the cells was compared with the parental BT474.M1 cell line and noted to be equivalent.

Luciferase activity of the cells was measured using the Dual Luciferase® Reporter Assay System (Promega) to the manufacturer's instructions. DNA was isolated from cells using the DNeasy Kit (Qiagen). Copy number of luciferase per cell in the five clones with the highest luminescence was determined by TaqMan Real Time PCR (Life Technologies) using the lentiviral packaging signal as a probe [A Hachiya et al, Gene Ther, April 2007; 14(8): 648-656, Epub 2007 Feb. 1]. The clone chosen for xenograft experiments was expanded to passage number 52 and cryopreserved in liquid nitrogen in DMEM/F12 with 5% DMSO and 20% FBS.

H. Xenograft Model of HER2+ Breast Cancer Brain Metastases in Rag1−/− Mice

BT474-M1.ffluc cells prepared as described in Part G of this example were thawed, washed in DMEM/F12 complete, expanded in T175 flasks (Corning) at 37° C. 5% $CO_2$ in DMEM/F12 complete, and passaged once at least 1 week before tumor cell implantation. On the day of injection, cells at passage 53 were trypsinized at 70%-80% confluency and counted using a hemacytometer. Cells were centrifuged for 3 minutes at 1000×g and washed with sterile PBS. After centrifuging again, cells were resuspended at $1\times10^5$ cells/1 μL in sterile PBS and kept on ice until injection. For the tumor cell injection procedure, mice were anesthetized by intraperitoneal (IP) injection of 100 mg/kg ketamine and 10 mg/kg xylazine in sterile PBS to induce a spinal plane of anesthesia. Opthalmic ointment was applied to the eyes of the mice ad lib. Hair was sheared from the top of the mouse's head using electric clippers. Estrogen pellets (1.6 mg, 60-day release) were implanted subcutaneously by cleansing the exposed skin first with povidone iodine then 70% ethanol. A small incision in the skin overlaying the thoracic spine was made, and the skin and underlying fascia were bluntly dissected. The estrogen pellet was implanted subcutaneously, and the incision was sutured with 4.0 vicryl. Next, the mice were then fixed in a stereotactic apparatus. The exposed skin over the skull was cleaned with povidone iodine followed by 70% ethanol. An anterior-posterior incision approximately 1 cm long was made over the top of the skull with a 22 scalpel blade. Bregma was identified. A pneumatic drill was positioned at bregma and coordinates were noted. The drill point was moved −0.8 mm anterior-posterior, +2.2 mm mediolateral of bregma, and a burr hole was drilled until brain parenchyma was reached. The drill was removed from the stereotactic apparatus, and a 10 μL Hamilton syringe was loaded with 1 μL of cell suspension. The needle was positioned on the apparatus, brought to bregma, and moved to the coordinates indicated above. The needle was checked for exact positioning over the burr hole, and coordinates were adjusted accordingly before penetrating −4.0 mm DV of bregma, then +1.0 mm 1 μL of cell suspension was injected over 5 minutes. The needle was left in place for 5 minutes after injection, then removed slowly. The mouse was removed from the stereotactic apparatus, and 4.0 vicryl was used to suture the incision over the skull. Mice were placed in a clean cage on top of a heating pad set to 37° C. After recovering from anesthesia, the mice were given 100 μL of 15 mg/kg enrofloxacin (Bayer) in sterile PBS along with 0.3 mg/kg buprenorphine in sterile PBS subcutaneously. Mice received enrofloxacin subcutaneously for two days after the procedure.

Growth of tumor was monitored every 3-4 days using bioluminescent imaging (BLI). Mice were injected IP first with 150 mg/kg luciferin in sterile PBS then with 100 mg/kg ketamine and 10 mg/kg xylazine in PBS five minutes later. 5-10 minutes after anesthesia was administered, mice were imaged using an IVIS Xenogen imaging system. Bioluminescence was measured for at least 5 seconds. Regions of interest (ROI) corresponding to luminescent tumors were measured by drawing a gate around the ROI. Luminescence was reported in photons/second. At necropsy, mice were euthanized by overexposure to CO2 followed by cervical dislocation. Brains were removed and preserved in formalin followed by 70% ethanol and embedded in paraffin for sectioning. Hematoxylin and eosin as well as luciferin immunostaining was performed. Liver and spleen were also taken at necropsy for biodistribution analysis of vector genomes.

I. Prophylactic Treatment of Xenograft Model of Breast Cancer Brain Metastases 6-8 week-old female Rag1−/− mice (Jackson Labs #002216) were treated 21 days prior to tumor implantation with an ICV injection of $1\times10^{11}$ VG of AAV9.CMV.CI.trastuzumab.SV40 (n=9), AAV9.CB7.CI.201IA.rBG (n=10), or no treatment (n=5). Tumors were implanted and bioluminescence was measured as indicated above. Blood was taken retro-orbitally from mice on D20, 36, 62, and 72 post vector injection to measure serum trastuzumab as a surrogate for CNS trastuzumab expression. After reaching a tumor BLI of $1\times10^8$ photons/second, mice are monitored daily and sacrificed at a clinical endpoint defined as neurological impairment or significant morbidity including lethargy, hunching, paralysis, neurological deficits, or seizures.

FIG. 2 provides a survival curve of mice given $1\times10^{11}$ GC ICV of AAV9.trastuzumab or AAV9.201IA prophylactically, then implanted with BT474-M1.ffluc tumor cells in the brain 21 days after vector administration. This curve reflects results 99 days post-tumor implantation. The median survival of 201IA group (sham treatment) is shown to be 66 days, whereas the median survival of the group treated with AAV9.trastuzumab is 99 days, a 33% increase in survival rate.

The biodistribution of the AAV9.trastuzumab as delivered iv and icy in Rag1−/− mice was assessed. At a dose of $1\times10^{10}$ GC for both iv and icy-delivered vectors, relatively low levels of vector genomes are observed in either liver or brain. At the higher dose ($1\times10^{11}$ GC), significantly higher levels of vectors are found in liver for both delivery methods, whereas significantly higher levels in brain are found only in the animals receiving icy administration. It is notable that this vector contained a non-tissue specific promoter.

Safety concerns may be reduced via use of a tissue specific promoter which specifically targets cells of the brain and optionally other neural cells or cells in the central nervous system, in order to minimize expression in liver. Alternatively, expression in liver may be beneficial for the systemic delivery of trastuzumab in order to prevent or control breast cancer metastasis into other organs.

J. Alternative Mouse Model Suitable for Studies of BT474-M1 Breast Cancer Brain Metastases Using NSG Mice 6-8 week-old female NSG mice (Jackson Labs #005557) were kept at the University of Pennsylvania. Tumors were implanted as indicated above with the following changes to the preparation of tumor cells and injection technique. Tumor cells were resuspended in 50% MatriGel® (Corning)/50% sterile PBS at $1 \times 10^5$ cells per 5 µL. Injection volume was increased from 1 µL to 5 µL. After positioning the needle in the brain parenchyma, 5 minutes elapsed before injection began. The injection was performed slowly over 10 minutes, and the syringe was left in place 5 minutes before removal. Mice were monitored and bioluminescence was measured as indicated elsewhere in this document. The data showed successful engraftment of the tumor cells into brain. The rates of the tumor growth will be evaluated to determine if this model is desirable for study of breast cancer metastasis to brain.

Sequence Listing Free Text

The following information is provided for sequences containing free text under numeric identifier <223>.

| SEQ ID NO: (containing free text) | Free text under <223> |
|---|---|
| 1 | <223> engineered anti-HER antibody<br><220><br><221> misc<br><222> (1) . . . (60)<br><223> IL2 signal/leader peptide<br><220><br><221> CDS<br><222> (61) . . . (423)<br><223> heavy variable<br><220><br><221> Misc<br><222> (439) . . . (714)<br><223> CH1<br><220><br><221> Misc<br><222> (715) . . . (1410)<br><223> CH1<br><220><br><221> Misc<br><222> (2010) . . . (2069)<br><223> IL2 signal/leader peptide<br><220><br><221> Misc<br><222> (2070) . . . (2391)<br><223> variable light<br><220><br><221> Misc<br><222> (2407) . . . (2711)<br><223> light chain constant region |
| 2 | <223> Synthetic Construct |
| 3 | <223> engineered anti-HER heavy chain<br><220><br><221> MISC_FEATURE<br><222> (1) . . . (20)<br><223> heavy chain signal peptide<br><220><br><221> MISC_FEATURE<br><222> (21) . . . (140)<br><223> heavy chain variable region<br><220><br><221> MISC_FEATURE<br><222> (141) . . . (259)<br><223> heavy chain constant region 1<br><220><br><221> MISC_FEATURE<br><222> (260) . . . (470)<br><223> heavy chain FC |
| 4 | <223> Engineered anti-Her2 light chain<br><220><br><221> MISC_FEATURE<br><222> (1) . . . (20)<br><223> signal sequence<br><220><br><221> MISC_FEATURE<br><222> (21) . . . (130)<br><223> light chain variable region<br><220><br><221> MISC_FEATURE<br><222> (131) . . . (214)<br><223> light chain constant region |
| 5 | <223> pAAV.CB7.CI.201IA.rBG<br><220><br><221> misc_feature<br><222> (275) . . . (404)<br><223> 3' ITR (complement)<br><220><br><221> misc_feature<br><222> (3226) . . . (3355)<br><223> 5' ITR<br><220><br><221> misc<br><222> (3423) . . . (3804)<br><223> CMV IE promoter<br><220><br><221> CDS<br><222> (5161) . . . (6690)<br><223> 201IA |
| 6 | <223> Synthetic Construct |
| 7 | <223> Plasmid encoding 201IA(I253A)mutant<br><220><br><221> misc<br><222> (1) . . . (130)<br><223> 5' ITR<br><220><br><221> misc_feature<br><222> (198) . . . (579)<br><223> CMV IE promoter<br><220><br><221> promoter<br><222> (582) . . . (863)<br><223> CB promoter<br><220><br><221> Intron<br><222> (958) . . . (1930)<br><223> chicken beta-actin intron<br><220><br><221> CDS<br><222> (1936) . . . (3465)<br><223> CMV IE promoter<br><220><br><221> polyA_signal<br><222> (3529) . . . (3655)<br><223> rabbit globin polyA<br><220><br><221> misc_feature<br><222> (3744) . . . (3873)<br><223> 3' ITR (complement) |

| SEQ ID NO: (containing free text) | Free text under <223> |
|---|---|
| | <220><br><221> misc_feature<br><222> (4636) ... (5493)<br><223> AP(R) marker |
| 8 | <223> Synthetic Construct |
| 9 | <223> engineered plasmid containing 201IA(H435) mutant<br><220><br><221> misc_feature<br><222> (275) ... (404)<br><223> 3' ITR (complement)<br><220><br><221> misc_feature<br><222> (3423) ... (3804)<br><223> CMV IE promoter<br><220><br><221> promoter<br><222> (3807) ... (4088)<br><223> CB promoter<br><220><br><221> TATA_signal<br><222> (4061) ... (4064)<br><223> rabbit globin polyA<br><220><br><221> Intron<br><222> (4183) ... (5155)<br><223> chicken beta-actin intron<br><220><br><221> CDS<br><222> (5161) ... (6690)<br><223> CMV IE promoter |
| 10 | <223> Synthetic Construct |
| 11 | <223> Plasmid containing the heavy and light chains of trastuzumab<br><220><br><221> misc_feature<br><222> (1) ... (130)<br><223> 5' ITR<br><220><br><221> promoter<br><222> (191) ... (932)<br><223> human CMV IE enhancer and promoter<br><220><br><221> sig_peptide<br><222> (1305) ... (1364)<br><223> IL-2 signal peptide<br><220><br><221> CDS<br><222> (1365) ... (1724)<br><223> Trastuzamab heavy variable<br><220><br><221> CDS<br><222> (1725) ... (2720)<br><223> trastuzumab heavy constant<br><220><br><221> enhancer<br><222> (2726) ... (3313)<br><223> IRES<br><220><br><221> sig_peptide<br><222> (3314) ... (3373)<br><223> IL2 signal peptide<br><220><br><221> CDS<br><222> (3374) ... (3694)<br><223> trastuzumab light variable<br><223> trastuzumab constant light (kappa)<br><220><br><221> polyA_signal<br><222> (4038) ... (4269)<br><223> SV40 late polyA signal<br><220><br><221> polyA_signal<br><222> (4083) ... (4269)<br><223> SV40 late polyA signal |

| SEQ ID NO: (containing free text) | Free text under <223> |
|---|---|
| | <220><br><221> misc_feature<br><222> (4334) ... (4463)<br><223> 3' ITR (complement)<br><220><br><221> rep_origin<br><222> (4640) ... (5095))<br><220><br><221> CDS<br><222> (5226) ... (6083)<br><223> amp-R<br><220><br><221> misc_feature<br><222> (6257) ... (6845)<br><223> COL/E1/origin |
| 12 | <223> Synthetic Construct |
| 13 | <223> Synthetic Construct |
| 14 | <223> Synthetic Construct |
| 15 | <223> Synthetic Construct |
| 16 | <223> Synthetic Construct |
| 17 | 223> Engineered plasmid containing trastuzumab MAb<br><220><br><221> sig_peptide<br><222> (1254) ... (1313)<br><223> IL2 signal sequence<br><220><br><221> CDS<br><222> (1314) ... (1673)<br><223> Trastuzamab heavy variable<br><220><br><221> CDS<br><222> (1674) ... (2660)<br><223> Trastuzamab heavy constant<br><220><br><221> sig_peptide<br><222> (2745) ... (2804)<br><223> IL2 signal sequence<br><220><br><221> CDS<br><222> (2805) ... (3110)<br><223> Trastuzamab light variable<br><220><br><221> CDS<br><222> (3111) ... (3452)<br><223> Trastuzamab light constant (kappa) |
| 18 | <223> Synthetic Construct |
| 19 | <223> Synthetic Construct |
| 20 | <223> Synthetic Construct |
| 21 | <223> Synthetic Construct |
| 22 | <223> Peptide mimotope of HER2 epitope |
| 23 | <223> trastuzumab immunoglobulin H435A mutant |
| 24 | <223> immunoglobulin fragment with I253A mutant |
| 25 | <223> Trastruzumab heavy chain |

This application contains sequences and a sequence listing, which is hereby incorporated by reference. This file is labeled "14-7028PCT_ST25.txt". U.S. application Ser. No. 15/306,413, filed Oct. 24, 2016, allowed, which is a 371 of PCT/US15/27491, filed Apr. 24, 2015, now expired which claimed the benefit of U.S. Provisional Patent Application No. 61/984,646, filed Apr. 25, 20145, now expired, and all publications, patents, and patent applications cited in this application are hereby incorporated by reference in their entireties as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

The invention claimed is:

1. A composition comprising at least one recombinant adeno-associated virus (rAAV) and at least one pharmaceutically acceptable carrier, preservative, and/or stabilizer, wherein the at least one rAAV comprises a vector genome in an AAV capsid,
wherein the vector genome is a nucleic acid molecule which comprises an AAV 5' ITR, an expression cassette, and an AAV 3' ITR,
wherein said expression cassette comprises:
(i) a coding sequence for an anti-Her2 immunoglobulin heavy chain having an IL-2 leader peptide, a heavy chain variable region having an amino acid sequence of SEQ ID NO: 18 and a heavy chain constant region,
(ii) a linker sequence,
(iii) a coding sequence for an anti-Her2 immunoglobulin light chain having an IL-2 leader peptide, a light chain variable region having an amino acid sequence of SEQ ID NO: 20, and a light chain constant region, and
(iv) regulatory sequences which direct expression of the heavy chain and the light chain, and
wherein following expression in the cell, a anti-Her2 heavy chain and the anti-Her2 light chain form an anti-Her2 antibody in vivo.

2. The composition according to claim 1, wherein the anti-Her2 immunoglobulin antibody is directed to a primary or metastatic CNS cancer.

3. The composition according to claim 2, wherein the anti-Her2 antibody is directed to a metastatic CNS cancer which is a breast cancer CNS metastasis.

4. The composition according to claim 1, wherein the sequences encoding the anti-Her2 immunoglobulin heavy chain comprises a heavy chain variable region comprising nucleotides 1314 to 1673 of SEQ ID NO: 17 which encode the amino acid sequence of SEQ ID NO: 18, and a heavy chain constant region comprising nucleotides 1674 to 2660 of SEQ ID NO: 17 which encode the amino acid sequence of SEQ ID NO: 19.

5. The composition according to claim 1, wherein the sequences encoding the anti-Her2 immunoglobulin light chain comprises a light chain variable region comprising nucleotides 2805 to 3110 of SEQ ID NO: 17 which encode the amino acid sequence of SEQ ID NO: 20, and a light chain constant region comprising nucleotides 3111 to 3452 of SEQ ID NO: 17 which encode the amino acid sequence of SEQ ID NO: 21.

6. The composition according to claim 1, wherein the at least one rAAV has an AAV9, AAV rh10 or AAV hu37 capsid.

7. The composition according to claim 1, wherein the composition comprises an rAAV comprising at least two different antibody expression cassettes.

8. The composition according to claim 1, wherein the composition comprises an rAAV comprising a single antibody expression cassette.

9. A method for retarding the growth of a tumor in the brain, said method comprising administering a composition according to claim 1 to a subject in need thereof.

10. The method according to claim 9, wherein said composition is administered intrathecally.

11. The method according to claim 9, wherein said composition is administered in the absence of chemical or physical disruption of the blood brain barrier.

12. A method for treating metastatic breast cancer in the brain, said method comprising administering a composition according to claim 1 to a subject in need thereof.

13. The method according to claim 12, wherein said composition is administered intrathecally.

14. The method according to claim 12, wherein said composition is administered in the absence of chemical or physical disruption of the blood brain barrier.

15. An anti-neoplastic regimen comprising administering a composition according to claim 1 in combination with a biologic drug, a small molecule, anti-neoplastic agent, radiation, and/or a chemotherapeutic agent.

16. The composition according to claim 1, wherein the linker is a furin-2A self-cleaving peptide linker.

* * * * *

SEQUENCE LISTING

<160> NUMBER OF SEQ ID NOS: 25

<210> SEQ ID NO 1
<211> LENGTH: 2717
<212> TYPE: DNA
<213> ORGANISM: Artificial sequence
<220> FEATURE:
<223> OTHER INFORMATION: engineered anti-HER antibody
<220> FEATURE:
<221> NAME/KEY: misc
<222> LOCATION: (1)..(60)
<223> OTHER INFORMATION: IL2 signal/leader peptide
<220> FEATURE:
<221> NAME/KEY: CDS
<222> LOCATION: (61)..(423)
<223> OTHER INFORMATION: heavy variable
<220> FEATURE:
<221> NAME/KEY: Misc
<222> LOCATION: (439)..(714)
<223> OTHER INFORMATION: CH1
<220> FEATURE:
<221> NAME/KEY: Misc
<222> LOCATION: (715)..(1410)
<223> OTHER INFORMATION: CH1
<220> FEATURE:
<221> NAME/KEY: IRES
<222> LOCATION: (1422)..(2009)
<220> FEATURE:
<221> NAME/KEY: Misc
<222> LOCATION: (2010)..(2069)
<223> OTHER INFORMATION: IL2 signal/leader peptide
<220> FEATURE:
<221> NAME/KEY: Misc
<222> LOCATION: (2070)..(2391)
<223> OTHER INFORMATION: variable light
<220> FEATURE:
<221> NAME/KEY: Misc
<222> LOCATION: (2407)..(2711)
<223> OTHER INFORMATION: light chain constant region

<400> SEQUENCE: 1

```
atgtaccgga tgcagctgct gagctgtatc gccctgtctc tggccctcgt gaccaacagc        60 gaa gtg cag ctg gtg gaa agc ggc gga gga ctg gtg cag cct ggc gga         108
Glu Val Gln Leu Val Glu Ser Gly Gly Gly Leu Val Gln Pro Gly Gly
1               5                   10                  15 tct ctg aga ctg agc tgt gcc gcc agc ggc ttc aac atc aag gac acc         156
Ser Leu Arg Leu Ser Cys Ala Ala Ser Gly Phe Asn Ile Lys Asp Thr
            20                  25                  30 tac atc cac tgg gtg cgc cag gcc cct ggc aag gga ctg gaa tgg gtg         204
Tyr Ile His Trp Val Arg Gln Ala Pro Gly Lys Gly Leu Glu Trp Val
        35                  40                  45 gcc aga atc tac ccc acc aac ggc tac acc aga tac gcc gac agc gtg         252
Ala Arg Ile Tyr Pro Thr Asn Gly Tyr Thr Arg Tyr Ala Asp Ser Val
    50                  55                  60 aag ggc cgg ttc acc atc agc gcc gac acc agc aag aac acc gcc tac         300
Lys Gly Arg Phe Thr Ile Ser Ala Asp Thr Ser Lys Asn Thr Ala Tyr
65                  70                  75                  80 ctg cag atg aac agc ctg cgg gcc gag gac acc gcc gtg tac tac tgt         348
Leu Gln Met Asn Ser Leu Arg Ala Glu Asp Thr Ala Val Tyr Tyr Cys
                85                  90                  95 agt aga tgg gga ggc gac ggc ttc tac gcc atg gac tat tgg ggc cag         396
Ser Arg Trp Gly Gly Asp Gly Phe Tyr Ala Met Asp Tyr Trp Gly Gln
            100                 105                 110 ggc acc ctc gtg aca gtg tct agt gcg tcgaccaagg ggccctcggt              443
Gly Thr Leu Val Thr Val Ser Ser Ala
            115                 120
```

```
cttcccctg gcaccctcct ccaagagcac ctctgggggc acagcggccc tgggctgcct      503
ggtcaaggac tacttccccg aaccggtgac ggtgtcgtgg aactcaggcg ccctgaccag      563
cggcgtgcac accttcccgg ctgtcctaca gtcctcagga ctctactccc tcagcagcgt      623
ggtgaccgtg ccctccagca gcttgggcac ccagacctac atctgcaacg tgaatcacaa      683
gcccagcaac accaaggtgg acaagaaagt tgagcccaaa tcttgtgaca aaactcacac      743
atgcccaccg tgcccagcac ctgaactcct ggggggaccg tcagtcttcc tcttcccccc      803
aaaacccaag gacaccctca tgatctcccg gacccctgag gtcacatgcg tggtggtgga      863
cgtgagccac gaagaccctg aggtcaagtt caactggtac gtggacggcg tggaggtgca      923
taatgccaag acaaagccgc gggaggagca gtacaacagc acgtaccgtg tggtcagcgt      983
cctcaccgtc ctgcaccagg actggctgaa tggcaaggag tacaagtgca aggtctccaa     1043
caaagccctc ccagccccca tcgagaaaac catctccaaa gccaaagggc agccccgaga     1103
accacaggtg tacaccctgc ccccatcccg ggatgagctg accaagaacc aggtcagcct     1163
gacctgcctg gtcaaaggct tctatcccag cgacatcgcc gtggagtggg agagcaatgg     1223
gcagccggag aacaactaca agaccacgcc tcccgtgctg gactccgacg gctccttctt     1283
cctctacagc aagctcaccg tggacaagag caggtggcag caggggaacg tcttctcatg     1343
ctccgtgatg catgaggctc tgcacaacca ctacacgcag aagagcctct ccctgtctcc     1403
cggcaagtga taaggccggc ccctctccct cccccccccc taacgttact ggccgaagcc     1463
gcttggaata aggccggtgt gcgtttgtct atatgttatt ttccaccata ttgccgtctt     1523
ttggcaatgt gagggcccgg aaacctggcc ctgtcttctt gacgagcatt cctaggggtc     1583
tttcccctct cgccaaagga atgcaaggtc tgttgaatgt cgtgaaggaa gcagttcctc     1643
tggaagcttc ttgaagacaa acaacgtctg tagcgaccct ttgcaggcag cggaaccccc     1703
cacctggcga caggtgcctc tgcggccaaa agccacgtgt ataagataca cctgcaaagg     1763
cggcacaacc ccagtgccac gttgtgagtt ggatagttgt ggaaagagtc aaatggctct     1823
cctcaagcgt attcaacaag gggctgaagg atgcccagaa ggtaccccat tgtatgggat     1883
ctgatctggg gcctcggtac acatgcttta catgtgttta gtcgaggtta aaaaaacgtc     1943 taggccccc gaaccacggg gacgtggttt tcctttgaaa aacacgatga taatatggcc     2003
acaaccatgt accgcatgca actcctgtct tgcattgcac taagtcttgc acttgtcaca     2063
aacagtgata tccagatgac ccagagcccc agcagcctgt ctgccagcgt gggcgacaga     2123
gtgaccatca cctgtagagc cagccaggac gtgaacaccg ccgtggcctg gtatcagcag     2183
aagcctggca aggcccccaa gctgctgatc tacagcgcca gcttcctgta cagcggcgtg     2243
cccagcagat tcagcggcag cagatccggc accgacttca ccctgaccat cagctccctg     2303
cagcccgagg acttcgccac ctactactgc cagcagcact acaccacccc cccacattt      2363 ggccagggca ccaaggtgga aatcaagcgt acggtggctg caccatctgt cttcatcttc     2423
ccgccatctg atgagcagtt gaaatctgga actgcctctg ttgtgtgcct gctgaataac     2483
ttctacccca gagaagccaa agtgcagtgg aaggtggaca acgccctgca gagcggaaac     2543
agccaggaaa gcgtgacaga gcaggattcc aaggattcca catacagcct gagcagcaca     2603
ctgacactgt ccaaggccga ctacgagaag cacaaggtgt acgcctgcga agtgacacac     2663
cagggactgt cctcccctgt gacaaagagc ttcaacagag gagaatgctg ataa           2717
```

-continued

```
<210> SEQ ID NO 2
<211> LENGTH: 121
<212> TYPE: PRT
<213> ORGANISM: Artificial sequence
<220> FEATURE:
<223> OTHER INFORMATION: Synthetic Construct

<400> SEQUENCE: 2
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala
        115                 120

```
<210> SEQ ID NO 3
<211> LENGTH: 470
<212> TYPE: PRT
<213> ORGANISM: Artificial sequence
<220> FEATURE:
<223> OTHER INFORMATION: engineered anti-HER heavy chain
<220> FEATURE:
<221> NAME/KEY: MISC_FEATURE
<222> LOCATION: (1)..(20)
<223> OTHER INFORMATION: heavy chain signal peptide
<220> FEATURE:
<221> NAME/KEY: MISC_FEATURE
<222> LOCATION: (21)..(140)
<223> OTHER INFORMATION: heavy chain variable region
<220> FEATURE:
<221> NAME/KEY: MISC_FEATURE
<222> LOCATION: (141)..(259)
<223> OTHER INFORMATION: heavy chain constant region 1
<220> FEATURE:
<221> NAME/KEY: MISC_FEATURE
<222> LOCATION: (260)..(470)
<223> OTHER INFORMATION: heavy chain FC

<400> SEQUENCE: 3
```

Met Tyr Arg Met Gln Leu Leu Ser Cys Ile Ala Leu Ser Leu Ala Leu
1               5                   10                  15

Val Thr Asn Ser Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

```
Val Tyr Tyr Cys Ser Arg Trp Gly Gly Asp Gly Phe Tyr Ala Met Asp
            115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 4
<211> LENGTH: 214
<212> TYPE: PRT
<213> ORGANISM: Artificial sequence
<220> FEATURE:
<223> OTHER INFORMATION: Engineered anti-Her2 light chain
```

```
<220> FEATURE:
<221> NAME/KEY: MISC_FEATURE
<222> LOCATION: (1)..(20)
<223> OTHER INFORMATION: signal sequence
<220> FEATURE:
<221> NAME/KEY: MISC_FEATURE
<222> LOCATION: (21)..(130)
<223> OTHER INFORMATION: light chain variable region
<220> FEATURE:
<221> NAME/KEY: MISC_FEATURE
<222> LOCATION: (131)..(214)
<223> OTHER INFORMATION: light chain constant region

<400> SEQUENCE: 4
```

| | | | | | | | | | | | | | | | |
|---|---|---|---|---|---|---|---|---|---|---|---|---|---|---|---|
| Met | Tyr | Arg | Met | Gln | Leu | Leu | Ser | Cys | Ile | Ala | Leu | Ser | Leu | Ala | Leu |
| 1 | | | | 5 | | | | | 10 | | | | | 15 | |
| Val | Thr | Asn | Ser | Asp | Ile | Gln | Met | Thr | Gln | Ser | Pro | Ser | Ser | Leu | Ser |
| | | | 20 | | | | | 25 | | | | | 30 | | |
| Ala | Ser | Val | Gly | Asp | Arg | Val | Thr | Ile | Thr | Cys | Arg | Ala | Ser | Gln | Asp |
| | | 35 | | | | | 40 | | | | | 45 | | | |
| Val | Asn | Thr | Ala | Val | Ala | Trp | Tyr | Gln | Gln | Lys | Pro | Gly | Lys | Ala | Pro |
| | 50 | | | | | 55 | | | | | 60 | | | | |
| Lys | Leu | Leu | Ile | Tyr | Ser | Ala | Ser | Phe | Leu | Tyr | Ser | Gly | Val | Pro | Ser |
| 65 | | | | | 70 | | | | | 75 | | | | | 80 |
| Arg | Phe | Ser | Gly | Ser | Arg | Ser | Gly | Thr | Asp | Phe | Thr | Leu | Thr | Ile | Ser |
| | | | | 85 | | | | | 90 | | | | | 95 | |
| Ser | Leu | Gln | Pro | Glu | Asp | Phe | Ala | Thr | Tyr | Tyr | Cys | Gln | Gln | His | Tyr |
| | | | 100 | | | | | 105 | | | | | 110 | | |
| Thr | Thr | Pro | Pro | Thr | Phe | Gly | Gln | Gly | Thr | Lys | Val | Glu | Ile | Lys | Arg |
| | | 115 | | | | | 120 | | | | | 125 | | | |
| Thr | Val | Ala | Ala | Pro | Ser | Val | Phe | Ile | Phe | Pro | Pro | Ser | Asp | Glu | Gln |
| | 130 | | | | | 135 | | | | | 140 | | | | |
| Leu | Lys | Ser | Gly | Thr | Ala | Ser | Val | Val | Cys | Leu | Leu | Asn | Asn | Phe | Tyr |
| 145 | | | | | 150 | | | | | 155 | | | | | 160 |
| Pro | Arg | Glu | Ala | Lys | Val | Gln | Trp | Lys | Val | Asp | Asn | Ala | Leu | Gln | Ser |
| | | | | 165 | | | | | 170 | | | | | 175 | |
| Gly | Asn | Ser | Gln | Glu | Ser | Val | Thr | Glu | Gln | Asp | Ser | Lys | Asp | Ser | Thr |
| | | | 180 | | | | | 185 | | | | | 190 | | |
| Tyr | Ser | Leu | Ser | Ser | Thr | Leu | Thr | Leu | Ser | Lys | Ala | Asp | Tyr | Glu | Lys |
| | | 195 | | | | | 200 | | | | | 205 | | | |
| His | Lys | Val | Tyr | Ala | Cys | | | | | | | | | | |
| | 210 | | | | | | | | | | | | | | |

```
<210> SEQ ID NO 5
<211> LENGTH: 6694
<212> TYPE: DNA
<213> ORGANISM: Artificial sequence
<220> FEATURE:
<223> OTHER INFORMATION: pAAV.CB7.CI.201IA.rBG
<220> FEATURE:
<221> NAME/KEY: polyA_signal
<222> LOCATION: (60)..(186)
<220> FEATURE:
<221> NAME/KEY: misc_feature
<222> LOCATION: (275)..(404)
<223> OTHER INFORMATION: 3' ITR (complement)
<220> FEATURE:
<221> NAME/KEY: rep_origin
<222> LOCATION: (581)..(1036)
<220> FEATURE:
<221> NAME/KEY: misc_feature
<222> LOCATION: (3226)..(3355)
<223> OTHER INFORMATION: 5' ITR
```

```
<220> FEATURE:
<221> NAME/KEY: misc
<222> LOCATION: (3423)..(3804)
<223> OTHER INFORMATION: CMV IE promoter
<220> FEATURE:
<221> NAME/KEY: promoter
<222> LOCATION: (3807)..(4088)
<220> FEATURE:
<221> NAME/KEY: TATA_signal
<222> LOCATION: (4061)..(4064)
<220> FEATURE:
<221> NAME/KEY: Intron
<222> LOCATION: (4183)..(5155)
<220> FEATURE:
<221> NAME/KEY: CDS
<222> LOCATION: (5161)..(6690)
<223> OTHER INFORMATION: 201IA

<400> SEQUENCE: 5
gtacctctag agtcgacccg ggcggcctcg aggacggggt gaactacgcc tgaggatccg      60 atcttttcc ctctgccaaa aattatgggg acatcatgaa gccccttgag catctgactt     120
ctggctaata aggaaatttt attttcattg caatagtgtg ttggaatttt ttgtgtctct     180
cactcggaag caattcgttg atctgaattt cgaccaccca taatacccat taccctggta     240
gataagtagc atggcgggtt aatcattaac tacaaggaac ccctagtgat ggagttggcc     300
actccctctc tgcgcgctcg ctcgctcact gaggccgggc gaccaaaggt cgcccgacgc     360
ccgggctttg cccgggcggc ctcagtgagc gagcgagcgc gcagcttaa ttaacctaat     420 tcactggccg tcgttttaca acgtcgtgac tgggaaaacc ctggcgttac ccaacttaat     480
cgccttgcag cacatccccc tttcgccagc tggcgtaata gcgaagaggc ccgcaccgat     540
cgcccttccc aacagttgcg cagcctgaat ggcgaatggg acgcgccctg tagcggcgca     600
ttaagcgcgg cgggtgtggt ggttacgcgc agcgtgaccg ctacacttgc cagcgcccta     660
gcgcccgctc ctttcgcttt cttcccttcc tttctcgcca cgttcgccgg ctttccccgt     720
caagctctaa atcgggggct ccctttaggg ttccgattta gtgctttacg gcacctcgac     780
cccaaaaaac ttgattaggg tgatggttca cgtagtgggc catcgccctg atagacggtt     840
tttcgccctt tgacgttgga gtccacgttc tttaatagtg gactcttgtt ccaaactgga     900
acaacactca accctatctc ggtctattct tttgatttat aagggatttt gccgatttcg     960
gcctattggt taaaaaatga gctgatttaa caaaaattta acgcgaattt taacaaaata    1020
ttaacgctta caatttaggt ggcactttc ggggaaatgt gcgcggaacc cctatttgtt    1080
tatttttcta aatacattca aatatgtatc cgctcatgag acaataaccc tgataaatgc    1140
ttcaataata ttgaaaaagg aagagtatga gtattcaaca tttccgtgtc gcccttattc    1200 cctttttgc ggcattttgc cttcctgttt ttgctcaccc agaaacgctg gtgaaagtaa    1260
aagatgctga agatcagttg ggtgcacgag tgggttacat cgaactggat ctcaacagcg    1320
gtaagatcct tgagagtttt cgccccgaag aacgttttcc aatgatgagc acttttaaag    1380
ttctgctatg tggcgcggta ttatcccgta ttgacgccgg gcaagagcaa ctcggtcgcc    1440
gcatacacta ttctcagaat gacttggttg agtactcacc agtcacagaa aagcatctta    1500
cggatggcat gacagtaaga gaattatgca gtgctgccat aaccatgagt gataacactg    1560
cggccaactt acttctgaca acgatcggag gaccgaagga gctaaccgct tttttgcaca    1620
acatggggga tcatgtaact cgccttgatc gttgggaacc ggagctgaat gaagccatac    1680
caaacgacga gcgtgacacc acgatgcctg tagcaatggc aacaacgttg cgcaaactat    1740
taactggcga actacttact ctagcttccc ggcaacaatt aatagactgg atggaggcgg    1800
```

-continued

```
ataaagttgc aggaccactt ctgcgctcgg cccttccggc tggctggttt attgctgata      1860
aatctggagc cggtgagcgt gggtctcgcg gtatcattgc agcactgggg ccagatggta      1920
agccctcccg tatcgtagtt atctacacga cggggagtca ggcaactatg gatgaacgaa      1980
atagacagat cgctgagata ggtgcctcac tgattaagca ttggtaactg tcagaccaag      2040
tttactcata tatactttag attgatttaa aacttcattt ttaatttaaa aggatctagg      2100
tgaagatcct ttttgataat ctcatgacca aaatccctta acgtgagttt tcgttccact      2160
gagcgtcaga ccccgtagaa aagatcaaag gatcttcttg agatcctttt tttctgcgcg      2220
taatctgctg cttgcaaaca aaaaaaccac cgctaccagc ggtggtttgt ttgccggatc      2280
aagagctacc aactcttttt ccgaaggtaa ctggcttcag cagagcgcag ataccaaata      2340
ctgttcttct agtgtagccg tagttaggcc accacttcaa gaactctgta gcaccgccta      2400
catacctcgc tctgctaatc ctgttaccag tggctgctgc cagtggcgat aagtcgtgtc      2460
ttaccgggtt ggactcaaga cgatagttac cggataaggc gcagcggtcg ggctgaacgg      2520
ggggttcgtg cacacagccc agcttggagc gaacgaccta caccgaactg agatacctac      2580
agcgtgagct atgagaaagc gccacgcttc ccgaagggag aaaggcggac aggtatccgg      2640
taagcggcag ggtcggaaca ggagagcgca cgagggagct tccaggggga aacgcctggt      2700
atctttatag tcctgtcggg tttcgccacc tctgacttga gcgtcgattt ttgtgatgct      2760
cgtcaggggg gcggagccta tggaaaaacg ccagcaacgc ggccttttta cggttcctgg      2820
ccttttgctg gccttttgct cacatgttct ttcctgcgtt atcccctgat tctgtggata      2880
accgtattac cgcctttgag tgagctgata ccgctcgccg cagccgaacg accgagcgca      2940
gcgagtcagt gagcgaggaa gcggaagagc gcccaatacg caaaccgcct ctccccgcgc      3000
gttggccgat tcattaatgc agctggcacg acaggtttcc cgactggaaa gcgggcagtg      3060
agcgcaacgc aattaatgtg agttagctca ctcattaggc accccaggct ttacacttta      3120
tgcttccggc tcgtatgttg tgtggaattg tgagcggata acaatttcac acaggaaaca      3180
gctatgacca tgattacgcc agatttaatt aaggccttaa ttaggctgcg cgctcgctcg      3240
ctcactgagg ccgcccgggc aaagcccggg cgtcgggcga cctttggtcg cccggcctca      3300
gtgagcgagc gagcgcgcag agagggagtg gccaactcca tcactagggg ttccttgtag      3360
ttaatgatta acccgccatg ctacttatct accagggtaa tggggatcct ctagaactat      3420
agctagtcga cattgattat tgactagtta ttaatagtaa tcaattacgg ggtcattagt      3480
tcatagccca tatatggagt tccgcgttac ataacttacg gtaaatggcc cgcctggctg      3540
accgcccaac gacccccgcc cattgacgtc aataatgacg tatgttccca tagtaacgcc      3600
aatagggact ttccattgac gtcaatgggt ggactattta cggtaaactg cccacttggc      3660
agtacatcaa gtgtatcata tgccaagtac gccccctatt gacgtcaatg acggtaaatg      3720
gcccgcctgg cattatgccc agtacatgac cttatgggac tttcctactt ggcagtacat      3780
ctacgtatta gtcatcgcta ttaccatggt cgaggtgagc cccacgttct gcttcactct      3840
ccccatctcc cccccctccc cacccccaat tttgtattta tttattttt aattattttg      3900 tgcagcgatg ggggcggggg gggggggggg gcgcgcgcca ggcggggcgg ggcggggcga      3960 ggggcgggc ggggcgaggc ggagaggtgc ggcggcagcc aatcagagcg gcgcgctccg      4020
aaagtttcct tttatggcga ggcggcggcg gcggcggccc tataaaaagc gaagcgcgcg      4080
gcgggcgggg agtcgctgcg acgctgcctt cgccccgtgc cccgctccgc cgccgcctcg      4140
cgccgcccgc cccggctctg actgaccgcg ttactcccac aggtgagcgg gcgggacggc      4200
```

```
                                        -continued
ccttctcctc cgggctgtaa ttagcgcttg gtttaatgac ggcttgtttc ttttctgtgg      4260
ctgcgtgaaa gccttgaggg gctccgggag ggcccttttgt gcgggggggag cggctcgggg    4320 ggtgcgtgcg tgtgtgtgtg cgtggggagc gccgcgtgcg gctccgcgct gcccggcggc     4380
tgtgagcgct gcgggcgcgg cgcggggctt tgtgcgctcc gcagtgtgcg cgaggggagc     4440
gcggccgggg gcggtgcccc gcggtgcggg gggggctgcg aggggaacaa aggctgcgtg     4500
cggggtgtgt gcgtgggggg gtgagcaggg ggtgtgggcg cgtcggtcgg gctgcaaccc    4560
cccctgcacc ccctccccg agttgctgag cacggcccgg cttcgggtgc ggggctccgt    4620
acggggcgtg gcgcggggct cgccgtgccg ggcggggggt ggcggcaggt gggggtgccg    4680
ggcggggcgg ggccgcctcg ggccggggag ggctcggggg aggggcgcgg cggccccgg     4740 agcgccggcg gctgtcgagg gcgggcgagc cgcagccatt gccttttatg gtaatcgtgc     4800
gagagggcgc agggacttcc tttgtcccaa atctgtgcgg agccgaaatc tgggaggcgc     4860
cgccgcaccc cctctagcgg gcgcggggcg aagcggtgcg gcgccggcag gaaggaaatg    4920
ggcggggagg gccttcgtgc gtcgccgcgc cgccgtcccc ttctccctct ccagcctcgg    4980
ggctgtccgc gggggacgg ctgccttcgg ggggacggg gcagggcggg gttcggcttc       5040
tggcgtgtga ccggcggctc tagagcctct gctaaccatg ttcatgcctt cttctttttc    5100
ctacagctcc tgggcaacgt gctggttatt gtgctgtctc atcattttgg caaagaattc    5160 atg gag ttc ggg ctg agc tgg gtc ttt ctg gtg gcc ctg ctg aag gga      5208
Met Glu Phe Gly Leu Ser Trp Val Phe Leu Val Ala Leu Leu Lys Gly
1               5                   10                  15 gtc cag tgc gag gtg cag ctg ctg gaa tcc gga cct ggc ctg gtg aaa      5256
Val Gln Cys Glu Val Gln Leu Leu Glu Ser Gly Pro Gly Leu Val Lys
            20                  25                  30 cca tct gag aca ctg agt ctg act tgt gct gtc tcc ggc ctg tct atc      5304
Pro Ser Glu Thr Leu Ser Leu Thr Cys Ala Val Ser Gly Leu Ser Ile
        35                  40                  45 agc tcc gat ttc tcc tgg gca tgg att agg cag acc ccc ggc aag gcc      5352
Ser Ser Asp Phe Ser Trp Ala Trp Ile Arg Gln Thr Pro Gly Lys Ala
    50                  55                  60 ctg gaa tat gtg ggg tac atc cgc ggg aac acc gga gat aca tac tat      5400
Leu Glu Tyr Val Gly Tyr Ile Arg Gly Asn Thr Gly Asp Thr Tyr Tyr
65                  70                  75                  80 aat cct agt ctg aag tca agg ctg act atc tca aag gac acc agc aaa      5448
Asn Pro Ser Leu Lys Ser Arg Leu Thr Ile Ser Lys Asp Thr Ser Lys
                85                  90                  95 aac caa atc tac ctg aat ctg tct agt gtc acc gct ggc gat gcc gcc      5496
Asn Gln Ile Tyr Leu Asn Leu Ser Ser Val Thr Ala Gly Asp Ala Ala
            100                 105                 110 gtg tac tat tgc gca agg gac cgg gtg tgc gac gat gac tac gga tac      5544
Val Tyr Tyr Cys Ala Arg Asp Arg Val Cys Asp Asp Asp Tyr Gly Tyr
        115                 120                 125 tat tac acc gag gtg tgc ttc ggc ctg gat tct tgg ggg cag gga atc      5592
Tyr Tyr Thr Glu Val Cys Phe Gly Leu Asp Ser Trp Gly Gln Gly Ile
    130                 135                 140 gtg gtc aca gtg tca agc ggc gga gga ggc agc gga gga gga ggg tcc      5640
Val Val Thr Val Ser Ser Gly Gly Gly Gly Ser Gly Gly Gly Gly Ser
145                 150                 155                 160 gga ggc ggg gga tct gca gaa ctg gtc atg aca cag tcc cca ctg agc      5688
Gly Gly Gly Gly Ser Ala Glu Leu Val Met Thr Gln Ser Pro Leu Ser
                165                 170                 175 ctg tcc gtc gct cca gga cag act gca tct att agt tgt cga tcc tct      5736
Leu Ser Val Ala Pro Gly Gln Thr Ala Ser Ile Ser Cys Arg Ser Ser
            180                 185                 190
```

| | | |
|---|---|---|
| cag tcc ctg gac tat gct aac ggc aat acc tac ctg tct tgg ttt cac<br>Gln Ser Leu Asp Tyr Ala Asn Gly Asn Thr Tyr Leu Ser Trp Phe His<br>    195                      200                    205 | | 5784 |
| cag cga cca gga cag cca cct cgg aga ctg atc tat cag att tcc aac<br>Gln Arg Pro Gly Gln Pro Pro Arg Arg Leu Ile Tyr Gln Ile Ser Asn<br>   210                      215                    220 | | 5832 |
| aga gat tct gga gtg ccc gac agg ttc tca ggc agc gga gca gga act<br>Arg Asp Ser Gly Val Pro Asp Arg Phe Ser Gly Ser Gly Ala Gly Thr<br>225                      230                    235                    240 | | 5880 |
| gag ttt acc ctg cga atc agt cgg atg gaa tca gat gac gtg ggg atc<br>Glu Phe Thr Leu Arg Ile Ser Arg Met Glu Ser Asp Asp Val Gly Ile<br>                    245                    250                    255 | | 5928 |
| tac tac tgc gga cag ggg acc aca ttc cca cgg aca ttt gga cag ggc<br>Tyr Tyr Cys Gly Gln Gly Thr Thr Phe Pro Arg Thr Phe Gly Gln Gly<br>          260                      265                    270 | | 5976 |
| act aag gtg gag atc aaa acc tgt gga gga gga agc aag cca cca acc<br>Thr Lys Val Glu Ile Lys Thr Cys Gly Gly Gly Ser Lys Pro Pro Thr<br> 275                      280                    285 | | 6024 |
| tgc cct cca tgt aca tct ccc gaa ctg ctg ggc ggg cct agc gtg ttc<br>Cys Pro Pro Cys Thr Ser Pro Glu Leu Leu Gly Gly Pro Ser Val Phe<br>   290                      295                    300 | | 6072 |
| ctg ttt ccc cct aag cct aaa gat aca ctg atg att agt aga acc cca<br>Leu Phe Pro Pro Lys Pro Lys Asp Thr Leu Met Ile Ser Arg Thr Pro<br>305                      310                    315                    320 | | 6120 |
| gag gtc aca tgc gtg gtc gtg gac gtg tcc cag gaa gat cct gac gtg<br>Glu Val Thr Cys Val Val Val Asp Val Ser Gln Glu Asp Pro Asp Val<br>                    325                    330                    335 | | 6168 |
| aag ttc aac tgg tac gtg aat ggc gcc gag gtg cac cat gct cag act<br>Lys Phe Asn Trp Tyr Val Asn Gly Ala Glu Val His His Ala Gln Thr<br>          340                      345                    350 | | 6216 |
| aaa cca cgc gaa acc cag tat aat agt aca tac cga gtc gtg tca gtc<br>Lys Pro Arg Glu Thr Gln Tyr Asn Ser Thr Tyr Arg Val Val Ser Val<br> 355                      360                    365 | | 6264 |
| ctg aca gtg act cac cag gat tgg ctg aac ggc aag gag tat acc tgc<br>Leu Thr Val Thr His Gln Asp Trp Leu Asn Gly Lys Glu Tyr Thr Cys<br>   370                      375                    380 | | 6312 |
| aag gtg tct aac aag gcc ctg ccc gcc cct atc cag aaa aca att agc<br>Lys Val Ser Asn Lys Ala Leu Pro Ala Pro Ile Gln Lys Thr Ile Ser<br>385                      390                    395                    400 | | 6360 |
| aag gac aaa ggg cag cca cgg gaa ccc cag gtg tac act ctg cca ccc<br>Lys Asp Lys Gly Gln Pro Arg Glu Pro Gln Val Tyr Thr Leu Pro Pro<br>                    405                    410                    415 | | 6408 |
| tca aga gag gaa ctg act aag aac cag gtc agc ctg acc tgt ctg gtg<br>Ser Arg Glu Glu Leu Thr Lys Asn Gln Val Ser Leu Thr Cys Leu Val<br>          420                      425                    430 | | 6456 |
| aaa ggc ttc tac ccc agc gat atc gtc gtg gag tgg gaa agt tca ggc<br>Lys Gly Phe Tyr Pro Ser Asp Ile Val Val Glu Trp Glu Ser Ser Gly<br> 435                      440                    445 | | 6504 |
| cag cct gag aat act tac aag act acc cct cca gtg ctg gat agc gac<br>Gln Pro Glu Asn Thr Tyr Lys Thr Thr Pro Pro Val Leu Asp Ser Asp<br>   450                      455                    460 | | 6552 |
| ggg tcc tat ttc ctg tac agc aag ctg aca gtg gac aaa tcc cgc tgg<br>Gly Ser Tyr Phe Leu Tyr Ser Lys Leu Thr Val Asp Lys Ser Arg Trp<br>465                      470                    475                    480 | | 6600 |
| cag cag gga aac gtc ttt tcc tgt tct gtg atg cat gag gcc ctg cac<br>Gln Gln Gly Asn Val Phe Ser Cys Ser Val Met His Glu Ala Leu His<br>                    485                    490                    495 | | 6648 |
| aat cat tac acc cag aag agt ctg tca ctg agc ccc ggc aaa tgag<br>Asn His Tyr Thr Gln Lys Ser Leu Ser Leu Ser Pro Gly Lys<br>          500                      505                    510 | | 6694 |

<210> SEQ ID NO 6
<211> LENGTH: 510
<212> TYPE: PRT
<213> ORGANISM: Artificial sequence
<220> FEATURE:
<223> OTHER INFORMATION: Synthetic Construct

<400> SEQUENCE: 6

```
Met Glu Phe Gly Leu Ser Trp Val Phe Leu Val Ala Leu Leu Lys Gly
1               5                   10                  15

Val Gln Cys Glu Val Gln Leu Leu Glu Ser Gly Pro Gly Leu Val Lys
            20                  25                  30

Pro Ser Glu Thr Leu Ser Leu Thr Cys Ala Val Ser Gly Leu Ser Ile
        35                  40                  45

Ser Ser Asp Phe Ser Trp Ala Trp Ile Arg Gln Thr Pro Gly Lys Ala
    50                  55                  60

Leu Glu Tyr Val Gly Tyr Ile Arg Gly Asn Thr Gly Asp Thr Tyr Tyr
65                  70                  75                  80

Asn Pro Ser Leu Lys Ser Arg Leu Thr Ile Ser Lys Asp Thr Ser Lys
                85                  90                  95

Asn Gln Ile Tyr Leu Asn Leu Ser Ser Val Thr Ala Gly Asp Ala Ala
            100                 105                 110

Val Tyr Tyr Cys Ala Arg Asp Arg Val Cys Asp Asp Tyr Gly Tyr
        115                 120                 125

Tyr Tyr Thr Glu Val Cys Phe Gly Leu Asp Ser Trp Gly Gln Gly Ile
    130                 135                 140

Val Val Thr Val Ser Ser Gly Gly Gly Ser Gly Gly Gly Ser
145                 150                 155                 160

Gly Gly Gly Gly Ser Ala Glu Leu Val Met Thr Gln Ser Pro Leu Ser
                165                 170                 175

Leu Ser Val Ala Pro Gly Gln Thr Ala Ser Ile Ser Cys Arg Ser Ser
            180                 185                 190

Gln Ser Leu Asp Tyr Ala Asn Gly Asn Thr Tyr Leu Ser Trp Phe His
        195                 200                 205

Gln Arg Pro Gly Gln Pro Pro Arg Arg Leu Ile Tyr Gln Ile Ser Asn
    210                 215                 220

Arg Asp Ser Gly Val Pro Asp Arg Phe Ser Gly Ser Gly Ala Gly Thr
225                 230                 235                 240

Glu Phe Thr Leu Arg Ile Ser Arg Met Glu Ser Asp Asp Val Gly Ile
                245                 250                 255

Tyr Tyr Cys Gly Gln Gly Thr Thr Phe Pro Arg Thr Phe Gly Gln Gly
            260                 265                 270

Thr Lys Val Glu Ile Lys Thr Cys Gly Gly Gly Ser Lys Pro Pro Thr
        275                 280                 285

Cys Pro Pro Cys Thr Ser Pro Glu Leu Leu Gly Gly Pro Ser Val Phe
    290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser Gln Glu Asp Pro Asp Val
                325                 330                 335

Lys Phe Asn Trp Tyr Val Asn Gly Ala Glu Val His His Ala Gln Thr
            340                 345                 350

Lys Pro Arg Glu Thr Gln Tyr Asn Ser Thr Tyr Arg Val Val Ser Val
        355                 360                 365
```

```
Leu Thr Val Thr His Gln Asp Trp Leu Asn Gly Lys Glu Tyr Thr Cys
        370                 375                 380

Lys Val Ser Asn Lys Ala Leu Pro Ala Pro Ile Gln Lys Thr Ile Ser
385                 390                 395                 400

Lys Asp Lys Gly Gln Pro Arg Glu Pro Gln Val Tyr Thr Leu Pro Pro
            405                 410                 415

Ser Arg Glu Glu Leu Thr Lys Asn Gln Val Ser Leu Thr Cys Leu Val
            420                 425                 430

Lys Gly Phe Tyr Pro Ser Asp Ile Val Val Glu Trp Glu Ser Ser Gly
        435                 440                 445

Gln Pro Glu Asn Thr Tyr Lys Thr Thr Pro Pro Val Leu Asp Ser Asp
    450                 455                 460

Gly Ser Tyr Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
            485                 490                 495

Asn His Tyr Thr Gln Lys Ser Leu Ser Leu Ser Pro Gly Lys
            500                 505                 510

<210> SEQ ID NO 7
<211> LENGTH: 6694
<212> TYPE: DNA
<213> ORGANISM: Artificial sequence
<220> FEATURE:
<223> OTHER INFORMATION: Plasmid encoding 2011A(I253A)mutant
<220> FEATURE:
<221> NAME/KEY: misc
<222> LOCATION: (1)..(130)
<223> OTHER INFORMATION: 5' ITR
<220> FEATURE:
<221> NAME/KEY: misc_feature
<222> LOCATION: (198)..(579)
<223> OTHER INFORMATION: CMV IE promoter
<220> FEATURE:
<221> NAME/KEY: promoter
<222> LOCATION: (582)..(863)
<223> OTHER INFORMATION: CB promoter
<220> FEATURE:
<221> NAME/KEY: TATA_signal
<222> LOCATION: (836)..(839)
<220> FEATURE:
<221> NAME/KEY: Intron
<222> LOCATION: (958)..(1930)
<223> OTHER INFORMATION: chicken beta-actin intron
<220> FEATURE:
<221> NAME/KEY: CDS
<222> LOCATION: (1936)..(3465)
<223> OTHER INFORMATION: CMV IE promoter
<220> FEATURE:
<221> NAME/KEY: polyA_signal
<222> LOCATION: (3529)..(3655)
<223> OTHER INFORMATION: rabbit globin polyA
<220> FEATURE:
<221> NAME/KEY: misc_feature
<222> LOCATION: (3744)..(3873)
<223> OTHER INFORMATION: 3' ITR (complement)
<220> FEATURE:
<221> NAME/KEY: rep_origin
<222> LOCATION: (4050)..(4505)
<220> FEATURE:
<221> NAME/KEY: misc_feature
<222> LOCATION: (4636)..(5493)
<223> OTHER INFORMATION: AP(R) marker
<220> FEATURE:
<221> NAME/KEY: rep_origin
<222> LOCATION: (5667)..(6255)
```

<400> SEQUENCE: 7

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctaccag ggtaatgggg     180
atcctctaga actatagcta gtcgacattg attattgact agttattaat agtaatcaat     240
tacgggtca ttagttcata gcccatatat ggagttccgc gttacataac ttacggtaaa      300
tggcccgcct ggctgaccgc ccaacgaccc ccgcccattg acgtcaataa tgacgtatgt     360
tcccatagta acgccaatag ggactttcca ttgacgtcaa tgggtggact atttacggta     420
aactgcccac ttggcagtac atcaagtgta tcatatgcca agtacgcccc ctattgacgt     480
caatgacggt aaatggcccg cctggcatta tgcccagtac atgaccttat gggactttcc     540
tacttggcag tacatctacg tattagtcat cgctattacc atggtcgagg tgagccccac     600
gttctgcttc actctcccca tctcccccc ctccccaccc ccaatttgt atttattat        660
tttttaatta ttttgtgcag cgatggggg gggggggggg gggggcgcg cgccaggcgg      720
ggcggggcgg ggcgaggggc gggcggggc gaggcggaga ggtgcggcgg cagccaatca     780
gagcggcgcg ctccgaaagt ttcctttat ggcgaggcgg cggcggcggc ggccctataa     840
aaagcgaagc gcgcggcggg cggggagtcg ctgcgacgct gccttcgccc cgtgccccgc    900
tccgccgccg cctcgcgccg cccgcccgg ctctgactga ccgcgttact cccacaggtg     960
agcgggcggg acggcccttc tcctccgggc tgtaattagc gcttggttta atgacggctt   1020
gtttcttttc tgtggctgcg tgaaagcctt gaggggctcc gggagggccc tttgtgcggg   1080
gggagcggct cggggggtgc gtgcgtgtgt gtgtgcgtgg ggagcgccgc gtgcggctcc   1140
gcgctgcccg gcggctgtga gcgctgcggg cgcggcgcgg ggctttgtgc gctccgcagt   1200
gtgcgcgagg ggagcgcggc cggggcggt gcccgcgct gcggggggg ctgcgagggg      1260
aacaaaggct gcgtgcgggg tgtgtgcgtg ggggggtgag caggggtgt gggcgcgtcg    1320
gtcgggctgc aacccccct gcaccccct ccccgagttg ctgagcacgg cccggcttcg     1380
ggtgcggggc tccgtacggg gcgtggcgcg gggctcgccg tgccgggcgg ggggtggcgg    1440
caggtggggg tgccgggcgg ggcggggccg cctcgggccg gggagggctc ggggaggggg   1500
cgcggcggcc cccggagcgc cggcggctgt cgaggcgcgg cgagccgcag ccattgcctt   1560
ttatggtaat cgtgcgagag ggcgcaggga cttcctttgt cccaaatctg tgcggagccg   1620
aaatctggga ggcgccgccg caccccctct agcgggcgcg gggcgaagcg gtgcggcgcc   1680
ggcaggaagg aaatgggcgg ggagggcctt cgtgcgtcgc cgcgccgccg tccccttctc   1740
cctctccagc ctcggggctg tccgcggggg gacggctgcc ttcgggggg acgggcagg     1800
gcggggttcg gcttctggcg tgtgaccggc ggctctagag cctctgctaa ccatgttcat   1860
gccttcttct ttttcctaca gctcctgggc aacgtgctgg ttattgtgct gtctcatcat   1920
```

| | | | | |
|---|---|---|---|---|
|tttggcaaag aattc atg gag ttc ggg ctg agc tgg gtc ttt ctg gtg gcc | | | | |1971|
| | Met Glu Phe Gly Leu Ser Trp Val Phe Leu Val Ala | | | | |
| | 1 | 5 | | 10 | |

```
ctg ctg aag gga gtc cag tgc gag gtg cag ctg ctg gaa tcc gga cct    2019
Leu Leu Lys Gly Val Gln Cys Glu Val Gln Leu Leu Glu Ser Gly Pro
             15                  20                  25 ggc ctg gtg aaa cca tct gag aca ctg agt ctg act tgt gct gtc tcc    2067
Gly Leu Val Lys Pro Ser Glu Thr Leu Ser Leu Thr Cys Ala Val Ser
     30                  35                  40
```

-continued

| | | | | | | | | | | | | | | | | |
|---|---|---|---|---|---|---|---|---|---|---|---|---|---|---|---|---|
| ggc | ctg | tct | atc | agc | tcc | gat | ttc | tcc | tgg | gca | tgg | att | agg | cag | acc | 2115 |
| Gly | Leu | Ser | Ile | Ser | Ser | Asp | Phe | Ser | Trp | Ala | Trp | Ile | Arg | Gln | Thr | |
| 45 | | | | 50 | | | | | 55 | | | | | 60 | | |

| | | | | | | | | | | | | | | | | |
|---|---|---|---|---|---|---|---|---|---|---|---|---|---|---|---|---|
| ccc | ggc | aag | gcc | ctg | gaa | tat | gtg | ggg | tac | atc | cgc | ggg | aac | acc | gga | 2163 |
| Pro | Gly | Lys | Ala | Leu | Glu | Tyr | Val | Gly | Tyr | Ile | Arg | Gly | Asn | Thr | Gly | |
| | | | | 65 | | | | | 70 | | | | | 75 | | |

| | | | | | | | | | | | | | | | | |
|---|---|---|---|---|---|---|---|---|---|---|---|---|---|---|---|---|
| gat | aca | tac | tat | aat | cct | agt | ctg | aag | tca | agg | ctg | act | atc | tca | aag | 2211 |
| Asp | Thr | Tyr | Tyr | Asn | Pro | Ser | Leu | Lys | Ser | Arg | Leu | Thr | Ile | Ser | Lys | |
| | | | 80 | | | | | 85 | | | | | 90 | | | |

| | | | | | | | | | | | | | | | | |
|---|---|---|---|---|---|---|---|---|---|---|---|---|---|---|---|---|
| gac | acc | agc | aaa | aac | caa | atc | tac | ctg | aat | ctg | tct | agt | gtc | acc | gct | 2259 |
| Asp | Thr | Ser | Lys | Asn | Gln | Ile | Tyr | Leu | Asn | Leu | Ser | Ser | Val | Thr | Ala | |
| | | 95 | | | | | 100 | | | | | 105 | | | | |

| | | | | | | | | | | | | | | | | |
|---|---|---|---|---|---|---|---|---|---|---|---|---|---|---|---|---|
| ggc | gat | gcc | gcc | gtg | tac | tat | tgc | gca | agg | gac | cgg | gtg | tgc | gac | gat | 2307 |
| Gly | Asp | Ala | Ala | Val | Tyr | Tyr | Cys | Ala | Arg | Asp | Arg | Val | Cys | Asp | Asp | |
| | 110 | | | | | 115 | | | | | 120 | | | | | |

| | | | | | | | | | | | | | | | | |
|---|---|---|---|---|---|---|---|---|---|---|---|---|---|---|---|---|
| gac | tac | gga | tac | tat | tac | acc | gag | gtg | tgc | ttc | ggc | ctg | gat | tct | tgg | 2355 |
| Asp | Tyr | Gly | Tyr | Tyr | Tyr | Thr | Glu | Val | Cys | Phe | Gly | Leu | Asp | Ser | Trp | |
| 125 | | | | | 130 | | | | | 135 | | | | | 140 | |

| | | | | | | | | | | | | | | | | |
|---|---|---|---|---|---|---|---|---|---|---|---|---|---|---|---|---|
| ggg | cag | gga | atc | gtg | gtc | aca | gtg | tca | agc | ggc | gga | gga | ggc | agc | gga | 2403 |
| Gly | Gln | Gly | Ile | Val | Val | Thr | Val | Ser | Ser | Gly | Gly | Gly | Gly | Ser | Gly | |
| | | | | 145 | | | | | 150 | | | | | 155 | | |

| | | | | | | | | | | | | | | | | |
|---|---|---|---|---|---|---|---|---|---|---|---|---|---|---|---|---|
| gga | gga | ggg | tcc | gga | ggc | ggg | gga | tct | gca | gaa | ctg | gtc | atg | aca | cag | 2451 |
| Gly | Gly | Gly | Ser | Gly | Gly | Gly | Gly | Ser | Ala | Glu | Leu | Val | Met | Thr | Gln | |
| | | 160 | | | | | 165 | | | | | 170 | | | | |

| | | | | | | | | | | | | | | | | |
|---|---|---|---|---|---|---|---|---|---|---|---|---|---|---|---|---|
| tcc | cca | ctg | agc | ctg | tcc | gtc | gct | cca | gga | cag | act | gca | tct | att | agt | 2499 |
| Ser | Pro | Leu | Ser | Leu | Ser | Val | Ala | Pro | Gly | Gln | Thr | Ala | Ser | Ile | Ser | |
| | | 175 | | | | | 180 | | | | | 185 | | | | |

| | | | | | | | | | | | | | | | | |
|---|---|---|---|---|---|---|---|---|---|---|---|---|---|---|---|---|
| tgt | cga | tcc | tct | cag | tcc | ctg | gac | tat | gct | aac | ggc | aat | acc | tac | ctg | 2547 |
| Cys | Arg | Ser | Ser | Gln | Ser | Leu | Asp | Tyr | Ala | Asn | Gly | Asn | Thr | Tyr | Leu | |
| | 190 | | | | | 195 | | | | | 200 | | | | | |

| | | | | | | | | | | | | | | | | |
|---|---|---|---|---|---|---|---|---|---|---|---|---|---|---|---|---|
| tct | tgg | ttt | cac | cag | cga | cca | gga | cag | cca | cct | cgg | aga | ctg | atc | tat | 2595 |
| Ser | Trp | Phe | His | Gln | Arg | Pro | Gly | Gln | Pro | Pro | Arg | Arg | Leu | Ile | Tyr | |
| 205 | | | | | 210 | | | | | 215 | | | | | 220 | |

| | | | | | | | | | | | | | | | | |
|---|---|---|---|---|---|---|---|---|---|---|---|---|---|---|---|---|
| cag | att | tcc | aac | aga | gat | tct | gga | gtg | ccc | gac | agg | ttc | tca | ggc | agc | 2643 |
| Gln | Ile | Ser | Asn | Arg | Asp | Ser | Gly | Val | Pro | Asp | Arg | Phe | Ser | Gly | Ser | |
| | | | | 225 | | | | | 230 | | | | | 235 | | |

| | | | | | | | | | | | | | | | | |
|---|---|---|---|---|---|---|---|---|---|---|---|---|---|---|---|---|
| gga | gca | gga | act | gag | ttt | acc | ctg | cga | atc | agt | cgg | atg | gaa | tca | gat | 2691 |
| Gly | Ala | Gly | Thr | Glu | Phe | Thr | Leu | Arg | Ile | Ser | Arg | Met | Glu | Ser | Asp | |
| | | | 240 | | | | | 245 | | | | | 250 | | | |

| | | | | | | | | | | | | | | | | |
|---|---|---|---|---|---|---|---|---|---|---|---|---|---|---|---|---|
| gac | gtg | ggg | atc | tac | tac | tgc | gga | cag | ggg | acc | aca | ttc | cca | cgg | aca | 2739 |
| Asp | Val | Gly | Ile | Tyr | Tyr | Cys | Gly | Gln | Gly | Thr | Thr | Phe | Pro | Arg | Thr | |
| | | 255 | | | | | 260 | | | | | 265 | | | | |

| | | | | | | | | | | | | | | | | |
|---|---|---|---|---|---|---|---|---|---|---|---|---|---|---|---|---|
| ttt | gga | cag | ggc | act | aag | gtg | gag | atc | aaa | acc | tgt | gga | gga | gga | agc | 2787 |
| Phe | Gly | Gln | Gly | Thr | Lys | Val | Glu | Ile | Lys | Thr | Cys | Gly | Gly | Gly | Ser | |
| | 270 | | | | | 275 | | | | | 280 | | | | | |

| | | | | | | | | | | | | | | | | |
|---|---|---|---|---|---|---|---|---|---|---|---|---|---|---|---|---|
| aag | cca | cca | acc | tgc | cct | cca | tgt | aca | tct | ccc | gaa | ctg | ctg | ggc | ggg | 2835 |
| Lys | Pro | Pro | Thr | Cys | Pro | Pro | Cys | Thr | Ser | Pro | Glu | Leu | Leu | Gly | Gly | |
| 285 | | | | 290 | | | | | 295 | | | | | 300 | | |

| | | | | | | | | | | | | | | | | |
|---|---|---|---|---|---|---|---|---|---|---|---|---|---|---|---|---|
| cct | agc | gtg | ttc | ctg | ttt | ccc | cct | aag | cct | aaa | gat | aca | ctg | atg | gcc | 2883 |
| Pro | Ser | Val | Phe | Leu | Phe | Pro | Pro | Lys | Pro | Lys | Asp | Thr | Leu | Met | Ala | |
| | | | | 305 | | | | | 310 | | | | | 315 | | |

| | | | | | | | | | | | | | | | | |
|---|---|---|---|---|---|---|---|---|---|---|---|---|---|---|---|---|
| agt | aga | acc | cca | gag | gtc | aca | tgc | gtg | gtc | gtg | gac | gtg | tcc | cag | gaa | 2931 |
| Ser | Arg | Thr | Pro | Glu | Val | Thr | Cys | Val | Val | Val | Asp | Val | Ser | Gln | Glu | |
| | | | 320 | | | | | 325 | | | | | 330 | | | |

| | | | | | | | | | | | | | | | | |
|---|---|---|---|---|---|---|---|---|---|---|---|---|---|---|---|---|
| gat | cct | gac | gtg | aag | ttc | aac | tgg | tac | gtg | aat | ggc | gcc | gag | gtg | cac | 2979 |
| Asp | Pro | Asp | Val | Lys | Phe | Asn | Trp | Tyr | Val | Asn | Gly | Ala | Glu | Val | His | |
| | | 335 | | | | | 340 | | | | | 345 | | | | |

| | | | | | | | | | | | | | | | | |
|---|---|---|---|---|---|---|---|---|---|---|---|---|---|---|---|---|
| cat | gct | cag | act | aaa | cca | cgc | gaa | acc | cag | tat | aat | agt | aca | tac | cga | 3027 |
| His | Ala | Gln | Thr | Lys | Pro | Arg | Glu | Thr | Gln | Tyr | Asn | Ser | Thr | Tyr | Arg | |
| | 350 | | | | | 355 | | | | | 360 | | | | | |

```
gtc gtg tca gtc ctg aca gtg act cac cag gat tgg ctg aac ggc aag      3075
Val Val Ser Val Leu Thr Val Thr His Gln Asp Trp Leu Asn Gly Lys
365                 370                 375                 380 gag tat acc tgc aag gtg tct aac aag gcc ctg ccc gcc cct atc cag      3123
Glu Tyr Thr Cys Lys Val Ser Asn Lys Ala Leu Pro Ala Pro Ile Gln
            385                 390                 395 aaa aca att agc aag gac aaa ggg cag cca cgg gaa ccc cag gtg tac      3171
Lys Thr Ile Ser Lys Asp Lys Gly Gln Pro Arg Glu Pro Gln Val Tyr
400                 405                 410 act ctg cca ccc tca aga gag gaa ctg act aag aac cag gtc agc ctg      3219
Thr Leu Pro Pro Ser Arg Glu Glu Leu Thr Lys Asn Gln Val Ser Leu
        415                 420                 425 acc tgt ctg gtg aaa ggc ttc tac ccc agc gat atc gtc gtg gag tgg      3267
Thr Cys Leu Val Lys Gly Phe Tyr Pro Ser Asp Ile Val Val Glu Trp
        430                 435                 440 gaa agt tca ggc cag cct gag aat act tac aag act acc cct cca gtg      3315
Glu Ser Ser Gly Gln Pro Glu Asn Thr Tyr Lys Thr Thr Pro Pro Val
445                 450                 455                 460 ctg gat agc gac ggg tcc tat ttc ctg tac agc aag ctg aca gtg gac      3363
Leu Asp Ser Asp Gly Ser Tyr Phe Leu Tyr Ser Lys Leu Thr Val Asp
                465                 470                 475 aaa tcc cgc tgg cag cag gga aac gtc ttt tcc tgt tct gtg atg cat      3411
Lys Ser Arg Trp Gln Gln Gly Asn Val Phe Ser Cys Ser Val Met His
            480                 485                 490 gag gcc ctg cac aat cat tac acc cag aag agt ctg tca ctg agc ccc      3459
Glu Ala Leu His Asn His Tyr Thr Gln Lys Ser Leu Ser Leu Ser Pro
            495                 500                 505 ggc aaa tgaggtacct ctagagtcga cccgggcggc ctcgaggacg gggtgaacta      3515
Gly Lys
    510 cgcctgagga tccgatcttt ttccctctgc caaaaattat ggggacatca tgaagcccct      3575 tgagcatctg acttctggct aataaaggaa atttattttc attgcaatag tgtgttggaa      3635 ttttttgtgt ctctcactcg gaagcaattc gttgatctga atttcgacca cccataatac      3695 ccattaccct ggtagataag tagcatggcg ggttaatcat taactacaag gaacccctag      3755 tgatggagtt ggccactccc tctctgcgcg ctcgctcgct cactgaggcc gggcgaccaa      3815 aggtcgcccg acgcccgggc tttgcccggg cggcctcagt gagcgagcga gcgcgcagcc      3875 ttaattaacc taattcactg gccgtcgttt tacaacgtcg tgactgggaa accctggcg      3935 ttacccaact aatcgccctt gcagcacatc cccctttcgc cagctggcgt aatagcgaag      3995 aggcccgcac cgatcgccct tcccaacagt tgcgcagcct gaatggcgaa tgggacgcgc      4055 cctgtagcgg cgcattaagc gcggcgggtg tggtggttac gcgcagcgtg accgctacac      4115 ttgccagcgc cctagcgccc gctcctttcg ctttcttccc ttcctttctc gccacgttcg      4175 ccggctttcc ccgtcaagct ctaaatcggg ggctccctt agggttccga tttagtgctt      4235 tacggcacct cgaccccaaa aaacttgatt agggtgatgg ttcacgtagt gggccatcgc      4295 cctgatagac ggtttttcgc cctttgacgt tggagtccac gttctttaat agtggactct      4355 tgttccaaac tggaacaaca ctcaacccta tctcggtcta ttcttttgat ttataaggga      4415 ttttgccgat ttcggcctat tggttaaaaa atgagctgat ttaacaaaaa tttaacgcga      4475 attttaacaa aatattaacg cttacaattt aggtggcact tttcggggaa atgtgcgcgg      4535 aaccccctatt tgtttatttt tctaaataca ttcaaatatg tatccgctca tgagacaata      4595 accctgataa atgcttcaat aatattgaaa aaggaagagt atgagtattc aactttccg      4655 tgtcgccctt attccctttt ttgcggcatt ttgccttcct gtttttgctc acccagaaac      4715
```

-continued

```
gctggtgaaa gtaaaagatg ctgaagatca gttgggtgca cgagtgggtt acatcgaact    4775
ggatctcaac agcggtaaga tccttgagag ttttcgcccc gaagaacgtt ttccaatgat    4835
gagcactttt aaagttctgc tatgtggcgc ggtattatcc cgtattgacg ccgggcaaga    4895
gcaactcggt cgccgcatac actattctca gaatgacttg gttgagtact caccagtcac    4955
agaaaagcat cttacggatg gcatgacagt aagagaatta tgcagtgctg ccataaccat    5015
gagtgataac actgcggcca acttacttct gacaacgatc ggaggaccga aggagctaac    5075 cgctttttg cacaacatgg gggatcatgt aactcgcctt gatcgttggg aaccggagct    5135
gaatgaagcc ataccaaacg acgagcgtga caccacgatg cctgtagcaa tggcaacaac    5195
gttgcgcaaa ctattaactg gcgaactact tactctagct tcccggcaac aattaataga    5255
ctggatggag gcggataaag ttgcaggacc acttctgcgc tcggcccttc cggctggctg    5315
gtttattgct gataaatctg gagccggtga gcgtgggtct cgcggtatca ttgcagcact    5375
ggggccagat ggtaagccct cccgtatcgt agttatctac acgacgggga gtcaggcaac    5435 tatgatgaa cgaaatagac agatcgctga gataggtgcc tcactgatta gcattggta    5495 actgtcagac caagtttact catatatact ttagattgat ttaaaacttc attttaatt    5555 taaaaggatc taggtgaaga tccttttga taatctcatg accaaaatcc cttaacgtga    5615
gttttcgttc cactgagcgt cagacccgt agaaaagatc aaaggatctt cttgagatcc    5675 ttttttctg cgcgtaatct gctgcttgca acaaaaaaa ccaccgctac cagcggtggt    5735
ttgtttgccg gatcaagagc taccaactct ttttccgaag gtaactggct tcagcagagc    5795
gcagatacca atactgttc ttctagtgta gccgtagtta ggccaccact tcaagaactc    5855
tgtagcaccg cctacatacc tcgctctgct aatcctgtta ccagtggctg ctgccagtgg    5915
cgataagtcg tgtcttaccg ggttggactc aagacgatag ttaccggata aggcgcagcg    5975
gtcgggctga acgggggggtt cgtgcacaca gcccagcttg gagcgaacga cctacaccga    6035
actgagatac ctacagcgtg agctatgaga aagcgccacg cttcccgaag ggagaaaggc    6095
ggacaggtat ccggtaagcg gcagggtcgg aacaggagag cgcacgaggg agcttccagg    6155
gggaaacgcc tggtatcttt atagtcctgt cgggtttcgc cacctctgac ttgagcgtcg    6215
atttttgtga tgctcgtcag ggggcggag cctatggaaa aacgccagca acgcggcctt    6275
tttacggttc ctggccttt gctggccttt tgctcacatg ttctttcctg cgttatcccc    6335
tgattctgtg gataaccgta ttaccgcctt tgagtgagct gataccgctc gccgcagccg    6395
aacgaccgag cgcagcgagt cagtgagcga ggaagcggaa gagcgcccaa tacgcaaacc    6455
gcctctcccc gcgcgttggc cgattcatta atgcagctgg cacgacaggt ttcccgactg    6515
gaaagcgggc agtgagcgca acgcaattaa tgtgagttag ctcactcatt aggcacccca    6575
ggctttacac tttatgcttc cggctcgtat gttgtgtgga attgtgagcg gataacaatt    6635
tcacacagga aacagctatg accatgatta cgccagattt aattaaggcc ttaattagg    6694
```

<210> SEQ ID NO 8
<211> LENGTH: 510
<212> TYPE: PRT
<213> ORGANISM: Artificial sequence
<220> FEATURE:
<223> OTHER INFORMATION: Synthetic Construct

<400> SEQUENCE: 8

```
Met Glu Phe Gly Leu Ser Trp Val Phe Leu Val Ala Leu Leu Lys Gly
1               5                   10                  15

Val Gln Cys Glu Val Gln Leu Leu Glu Ser Gly Pro Gly Leu Val Lys
            20                  25                  30

Pro Ser Glu Thr Leu Ser Leu Thr Cys Ala Val Ser Gly Leu Ser Ile
        35                  40                  45

Ser Ser Asp Phe Ser Trp Ala Trp Ile Arg Gln Thr Pro Gly Lys Ala
    50                  55                  60

Leu Glu Tyr Val Gly Tyr Ile Arg Gly Asn Thr Gly Asp Thr Tyr Tyr
65                  70                  75                  80

Asn Pro Ser Leu Lys Ser Arg Leu Thr Ile Ser Lys Asp Thr Ser Lys
                85                  90                  95

Asn Gln Ile Tyr Leu Asn Leu Ser Val Thr Ala Gly Asp Ala Ala
            100                 105                 110

Val Tyr Tyr Cys Ala Arg Asp Arg Val Cys Asp Asp Tyr Gly Tyr
        115                 120                 125

Tyr Tyr Thr Glu Val Cys Phe Gly Leu Asp Ser Trp Gly Gln Gly Ile
130                 135                 140

Val Val Thr Val Ser Ser Gly Gly Gly Gly Ser Gly Gly Gly Gly Ser
145                 150                 155                 160

Gly Gly Gly Gly Ser Ala Glu Leu Val Met Thr Gln Ser Pro Leu Ser
                165                 170                 175

Leu Ser Val Ala Pro Gly Gln Thr Ala Ser Ile Ser Cys Arg Ser Ser
                180                 185                 190

Gln Ser Leu Asp Tyr Ala Asn Gly Asn Thr Tyr Leu Ser Trp Phe His
        195                 200                 205

Gln Arg Pro Gly Gln Pro Pro Arg Arg Leu Ile Tyr Gln Ile Ser Asn
    210                 215                 220

Arg Asp Ser Gly Val Pro Asp Arg Phe Ser Gly Ser Gly Ala Gly Thr
225                 230                 235                 240

Glu Phe Thr Leu Arg Ile Ser Arg Met Glu Ser Asp Asp Val Gly Ile
                245                 250                 255

Tyr Tyr Cys Gly Gln Gly Thr Thr Phe Pro Arg Thr Phe Gly Gln Gly
            260                 265                 270

Thr Lys Val Glu Ile Lys Thr Cys Gly Gly Ser Lys Pro Pro Thr
        275                 280                 285

Cys Pro Pro Cys Thr Ser Pro Glu Leu Leu Gly Pro Ser Val Phe
    290                 295                 300

Leu Phe Pro Pro Lys Pro Lys Asp Thr Leu Met Ala Ser Arg Thr Pro
305                 310                 315                 320

Glu Val Thr Cys Val Val Val Asp Val Ser Gln Glu Asp Pro Asp Val
                325                 330                 335

Lys Phe Asn Trp Tyr Val Asn Gly Ala Glu Val His His Ala Gln Thr
            340                 345                 350

Lys Pro Arg Glu Thr Gln Tyr Asn Ser Thr Tyr Arg Val Val Ser Val
        355                 360                 365

Leu Thr Val Thr His Gln Asp Trp Leu Asn Gly Lys Glu Tyr Thr Cys
    370                 375                 380

Lys Val Ser Asn Lys Ala Leu Pro Ala Pro Ile Gln Lys Thr Ile Ser
385                 390                 395                 400

Lys Asp Lys Gly Gln Pro Arg Glu Pro Gln Val Tyr Thr Leu Pro Pro
                405                 410                 415
```

```
Ser Arg Glu Glu Leu Thr Lys Asn Gln Val Ser Leu Thr Cys Leu Val
                420                 425                 430

Lys Gly Phe Tyr Pro Ser Asp Ile Val Val Glu Trp Glu Ser Ser Gly
        435                 440                 445

Gln Pro Glu Asn Thr Tyr Lys Thr Thr Pro Pro Val Leu Asp Ser Asp
    450                 455                 460

Gly Ser Tyr Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
                485                 490                 495

Asn His Tyr Thr Gln Lys Ser Leu Ser Leu Ser Pro Gly Lys
            500                 505                 510

<210> SEQ ID NO 9
<211> LENGTH: 6694
<212> TYPE: DNA
<213> ORGANISM: Artificial sequence
<220> FEATURE:
<223> OTHER INFORMATION: engineered plasmid containining 201IA(H435)
      mutant
<220> FEATURE:
<221> NAME/KEY: misc_feature
<222> LOCATION: (275)..(404)
<223> OTHER INFORMATION: 3' ITR (complement)
<220> FEATURE:
<221> NAME/KEY: rep_origin
<222> LOCATION: (2198)..(2786)
<220> FEATURE:
<221> NAME/KEY: misc_feature
<222> LOCATION: (3226)..(3355)
<220> FEATURE:
<221> NAME/KEY: misc_feature
<222> LOCATION: (3423)..(3804)
<223> OTHER INFORMATION: CMV IE promoter
<220> FEATURE:
<221> NAME/KEY: promoter
<222> LOCATION: (3807)..(4088)
<223> OTHER INFORMATION: CB promoter
<220> FEATURE:
<221> NAME/KEY: TATA_signal
<222> LOCATION: (4061)..(4064)
<223> OTHER INFORMATION: rabbit globin polyA
<220> FEATURE:
<221> NAME/KEY: Intron
<222> LOCATION: (4183)..(5155)
<223> OTHER INFORMATION: chicken beta-actin intron
<220> FEATURE:
<221> NAME/KEY: CDS
<222> LOCATION: (5161)..(6690)
<223> OTHER INFORMATION: CMV IE promoter

<400> SEQUENCE: 9
gtacctctag agtcgacccg ggcggcctcg aggacggggt gaactacgcc tgaggatccg      60 atcttttttcc ctctgccaaa aattatgggg acatcatgaa gccccttgag catctgactt    120
ctggctaata aaggaaattt attttcattg caatagtgtg ttggaatttt ttgtgtctct    180
cactcggaag caattcgttg atctgaattt cgaccaccca taatacccat taccctggta    240
gataagtagc atggcgggtt aatcattaac tacaaggaac ccctagtgat ggagttggcc    300
actccctctc tgcgcgctcg ctcgctcact gaggccgggc gaccaaaggt cgcccgacgc    360
ccgggctttg cccgggcggc ctcagtgagc gagcgagcgc gcagccttaa ttaacctaat    420
tcactggccg tcgttttaca acgtcgtgac tgggaaaacc ctggcgttac ccaacttaat    480
cgccttgcag cacatccccc tttcgccagc tggcgtaata gcgaagaggc ccgcaccgat    540
cgcccttccc aacagttgcg cagcctgaat ggcgaatggg acgcgccctg tagcggcgca    600
```

| | |
|---|---|
| ttaagcgcgg cgggtgtggt ggttacgcgc agcgtgaccg ctacacttgc cagcgcccta | 660 |
| gcgcccgctc ctttcgcttt cttcccttcc tttctcgcca cgttcgccgg ctttccccgt | 720 |
| caagctctaa atcgggggct ccctttaggg ttccgattta gtgctttacg gcacctcgac | 780 |
| cccaaaaaac ttgattaggg tgatggttca cgtagtgggc catcgccctg atagacggtt | 840 |
| tttcgccctt tgacgttgga gtccacgttc tttaatagtg gactcttgtt ccaaactgga | 900 |
| acaacactca accctatctc ggtctattct tttgatttat aagggatttt gccgatttcg | 960 |
| gcctattggt taaaaatga gctgatttaa caaaaattta acgcgaattt taacaaaata | 1020 |
| ttaacgctta caatttaggt ggcacttttc ggggaaatgt gcgcggaacc cctatttgtt | 1080 |
| tatttttcta aatacattca aatatgtatc cgctcatgag acaataaccc tgataaatgc | 1140 |
| ttcaataata ttgaaaaagg aagagtatga gtattcaaca tttccgtgtc gcccttattc | 1200 |
| ccttttttgc ggcattttgc cttcctgttt ttgctcaccc agaaacgctg gtgaaagtaa | 1260 |
| aagatgctga agatcagttg ggtgcacgag tgggttacat cgaactggat ctcaacagcg | 1320 |
| gtaagatcct tgagagtttt cgccccgaag aacgttttcc aatgatgagc acttttaaag | 1380 |
| ttctgctatg tggcgcggta ttatcccgta ttgacgccgg gcaagagcaa ctcggtcgcc | 1440 |
| gcatacacta ttctcagaat gacttggttg agtactcacc agtcacagaa aagcatctta | 1500 |
| cggatggcat gacagtaaga gaattatgca gtgctgccat aaccatgagt gataacactg | 1560 |
| cggccaactt acttctgaca acgatcgag gaccgaagga gctaaccgct ttttgcaca | 1620 |
| acatggggga tcatgtaact cgccttgatc gttgggaacc ggagctgaat gaagccatac | 1680 |
| caaacgacga gcgtgacacc acgatgcctg tagcaatggc aacaacgttg cgcaaactat | 1740 |
| taactggcga actacttact ctagcttccc ggcaacaatt aatagactgg atggaggcgg | 1800 |
| ataaagttgc aggaccactt ctgcgctcgg cccttccggc tggctggttt attgctgata | 1860 |
| aatctggagc cggtgagcgt gggtctcgcg gtatcattgc agcactgggg ccagatggta | 1920 |
| agccctcccg tatcgtagtt atctacacga cggggagtca ggcaactatg gatgaacgaa | 1980 |
| atagacagat cgctgagata ggtgcctcac tgattaagca ttggtaactg tcagaccaag | 2040 |
| tttactcata tactttag attgatttaa aacttcattt ttaatttaaa aggatctagg | 2100 |
| tgaagatcct ttttgataat ctcatgacca aaatccctta acgtgagttt tcgttccact | 2160 |
| gagcgtcaga ccccgtagaa aagatcaaag gatcttcttg atcctttt tttctgcgcg | 2220 |
| taatctgctg cttgcaaaca aaaaaccac cgctaccagc ggtggtttgt ttgccggatc | 2280 |
| aagagctacc aactcttttt ccgaaggtaa ctggcttcag cagagcgcag ataccaaata | 2340 |
| ctgttcttct agtgtagccg tagttaggcc accacttcaa gaactctgta gcaccgccta | 2400 |
| catacctcgc tctgctaatc ctgttaccag tggctgctgc cagtggcgat aagtcgtgtc | 2460 |
| ttaccgggtt ggactcaaga cgatagttac cggataaggc gcagcggtcg ggctgaacgg | 2520 |
| ggggttcgtg cacacagccc agcttggagc gaacgaccta caccgaactg agatacctac | 2580 |
| agcgtgagct atgagaaagc gccacgcttc ccgaagggag aaaggcggac aggtatccgg | 2640 |
| taagcggcag ggtcggaaca ggagagcgca cgagggagct ccaggggga aacgcctggt | 2700 |
| atctttatag tcctgtcggg tttcgccacc tctgacttga gcgtcgattt ttgtgatgct | 2760 |
| cgtcaggggg gcggagccta tggaaaaacg ccagcaacgc ggccttttta cggttcctgg | 2820 |
| ccttttgctg gccttttgct cacatgttct ttcctgcgtt atcccctgat tctgtggata | 2880 |
| accgtattac cgcctttgag tgagctgata ccgctcgccg cagccgaacg accgagcgca | 2940 |
| gcgagtcagt gagcgaggaa gcggaagagc gcccaatacg caaaccgcct ctccccgcgc | 3000 |

```
gttggccgat tcattaatgc agctggcacg acaggtttcc cgactggaaa gcgggcagtg    3060
agcgcaacgc aattaatgtg agttagctca ctcattaggc accccaggct ttacacttta    3120
tgcttccggc tcgtatgttg tgtggaattg tgagcggata caatttcac acaggaaaca    3180 gctatgacca tgattacgcc agatttaatt aaggccttaa ttaggctgcg cgctcgctcg    3240
ctcactgagg ccgcccgggc aaagcccggg cgtcgggcga cctttggtcg cccggcctca    3300
gtgagcgagc gagcgcgcag agagggagtg gccaactcca tcactagggg ttccttgtag    3360
ttaatgatta acccgccatg ctacttatct accagggtaa tggggatcct ctagaactat    3420
agctagtcga cattgattat tgactagtta ttaatagtaa tcaattacgg ggtcattagt    3480
tcatagccca tatatggagt tccgcgttac ataacttacg gtaaatggcc cgcctggctg    3540
accgcccaac gacccccgcc cattgacgtc aataatgacg tatgttccca tagtaacgcc    3600
aatagggact ttccattgac gtcaatgggt ggactattta cggtaaactg cccacttggc    3660
agtacatcaa gtgtatcata tgccaagtac gccccctatt gacgtcaatg acggtaaatg    3720
gcccgcctgg cattatgccc agtacatgac cttatgggac tttcctactt ggcagtacat    3780
ctacgtatta gtcatcgcta ttaccatggt cgaggtgagc cccacgttct gcttcactct    3840
ccccatctcc ccccctccc caccccaat tttgtattta tttattttt aattattttg    3900 tgcagcgatg ggggcggggg gggggggggg gcgcgcgcca ggcggggcgg ggcggggcga    3960
ggggcggggc gggcgaggc ggagaggtgc ggcggcagcc aatcagagcg gcgcgctccg    4020
aaagtttcct tttatggcga ggcggcggcg gcggcggccc tataaaaagc gaagcgcgcg    4080
gcgggcgggg agtcgctgcg acgctgcctt cgccccgtgc cccgctccgc cgccgcctcg    4140
cgccgcccgc cccggctctg actgaccgcg ttactcccac aggtgagcgg gcgggacggc    4200
ccttctcctc cgggctgtaa ttagcgcttg gtttaatgac ggcttgtttc ttttctgtgg    4260
ctgcgtgaaa gccttgaggg gctccgggag ggccctttgt gcggggggag cggctcgggg    4320
ggtgcgtgcg tgtgtgtgtg cgtggggagc gccgcgtgcg gctccgcgct gcccggcggc    4380
tgtgagcgct gcgggcgcgg cgcggggctt tgtgcgctcc gcagtgtgcg cgaggggagc    4440
gcggccgggg gcggtgcccc gcggtgcggg ggggctgcg aggggaacaa aggctgcgtg    4500
cggggtgtgt gcgtggggg gtgagcaggg ggtgtgggcg cgtcggtcgg gctgcaaccc    4560 ccctgcacc cccctccccg agttgctgag cacggcccgg cttcgggtgc ggggctccgt    4620
acggggcgtg gcgcggggct cgccgtgccg ggcgggggt ggcggcaggt gggggtgccg    4680
ggcggggcgg ggccgcctcg ggccggggag ggctcggggg aggggcgcgg cggccccgg    4740 agcgccggcg gctgtcgagg cgcggcgagc cgcagccatt gccttttatg gtaatcgtgc    4800
gagagggcgc agggacttcc tttgtcccaa atctgtgcgg agccgaaatc tgggaggcgc    4860
cgccgcaccc cctctagcgg gcgcggggcg aagcggtgcg gcgccggcag gaaggaaatg    4920
ggcggggagg gccttcgtgc gtcgccgcgc cgccgtcccc ttctccctct ccagcctcgg    4980
ggctgtccgc ggggggacgg ctgccttcgg ggggacggg gcagggcggg gttcggcttc    5040
tggcgtgtga ccggcggctc tagagcctct gctaaccatg ttcatgcctt cttctttttc    5100
ctacagctcc tgggcaacgt gctggttatt gtgctgtctc atcattttgg caaagaattc    5160 atg gag ttc ggg ctg agc tgg gtc ttt ctg gtg gcc ctg ctg aag gga    5208
Met Glu Phe Gly Leu Ser Trp Val Phe Leu Val Ala Leu Leu Lys Gly
1               5                   10                  15 gtc cag tgc gag gtg cag ctg ctg gaa tcc gga cct ggc ctg gtg aaa    5256
Val Gln Cys Glu Val Gln Leu Leu Glu Ser Gly Pro Gly Leu Val Lys
            20                  25                  30
```

| | | |
|---|---|---|
| cca tct gag aca ctg agt ctg act tgt gct gtc tcc ggc ctg tct atc<br>Pro Ser Glu Thr Leu Ser Leu Thr Cys Ala Val Ser Gly Leu Ser Ile<br>35                           40                          45 | 5304 |
| agc tcc gat ttc tcc tgg gca tgg att agg cag acc ccc ggc aag gcc<br>Ser Ser Asp Phe Ser Trp Ala Trp Ile Arg Gln Thr Pro Gly Lys Ala<br>50                           55                         60 | 5352 |
| ctg gaa tat gtg ggg tac atc cgc ggg aac acc gga gat aca tac tat<br>Leu Glu Tyr Val Gly Tyr Ile Arg Gly Asn Thr Gly Asp Thr Tyr Tyr<br>65                           70                                  80 | 5400 |
| aat cct agt ctg aag tca agg ctg act atc tca aag gac acc agc aaa<br>Asn Pro Ser Leu Lys Ser Arg Leu Thr Ile Ser Lys Asp Thr Ser Lys<br>              85                         90                        95 | 5448 |
| aac caa atc tac ctg aat ctg tct agt gtc acc gct ggc gat gcc gcc<br>Asn Gln Ile Tyr Leu Asn Leu Ser Ser Val Thr Ala Gly Asp Ala Ala<br>             100                     105                     110 | 5496 |
| gtg tac tat tgc gca agg gac cgg gtg tgc gac gat gac tac gga tac<br>Val Tyr Tyr Cys Ala Arg Asp Arg Val Cys Asp Asp Asp Tyr Gly Tyr<br>115                       120                     125 | 5544 |
| tat tac acc gag gtg tgc ttc ggc ctg gat tct tgg ggg cag gga atc<br>Tyr Tyr Thr Glu Val Cys Phe Gly Leu Asp Ser Trp Gly Gln Gly Ile<br>130                       135                     140 | 5592 |
| gtg gtc aca gtg tca agc ggc gga gga ggc agc gga gga gga ggg tcc<br>Val Val Thr Val Ser Ser Gly Gly Gly Gly Ser Gly Gly Gly Gly Ser<br>145                       150                     155                     160 | 5640 |
| gga ggc ggg gga tct gca gaa ctg gtc atg aca cag tcc cca ctg agc<br>Gly Gly Gly Gly Ser Ala Glu Leu Val Met Thr Gln Ser Pro Leu Ser<br>             165                     170                     175 | 5688 |
| ctg tcc gtc gct cca gga cag act gca tct att agt tgt cga tcc tct<br>Leu Ser Val Ala Pro Gly Gln Thr Ala Ser Ile Ser Cys Arg Ser Ser<br>180                       185                     190 | 5736 |
| cag tcc ctg gac tat gct aac ggc aat acc tac ctg tct tgg ttt cac<br>Gln Ser Leu Asp Tyr Ala Asn Gly Asn Thr Tyr Leu Ser Trp Phe His<br>             195                     200                     205 | 5784 |
| cag cga cca gga cag cca cct cgg aga ctg atc tat cag att tcc aac<br>Gln Arg Pro Gly Gln Pro Pro Arg Arg Leu Ile Tyr Gln Ile Ser Asn<br>210                       215                     220 | 5832 |
| aga gat tct gga gtg ccc gac agg ttc tca ggc agc gga gca gga act<br>Arg Asp Ser Gly Val Pro Asp Arg Phe Ser Gly Ser Gly Ala Gly Thr<br>225                       230                     235                     240 | 5880 |
| gag ttt acc ctg cga atc agt cgg atg gaa tca gat gac gtg ggg atc<br>Glu Phe Thr Leu Arg Ile Ser Arg Met Glu Ser Asp Asp Val Gly Ile<br>             245                     250                     255 | 5928 |
| tac tac tgc gga cag ggg acc aca ttc cca cgg aca ttt gga cag ggc<br>Tyr Tyr Cys Gly Gln Gly Thr Thr Phe Pro Arg Thr Phe Gly Gln Gly<br>260                       265                     270 | 5976 |
| act aag gtg gag atc aaa acc tgt gga gga gga agc aag cca cca acc<br>Thr Lys Val Glu Ile Lys Thr Cys Gly Gly Gly Ser Lys Pro Pro Thr<br>275                       280                     285 | 6024 |
| tgc cct cca tgt aca tct ccc gaa ctg ctg ggc ggg cct agc gtg ttc<br>Cys Pro Pro Cys Thr Ser Pro Glu Leu Leu Gly Gly Pro Ser Val Phe<br>290                       295                     300 | 6072 |
| ctg ttt ccc cct aag cct aaa gat aca ctg atg att agt aga acc cca<br>Leu Phe Pro Pro Lys Pro Lys Asp Thr Leu Met Ile Ser Arg Thr Pro<br>305                       310                     315                     320 | 6120 |
| gag gtc aca tgc gtg gtc gtg gac gtg tcc cag gaa gat cct gac gtg<br>Glu Val Thr Cys Val Val Asp Val Ser Gln Glu Asp Pro Asp Val<br>             325                     330                     335 | 6168 |
| aag ttc aac tgg tac gtg aat ggc gcc gag gtg cac cat gct cag act<br>Lys Phe Asn Trp Tyr Val Asn Gly Ala Glu Val His His Ala Gln Thr<br>340                       345                     350 | 6216 |

-continued

| | | |
|---|---|---|
| aaa cca cgc gaa acc cag tat aat agt aca tac cga gtc gtg tca gtc<br>Lys Pro Arg Glu Thr Gln Tyr Asn Ser Thr Tyr Arg Val Val Ser Val<br>    355                 360                 365 | 6264 |
| ctg aca gtg act cac cag gat tgg ctg aac ggc aag gag tat acc tgc<br>Leu Thr Val Thr His Gln Asp Trp Leu Asn Gly Lys Glu Tyr Thr Cys<br>370                 375                 380 | 6312 |
| aag gtg tct aac aag gcc ctg ccc gcc cct atc cag aaa aca att agc<br>Lys Val Ser Asn Lys Ala Leu Pro Ala Pro Ile Gln Lys Thr Ile Ser<br>385                 390                 395                 400 | 6360 |
| aag gac aaa ggg cag cca cgg gaa ccc cag gtg tac act ctg cca ccc<br>Lys Asp Lys Gly Gln Pro Arg Glu Pro Gln Val Tyr Thr Leu Pro Pro<br>            405                 410                 415 | 6408 |
| tca aga gag gaa ctg act aag aac cag gtc agc ctg acc tgt ctg gtg<br>Ser Arg Glu Glu Leu Thr Lys Asn Gln Val Ser Leu Thr Cys Leu Val<br>        420                 425                 430 | 6456 |
| aaa ggc ttc tac ccc agc gat atc gtc gtg gag tgg gaa agt tca ggc<br>Lys Gly Phe Tyr Pro Ser Asp Ile Val Val Glu Trp Glu Ser Ser Gly<br>    435                 440                 445 | 6504 |
| cag cct gag aat act tac aag act acc cct cca gtg ctg gat agc gac<br>Gln Pro Glu Asn Thr Tyr Lys Thr Thr Pro Pro Val Leu Asp Ser Asp<br>450                 455                 460 | 6552 |
| ggg tcc tat ttc ctg tac agc aag ctg aca gtg gac aaa tcc cgc tgg<br>Gly Ser Tyr Phe Leu Tyr Ser Lys Leu Thr Val Asp Lys Ser Arg Trp<br>465                 470                 475                 480 | 6600 |
| cag cag gga aac gtc ttt tcc tgt tct gtg atg cat gag gcc ctg cac<br>Gln Gln Gly Asn Val Phe Ser Cys Ser Val Met His Glu Ala Leu His<br>            485                 490                 495 | 6648 |
| aat gct tac acc cag aag agt ctg tca ctg agc ccc ggc aaa tgag<br>Asn Ala Tyr Thr Gln Lys Ser Leu Ser Leu Ser Pro Gly Lys<br>        500                 505                 510 | 6694 |

<210> SEQ ID NO 10
<211> LENGTH: 510
<212> TYPE: PRT
<213> ORGANISM: Artificial sequence
<220> FEATURE:
<223> OTHER INFORMATION: Synthetic Construct

<400> SEQUENCE: 10

Met Glu Phe Gly Leu Ser Trp Val Phe Leu Val Ala Leu Leu Lys Gly
1               5                   10                  15

Val Gln Cys Glu Val Gln Leu Leu Glu Ser Gly Pro Gly Leu Val Lys
            20                  25                  30

Pro Ser Glu Thr Leu Ser Leu Thr Cys Ala Val Ser Gly Leu Ser Ile
        35                  40                  45

Ser Ser Asp Phe Ser Trp Ala Trp Ile Arg Gln Thr Pro Gly Lys Ala
    50                  55                  60

Leu Glu Tyr Val Gly Tyr Ile Arg Gly Asn Thr Gly Asp Thr Tyr Tyr
65                  70                  75                  80

Asn Pro Ser Leu Lys Ser Arg Leu Thr Ile Ser Lys Asp Thr Ser Lys
                85                  90                  95

Asn Gln Ile Tyr Leu Asn Leu Ser Ser Val Thr Ala Gly Asp Ala Ala
            100                 105                 110

Val Tyr Tyr Cys Ala Arg Asp Arg Val Cys Asp Asp Tyr Gly Tyr
        115                 120                 125

Tyr Tyr Thr Glu Val Cys Phe Gly Leu Asp Ser Trp Gly Gln Gly Ile
    130                 135                 140

Val Val Thr Val Ser Ser Gly Gly Gly Gly Ser Gly Gly Gly Gly Ser
145                 150                 155                 160

```
Gly Gly Gly Gly Ser Ala Glu Leu Val Met Thr Gln Ser Pro Leu Ser
            165                 170                 175
Leu Ser Val Ala Pro Gly Gln Thr Ala Ser Ile Ser Cys Arg Ser Ser
        180                 185                 190
Gln Ser Leu Asp Tyr Ala Asn Gly Asn Thr Tyr Leu Ser Trp Phe His
    195                 200                 205
Gln Arg Pro Gly Gln Pro Pro Arg Leu Ile Tyr Gln Ile Ser Asn
210                 215                 220
Arg Asp Ser Gly Val Pro Asp Arg Phe Ser Gly Ser Gly Ala Gly Thr
225                 230                 235                 240
Glu Phe Thr Leu Arg Ile Ser Arg Met Glu Ser Asp Asp Val Gly Ile
            245                 250                 255
Tyr Tyr Cys Gly Gln Gly Thr Thr Phe Pro Arg Thr Phe Gly Gln Gly
        260                 265                 270
Thr Lys Val Glu Ile Lys Thr Cys Gly Gly Ser Lys Pro Pro Thr
    275                 280                 285
Cys Pro Pro Cys Thr Ser Pro Glu Leu Leu Gly Pro Ser Val Phe
290                 295                 300
Leu Phe Pro Pro Lys Pro Lys Asp Thr Leu Met Ile Ser Arg Thr Pro
305                 310                 315                 320
Glu Val Thr Cys Val Val Val Asp Val Ser Gln Glu Asp Pro Asp Val
            325                 330                 335
Lys Phe Asn Trp Tyr Val Asn Gly Ala Glu Val His His Ala Gln Thr
        340                 345                 350
Lys Pro Arg Glu Thr Gln Tyr Asn Ser Thr Tyr Arg Val Val Ser Val
    355                 360                 365
Leu Thr Val Thr His Gln Asp Trp Leu Asn Gly Lys Glu Tyr Thr Cys
370                 375                 380
Lys Val Ser Asn Lys Ala Leu Pro Ala Pro Ile Gln Lys Thr Ile Ser
385                 390                 395                 400
Lys Asp Lys Gly Gln Pro Arg Glu Pro Gln Val Tyr Thr Leu Pro Pro
            405                 410                 415
Ser Arg Glu Glu Leu Thr Lys Asn Gln Val Ser Leu Thr Cys Leu Val
        420                 425                 430
Lys Gly Phe Tyr Pro Ser Asp Ile Val Val Glu Trp Glu Ser Ser Gly
    435                 440                 445
Gln Pro Glu Asn Thr Tyr Lys Thr Thr Pro Pro Val Leu Asp Ser Asp
450                 455                 460
Gly Ser Tyr Phe Leu Tyr Ser Lys Leu Thr Val Asp Lys Ser Arg Trp
465                 470                 475                 480
Gln Gln Gly Asn Val Phe Ser Cys Ser Val Met His Glu Ala Leu His
            485                 490                 495
Asn Ala Tyr Thr Gln Lys Ser Leu Ser Leu Ser Pro Gly Lys
        500                 505                 510

<210> SEQ ID NO 11
<211> LENGTH: 7284
<212> TYPE: DNA
<213> ORGANISM: Artificial Sequence
<220> FEATURE:
<223> OTHER INFORMATION: Plasmid containing the heavy and light chains
      of trastuzumab
<220> FEATURE:
<221> NAME/KEY: misc_feature
<222> LOCATION: (1)..(130)
<223> OTHER INFORMATION: 5' ITR
```

```
<220> FEATURE:
<221> NAME/KEY: promoter
<222> LOCATION: (191)..(932)
<223> OTHER INFORMATION: human CMV IE enhancer and promoter
<220> FEATURE:
<221> NAME/KEY: TATA_signal
<222> LOCATION: (897)..(901)
<220> FEATURE:
<221> NAME/KEY: Intron
<222> LOCATION: (1047)..(1179)
<220> FEATURE:
<221> NAME/KEY: sig_peptide
<222> LOCATION: (1305)..(1364)
<223> OTHER INFORMATION: IL-2 signal peptide
<220> FEATURE:
<221> NAME/KEY: CDS
<222> LOCATION: (1365)..(1724)
<223> OTHER INFORMATION: Trastuzumab heavy variable
<220> FEATURE:
<221> NAME/KEY: CDS
<222> LOCATION: (1725)..(2720)
<223> OTHER INFORMATION: trastuzumab heavy constant
<220> FEATURE:
<221> NAME/KEY: enhancer
<222> LOCATION: (2726)..(3313)
<223> OTHER INFORMATION: IRES
<220> FEATURE:
<221> NAME/KEY: sig_peptide
<222> LOCATION: (3314)..(3373)
<223> OTHER INFORMATION: IL2 signal peptide
<220> FEATURE:
<221> NAME/KEY: CDS
<222> LOCATION: (3374)..(3694)
<223> OTHER INFORMATION: trastuzumab light variable
<220> FEATURE:
<221> NAME/KEY: CDS
<222> LOCATION: (3695)..(4021)
<223> OTHER INFORMATION: trastuzumab constant light (kappa)
<220> FEATURE:
<221> NAME/KEY: polyA_signal
<222> LOCATION: (4038)..(4269)
<223> OTHER INFORMATION: SV40 late polyA signal
<220> FEATURE:
<221> NAME/KEY: polyA_signal
<222> LOCATION: (4083)..(4269)
<223> OTHER INFORMATION: SV40 late polyA signal
<220> FEATURE:
<221> NAME/KEY: misc_feature
<222> LOCATION: (4334)..(4463)
<223> OTHER INFORMATION: 3' ITR (complement)
<220> FEATURE:
<221> NAME/KEY: rep_origin
<222> LOCATION: (4640)..(5095))
<220> FEATURE:
<221> NAME/KEY: CDS
<222> LOCATION: (5226)..(6083)
<223> OTHER INFORMATION: amp-R
<220> FEATURE:
<221> NAME/KEY: misc_feature
<222> LOCATION: (6257)..(6845)
<223> OTHER INFORMATION: COL/E1/origin

<400> SEQUENCE: 11
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gccatgctct     180
aggaagatct tcaatattgg ccattagcca tattattcat tggttatata gcataaatca     240
atattggcta ttggccattg catacgttgt atctatatca taatatgtac atttatattg     300
gctcatgtcc aatatgaccg ccatgttggc attgattatt gactagttat taatagtaat     360
caattacggg gtcattagtt catagcccat atatggagtt ccgcgttaca taacttacgg     420
taaatggccc gcctggctga ccgcccaacg acccccgccc attgacgtca ataatgacgt     480
```

-continued

| | |
|---|---|
| atgttcccat agtaacgcca atagggactt tccattgacg tcaatgggtg gagtatttac | 540 |
| ggtaaactgc ccacttggca gtacatcaag tgtatcatat gccaagtccg cccctattg | 600 |
| acgtcaatga cggtaaatgg cccgcctggc attatgccca gtacatgacc ttacgggact | 660 |
| ttcctacttg gcagtacatc tacgtattag tcatcgctat taccatggtg atgcggtttt | 720 |
| ggcagtacac caatgggcgt ggatagcggt ttgactcacg gggatttcca agtctccacc | 780 |
| ccattgacgt caatgggagt ttgttttggc accaaaatca acgggacttt ccaaaatgtc | 840 |
| gtaataaccc cgccccgttg acgcaaatgg gcggtaggcg tgtacggtgg gaggtctata | 900 |
| taagcagagc tcgtttagtg aaccgtcaga tcactagaag ctttattgcg gtagtttatc | 960 |
| acagttaaat tgctaacgca gtcagtgctt ctgacacaac agtctcgaac ttaagctgca | 1020 |
| gaagttggtc gtgaggcact gggcaggtaa gtatcaaggt tacaagacag gtttaaggag | 1080 |
| accaatagaa actgggcttg tcgagacaga gaagactctt gcgtttctga taggcaccta | 1140 |
| ttggtcttac tgacatccac tttgcctttc tctccacagg tgtccactcc cagttcaatt | 1200 |
| acagctctta aggctagagt acttaatacg actcactata ggctagcggg actttgcac | 1260 |
| tggaacttac aacacccgag caaggacgcg actctagacc caccatgtac cggatgcagc | 1320 |

```
tgctgagctg tatcgccctg tctctggccc tcgtgaccaa cagc gaa gtg cag ctg   1376
                                              Glu Val Gln Leu
                                                1
gtg gaa agc ggc gga gga ctg gtg cag cct ggc gga tct ctg aga ctg   1424
Val Glu Ser Gly Gly Gly Leu Val Gln Pro Gly Gly Ser Leu Arg Leu
 5                  10                  15                  20
agc tgt gcc gcc agc ggc ttc aac atc aag gac acc tac atc cac tgg   1472
Ser Cys Ala Ala Ser Gly Phe Asn Ile Lys Asp Thr Tyr Ile His Trp
                 25                  30                  35
gtg cgc cag gcc cct ggc aag gga ctg gaa tgg gtg gcc aga atc tac   1520
Val Arg Gln Ala Pro Gly Lys Gly Leu Glu Trp Val Ala Arg Ile Tyr
         40                  45                  50
ccc acc aac ggc tac acc aga tac gcc gac agc gtg aag ggc cgg ttc   1568
Pro Thr Asn Gly Tyr Thr Arg Tyr Ala Asp Ser Val Lys Gly Arg Phe
             55                  60                  65
acc atc agc gcc gac acc agc aag aac acc gcc tac ctg cag atg aac   1616
Thr Ile Ser Ala Asp Thr Ser Lys Asn Thr Ala Tyr Leu Gln Met Asn
 70                  75                  80
agc ctg cgg gcc gag gac acc gcc gtg tac tac tgt agt aga tgg gga   1664
Ser Leu Arg Ala Glu Asp Thr Ala Val Tyr Tyr Cys Ser Arg Trp Gly
 85                  90                  95                 100
ggc gac ggc ttc tac gcc atg gac tat tgg ggc cag ggc acc ctc gtg   1712
Gly Asp Gly Phe Tyr Ala Met Asp Tyr Trp Gly Gln Gly Thr Leu Val
                105                 110                 115
aca gtg tct agt gcg tcg acc aag ggg ccc tcg gtc ttc ccc ctg gca   1760
Thr Val Ser Ser Ala Ser Thr Lys Gly Pro Ser Val Phe Pro Leu Ala
                120                 125                 130
ccc tcc tcc aag agc acc tct ggg ggc aca gcg gcc ctg ggc tgc ctg   1808
Pro Ser Ser Lys Ser Thr Ser Gly Gly Thr Ala Ala Leu Gly Cys Leu
                135                 140                 145
gtc aag gac tac ttc ccc gaa ccg gtg acg gtg tcg tgg aac tca ggc   1856
Val Lys Asp Tyr Phe Pro Glu Pro Val Thr Val Ser Trp Asn Ser Gly
    150                 155                 160
gcc ctg acc agc ggc gtg cac acc ttc ccg gct gtc cta cag tcc tca   1904
Ala Leu Thr Ser Gly Val His Thr Phe Pro Ala Val Leu Gln Ser Ser
165                 170                 175                 180
gga ctc tac tcc ctc agc agc gtg gtg acc gtg ccc tcc agc agc ttg   1952
Gly Leu Tyr Ser Leu Ser Ser Val Val Thr Val Pro Ser Ser Ser Leu
                185                 190                 195
```

|  |  |
|---|---|
| ggc acc cag acc tac atc tgc aac gtg aat cac aag ccc agc aac acc<br>Gly Thr Gln Thr Tyr Ile Cys Asn Val Asn His Lys Pro Ser Asn Thr<br>200 205 210 | 2000 |
| aag gtg gac aag aaa gtt gag ccc aaa tct tgt gac aaa act cac aca<br>Lys Val Asp Lys Lys Val Glu Pro Lys Ser Cys Asp Lys Thr His Thr<br>215 220 225 | 2048 |
| tgc cca ccg tgc cca gca cct gaa ctc ctg ggg gga ccg tca gtc ttc<br>Cys Pro Pro Cys Pro Ala Pro Glu Leu Leu Gly Gly Pro Ser Val Phe<br>230 235 240 | 2096 |
| ctc ttc ccc cca aaa ccc aag gac acc ctc atg atc tcc cgg acc cct<br>Leu Phe Pro Pro Lys Pro Lys Asp Thr Leu Met Ile Ser Arg Thr Pro<br>245 250 255 260 | 2144 |
| gag gtc aca tgc gtg gtg gtg gac gtg agc cac gaa gac cct gag gtc<br>Glu Val Thr Cys Val Val Val Asp Val Ser His Glu Asp Pro Glu Val<br>265 270 275 | 2192 |
| aag ttc aac tgg tac gtg gac ggc gtg gag gtg cat aat gcc aag aca<br>Lys Phe Asn Trp Tyr Val Asp Gly Val Glu Val His Asn Ala Lys Thr<br>280 285 290 | 2240 |
| aag ccg cgg gag gag cag tac aac agc acg tac cgt gtg gtc agc gtc<br>Lys Pro Arg Glu Glu Gln Tyr Asn Ser Thr Tyr Arg Val Val Ser Val<br>295 300 305 | 2288 |
| ctc acc gtc ctg cac cag gac tgg ctg aat ggc aag gag tac aag tgc<br>Leu Thr Val Leu His Gln Asp Trp Leu Asn Gly Lys Glu Tyr Lys Cys<br>310 315 320 | 2336 |
| aag gtc tcc aac aaa gcc ctc cca gcc ccc atc gag aaa acc atc tcc<br>Lys Val Ser Asn Lys Ala Leu Pro Ala Pro Ile Glu Lys Thr Ile Ser<br>325 330 335 340 | 2384 |
| aaa gcc aaa ggg cag ccc cga gaa cca cag gtg tac acc ctg ccc cca<br>Lys Ala Lys Gly Gln Pro Arg Glu Pro Gln Val Tyr Thr Leu Pro Pro<br>345 350 355 | 2432 |
| tcc cgg gat gag ctg acc aag aac cag gtc agc ctg acc tgc ctg gtc<br>Ser Arg Asp Glu Leu Thr Lys Asn Gln Val Ser Leu Thr Cys Leu Val<br>360 365 370 | 2480 |
| aaa ggc ttc tat ccc agc gac atc gcc gtg gag tgg gag agc aat ggg<br>Lys Gly Phe Tyr Pro Ser Asp Ile Ala Val Glu Trp Glu Ser Asn Gly<br>375 380 385 | 2528 |
| cag ccg gag aac aac tac aag acc acg cct ccc gtg ctg gac tcc gac<br>Gln Pro Glu Asn Asn Tyr Lys Thr Thr Pro Pro Val Leu Asp Ser Asp<br>390 395 400 | 2576 |
| ggc tcc ttc ttc ctc tac agc aag ctc acc gtg gac aag agc agg tgg<br>Gly Ser Phe Phe Leu Tyr Ser Lys Leu Thr Val Asp Lys Ser Arg Trp<br>405 410 415 420 | 2624 |
| cag cag ggg aac gtc ttc tca tgc tcc gtg atg cat gag gct ctg cac<br>Gln Gln Gly Asn Val Phe Ser Cys Ser Val Met His Glu Ala Leu His<br>425 430 435 | 2672 |
| aac cac tac acg cag aag agc ctc tcc ctg tct ccc ggc aag tga taa<br>Asn His Tyr Thr Gln Lys Ser Leu Ser Leu Ser Pro Gly Lys<br>440 445 450 | 2720 |
| ggccggcccc tctccctccc cccccccctaa cgttactggc cgaagccgct tggaataagg | 2780 |
| ccggtgtgcg tttgtctata tgttattttc caccatattg ccgtcttttg gcaatgtgag | 2840 |
| ggcccggaaa cctggccctg tcttcttgac gagcattcct aggggtcttt ccctctcgc | 2900 |
| caaaggaatg caaggtctgt tgaatgtcgt gaaggaagca gttcctctgg aagcttcttg | 2960 |
| aagacaaaca acgtctgtag cgacccttg caggcagcgg aacccccac ctggcgacag | 3020 |
| gtgcctctgc ggccaaaagc cacgtgtata agatacacct gcaaaggcgg cacaacccca | 3080 |
| gtgccacgtt gtgagttgga tagttgtgga aagagtcaaa tggctctcct caagcgtatt | 3140 |
| caacaagggg ctgaaggatg cccagaaggt accccattgt atgggatctg atctggggcc | 3200 |

```
                                          -continued
tcggtacaca tgctttacat gtgtttagtc gaggttaaaa aaacgtctag gccccccgaa   3260
ccacggggac gtggttttcc tttgaaaaac acgatgataa tatggccaca accatgtacc   3320
gcatgcaact cctgtcttgc attgcactaa gtcttgcact tgtcacaaac agt gat      3376
                                                          Asp atc cag atg acc cag agc ccc agc agc ctg tct gcc agc gtg ggc gac   3424
Ile Gln Met Thr Gln Ser Pro Ser Ser Leu Ser Ala Ser Val Gly Asp
        455                 460                 465 aga gtg acc atc acc tgt aga gcc agc cag gac gtg aac acc gcc gtg   3472
Arg Val Thr Ile Thr Cys Arg Ala Ser Gln Asp Val Asn Thr Ala Val
        470                 475                 480 gcc tgg tat cag cag aag cct ggc aag gcc ccc aag ctg ctg atc tac   3520
Ala Trp Tyr Gln Gln Lys Pro Gly Lys Ala Pro Lys Leu Leu Ile Tyr
    485                 490                 495 agc gcc agc ttc ctg tac agc ggc gtg ccc agc aga ttc agc ggc agc   3568
Ser Ala Ser Phe Leu Tyr Ser Gly Val Pro Ser Arg Phe Ser Gly Ser
500                 505                 510                 515 aga tcc ggc acc gac ttc acc ctg acc atc agc tcc ctg cag ccc gag   3616
Arg Ser Gly Thr Asp Phe Thr Leu Thr Ile Ser Ser Leu Gln Pro Glu
                520                 525                 530 gac ttc gcc acc tac tac tgc cag cag cac tac acc acc ccc ccc aca   3664
Asp Phe Ala Thr Tyr Tyr Cys Gln Gln His Tyr Thr Thr Pro Pro Thr
            535                 540                 545 ttt ggc cag ggc acc aag gtg gaa atc aag cgt acg gtg gct gca cca   3712
Phe Gly Gln Gly Thr Lys Val Glu Ile Lys Arg Thr Val Ala Ala Pro
        550                 555                 560 tct gtc ttc atc ttc ccg cca tct gat gag cag ttg aaa tct gga act   3760
Ser Val Phe Ile Phe Pro Pro Ser Asp Glu Gln Leu Lys Ser Gly Thr
565                 570                 575 gcc tct gtt gtg tgc ctg ctg aat aac ttc tac ccc aga gaa gcc aaa   3808
Ala Ser Val Val Cys Leu Leu Asn Asn Phe Tyr Pro Arg Glu Ala Lys
580                 585                 590                 595 gtg cag tgg aag gtg gac aac gcc ctg cag agc gga aac agc cag gaa   3856
Val Gln Trp Lys Val Asp Asn Ala Leu Gln Ser Gly Asn Ser Gln Glu
                600                 605                 610 agc gtg aca gag cag gat tcc aag gat tcc aca tac agc ctg agc agc   3904
Ser Val Thr Glu Gln Asp Ser Lys Asp Ser Thr Tyr Ser Leu Ser Ser
            615                 620                 625 aca ctg aca ctg tcc aag gcc gac tac gag aag cac aag gtg tac gcc   3952
Thr Leu Thr Leu Ser Lys Ala Asp Tyr Glu Lys His Lys Val Tyr Ala
        630                 635                 640 tgc gaa gtg aca cac cag gga ctg tcc tcc cct gtg aca aag agc ttc   4000
Cys Glu Val Thr His Gln Gly Leu Ser Ser Pro Val Thr Lys Ser Phe
    645                 650                 655 aac aga gga gaa tgc tga tga aagcttgcgg ccgcttcgag cagacatgat       4051
Asn Arg Gly Glu Cys
660 aagatacatt gatgagtttg gacaaaccac aactagaatg cagtgaaaaa aatgctttat   4111 ttgtgaaatt tgtgatgcta ttgctttatt tgtaaccatt ataagctgca ataaacaagt   4171 taacaacaac aattgcattc attttatgtt tcaggttcag ggggagatgt gggaggtttt   4231 ttaaagcaag taaaacctct acaaatgtgg taaaatcgat aaggatcttc ctagagcatg   4291 gctacgtaga taagtagcat ggcgggttaa tcattaacta caaggaaccc ctagtgatgg   4351 agttggccac tccctctctg cgcgctcgct cgctcactga ggccgggcga ccaaaggtcg   4411 cccgacgccc gggctttgcc cggcggcct cagtgagcga gcgagcgcgc agccttaatt   4471 aacctaattc actggccgtc gttttacaac gtcgtgactg ggaaaaccct ggcgttaccc   4531
```

```
aacttaatcg ccttgcagca catcccccctt tcgccagctg gcgtaatagc gaagaggccc    4591
gcaccgatcg cccttcccaa cagttgcgca gcctgaatgg cgaatgggac gcgccctgta    4651
gcggcgcatt aagcgcggcg ggtgtggtgg ttacgcgcag cgtgaccgct acacttgcca    4711 gcgcccctagc gcccgctcct ttcgctttct tcccttcctt tctcgccacg ttcgccggct    4771
ttccccgtca agctctaaat cggggggctcc ctttagggtt ccgatttagt gctttacggc    4831
acctcgaccc caaaaaactt gattagggtg atggttcacg tagtgggcca tcgccctgat    4891
agacggtttt tcgccctttg acgttggagt ccacgttctt taatagtgga ctcttgttcc    4951
aaactggaac aacactcaac cctatctcgg tctattcttt tgatttataa gggattttgc    5011
cgatttcggc ctattggtta aaaaatgagc tgatttaaca aaaatttaac gcgaatttta    5071
acaaaatatt aacgcttaca atttaggtgg cacttttcgg ggaaatgtgc gcggaaccccc    5131 tatttgttta ttttctaaa tacattcaaa tatgtatccg ctcatgagac aataaccctg    5191
```
ataaatgctt caataatatt gaaaaggaa gagt atg agt att caa cat ttc cgt    5246
                                     Met Ser Ile Gln His Phe Arg
                                     665                 670 gtc gcc ctt att ccc ttt ttt gcg gca ttt tgc ctt cct gtt ttt gct    5294
Val Ala Leu Ile Pro Phe Phe Ala Ala Phe Cys Leu Pro Val Phe Ala
            675                 680                 685 cac cca gaa acg ctg gtg aaa gta aaa gat gct gaa gat cag ttg ggt    5342
His Pro Glu Thr Leu Val Lys Val Lys Asp Ala Glu Asp Gln Leu Gly
        690                 695                 700 gca cga gtg ggt tac atc gaa ctg gat ctc aac agc ggt aag atc ctt    5390
Ala Arg Val Gly Tyr Ile Glu Leu Asp Leu Asn Ser Gly Lys Ile Leu
    705                 710                 715 gag agt ttt cgc ccc gaa gaa cgt ttt cca atg atg agc act ttt aaa    5438
Glu Ser Phe Arg Pro Glu Glu Arg Phe Pro Met Met Ser Thr Phe Lys
720                 725                 730                 735 gtt ctg cta tgt ggc gcg gta tta tcc cgt att gac gcc ggg caa gag    5486
Val Leu Leu Cys Gly Ala Val Leu Ser Arg Ile Asp Ala Gly Gln Glu
                740                 745                 750 caa ctc ggt cgc cgc ata cac tat tct cag aat gac ttg gtt gag tac    5534
Gln Leu Gly Arg Arg Ile His Tyr Ser Gln Asn Asp Leu Val Glu Tyr
            755                 760                 765 tca cca gtc aca gaa aag cat ctt acg gat ggc atg aca gta aga gaa    5582
Ser Pro Val Thr Glu Lys His Leu Thr Asp Gly Met Thr Val Arg Glu
        770                 775                 780 tta tgc agt gct gcc ata acc atg agt gat aac act gcg gcc aac tta    5630
Leu Cys Ser Ala Ala Ile Thr Met Ser Asp Asn Thr Ala Ala Asn Leu
    785                 790                 795 ctt ctg aca acg atc gga gga ccg aag gag cta acc gct ttt ttg cac    5678
Leu Leu Thr Thr Ile Gly Gly Pro Lys Glu Leu Thr Ala Phe Leu His
800                 805                 810                 815 aac atg ggg gat cat gta act cgc ctt gat cgt tgg gaa ccg gag ctg    5726
Asn Met Gly Asp His Val Thr Arg Leu Asp Arg Trp Glu Pro Glu Leu
                820                 825                 830 aat gaa gcc ata cca aac gac gag cgt gac acc acg atg cct gta gca    5774
Asn Glu Ala Ile Pro Asn Asp Glu Arg Asp Thr Thr Met Pro Val Ala
            835                 840                 845 atg gca aca acg ttg cgc aaa cta tta act ggc gaa cta ctt act cta    5822
Met Ala Thr Thr Leu Arg Lys Leu Leu Thr Gly Glu Leu Leu Thr Leu
        850                 855                 860 gct tcc cgg caa caa tta ata gac tgg atg gag gcg gat aaa gtt gca    5870
Ala Ser Arg Gln Gln Leu Ile Asp Trp Met Glu Ala Asp Lys Val Ala
    865                 870                 875

-continued

| | | | | | | | | | | | | | | | | |
|---|---|---|---|---|---|---|---|---|---|---|---|---|---|---|---|---|
| gga | cca | ctt | ctg | cgc | tcg | gcc | ctt | ccg | gct | ggc | tgg | ttt | att | gct | gat | 5918 |
| Gly | Pro | Leu | Leu | Arg | Ser | Ala | Leu | Pro | Ala | Gly | Trp | Phe | Ile | Ala | Asp | |
| 880 | | | | | 885 | | | | 890 | | | | | 895 | | |

| | | | | | | | | | | | | | | | | |
|---|---|---|---|---|---|---|---|---|---|---|---|---|---|---|---|---|
| aaa | tct | gga | gcc | ggt | gag | cgt | ggg | tct | cgc | ggt | atc | att | gca | gca | ctg | 5966 |
| Lys | Ser | Gly | Ala | Gly | Glu | Arg | Gly | Ser | Arg | Gly | Ile | Ile | Ala | Ala | Leu | |
| | | | | 900 | | | | | 905 | | | | | 910 | | |

| | | | | | | | | | | | | | | | | |
|---|---|---|---|---|---|---|---|---|---|---|---|---|---|---|---|---|
| ggg | cca | gat | ggt | aag | ccc | tcc | cgt | atc | gta | gtt | atc | tac | acg | acg | ggg | 6014 |
| Gly | Pro | Asp | Gly | Lys | Pro | Ser | Arg | Ile | Val | Val | Ile | Tyr | Thr | Thr | Gly | |
| | | | | 915 | | | | | 920 | | | | | 925 | | |

| | | | | | | | | | | | | | | | | |
|---|---|---|---|---|---|---|---|---|---|---|---|---|---|---|---|---|
| agt | cag | gca | act | atg | gat | gaa | cga | aat | aga | cag | atc | gct | gag | ata | ggt | 6062 |
| Ser | Gln | Ala | Thr | Met | Asp | Glu | Arg | Asn | Arg | Gln | Ile | Ala | Glu | Ile | Gly | |
| | | | | 930 | | | | | 935 | | | | | 940 | | |

| | | | | | | | | | |
|---|---|---|---|---|---|---|---|---|---|
| gcc | tca | ctg | att | aag | cat | tgg | taactgtcag | accaagttta | ctcatatata | 6113 |
| Ala | Ser | Leu | Ile | Lys | His | Trp | | | | |
| | 945 | | | | | 950 | | | | | ctttagattg atttaaaact tcattttta ttttaaagga tctaggtgaa gatccttttt 6173
gataatctca tgaccaaaat cccttaacgt gagttttcgt tccactgagc gtcagacccc 6233
gtagaaaaga tcaaggatc ttcttgagat cctttttttc tgcgcgtaat ctgctgcttg 6293
caaacaaaaa aaccaccgct accagcggtg tttgtttgc cggatcaaga gctaccaact 6353
ctttttccga aggtaactgg cttcagcaga gcgcagatac caaatactgt tcttctagtg 6413
tagccgtagt taggccacca cttcaagaac tctgtagcac cgcctacata cctcgctctg 6473
ctaatcctgt taccagtggc tgctgccagt ggcgataagt cgtgtcttac cgggttggac 6533
tcaagacgat agttaccgga taaggcgcag cggtcgggct gaacggggggt tcgtgcaca 6593
cagcccagct tggagcgaac gacctacacc gaactgagat acctacagcg tgagctatga 6653
gaaagcgcca cgcttcccga agggagaaag gcggacaggt atccggtaag cggcagggtc 6713
ggaacaggag agcgcacgag ggagcttcca gggggaaacg cctggtatct ttatagtcct 6773
gtcgggtttc gccacctctg acttgagcgt cgatttttgt gatgctcgtc aggggggcgg 6833
agcctatgga aaaacgccag caacgcggcc ttttttacggt tcctggcctt ttgctggcct 6893
tttgctcaca tgttctttcc tgcgttatcc cctgattctg tggataaccg tattaccgcc 6953
tttgagtgag ctgataccgc tcgccgcagc cgaacgaccg agcgcagcga gtcagtgagc 7013
gaggaagcgg aagagcgccc aatacgcaaa ccgcctctcc ccgcgcgttg gccgattcat 7073
taatgcagct ggcacgacag gtttcccgac tggaaagcgg gcagtgagcg caacgcaatt 7133
aatgtgagtt agctcactca ttaggcaccc caggctttac actttatgct tccggctcgt 7193
atgttgtgtg gaattgtgag cggataacaa tttcacacag gaaacagcta tgaccatgat 7253
tacgccagat ttaattaagg ccttaattag g 7284

<210> SEQ ID NO 12
<211> LENGTH: 120
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

```
Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
            115                 120

<210> SEQ ID NO 13
<211> LENGTH: 330
<212> TYPE: PRT
<213> ORGANISM: Artificial Sequence
<220> FEATURE:
<223> OTHER INFORMATION: Synthetic Construct

<400> SEQUENCE: 13

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 14
<211> LENGTH: 107
<212> TYPE: PRT
<213> ORGANISM: Artificial Sequence
<220> FEATURE:
<223> OTHER INFORMATION: Synthetic Construct

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: Synthetic Construct

<400> SEQUENCE: 15

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 16
<211> LENGTH: 286
<212> TYPE: PRT
<213> ORGANISM: Artificial Sequence
<220> FEATURE:
<223> OTHER INFORMATION: Synthetic Construct
```

<400> SEQUENCE: 16

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

<210> SEQ ID NO 17
<211> LENGTH: 4440
<212> TYPE: DNA
<213> ORGANISM: Artificial sequence
<220> FEATURE:
<223> OTHER INFORMATION: Engineered plasmid containing trastuzumab MAb
<220> FEATURE:
<221> NAME/KEY: sig_peptide
<222> LOCATION: (1254)..(1313)
<223> OTHER INFORMATION: IL2 signal sequence
<220> FEATURE:
<221> NAME/KEY: CDS
<222> LOCATION: (1314)..(1673)
<223> OTHER INFORMATION: Trastuzamab heavy variable
<220> FEATURE:
<221> NAME/KEY: CDS
<222> LOCATION: (1674)..(2660)
<223> OTHER INFORMATION: Trastuzamab heavy constant
<220> FEATURE:
<221> NAME/KEY: sig_peptide
<222> LOCATION: (2745)..(2804)
<223> OTHER INFORMATION: IL2 signal sequence
<220> FEATURE:
<221> NAME/KEY: CDS
<222> LOCATION: (2805)..(3110)
<223> OTHER INFORMATION: Trastuzamab light variable
<220> FEATURE:
<221> NAME/KEY: CDS
<222> LOCATION: (3111)..(3452)
<223> OTHER INFORMATION: Trastuzamab light constant (kappa)

<400> SEQUENCE: 17

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gccatgctct     180
aggaagatct tcaatattgg ccattagcca tattattcat tggttatata gcataaatca     240
atattggcta ttggccattg catacgttgt atctatatca taatatgtac atttatattg     300
gctcatgtcc aatatgaccg ccatgttggc attgattatt gactagttat taatagtaat     360
caattacggg gtcattagtt catagcccat atatggagtt ccgcgttaca taacttacgg     420
taaatggccc gcctggctga ccgcccaacg accccgccc attgacgtca ataatgacgt      480
atgttcccat agtaacgcca atagggactt tccattgacg tcaatgggtg gagtatttac     540
ggtaaactgc ccacttggca gtacatcaag tgtatcatat gccaagtccg cccctattg     600 acgtcaatga cggtaaatgg cccgcctggc attatgccca gtacatgacc ttacgggact     660
ttcctacttg gcagtacatc tacgtattag tcatcgctat taccatggtg atgcggtttt     720
ggcagtacac caatgggcgt ggatagcggt ttgactcacg gggatttcca agtctccacc     780
ccattgacgt caatgggagt ttgttttggc accaaaatca acgggacttt ccaaaatgtc     840
gtaataaccc cgccccgttg acgcaaatgg gcggtaggcg tgtacggtgg aggtctata      900 taagcagagc tcgtttagtg aaccgtcaga tcactagaag ctttattgcg gtagtttatc     960
acagttaaat tgctaacgca gtcagtgctt ctgacacaac agtctcgaac ttaagctgca    1020
gaagttggtc gtgaggcact gggcaggtaa gtatcaaggt tacaagacag gtttaaggag    1080
accaatagaa actgggcttg tcgagacaga gaagactctt gcgtttctga taggcaccta    1140
ttggtcttac tgacatccac tttgcctttc tctccacagg tgtccactcc cagttcaatt    1200
acagctctta aggctagagt acttaatacg actcactata ggctagaccc accatgtacc    1260
ggatgcagct gctgagctgt atcgccctgt ctctggccct cgtgaccaac agc gaa       1316
                                                                Glu
                                                                  1 gtg cag ctg gtg gaa agc ggc gga gga ctg gtg cag cct ggc gga tct       1364
Val Gln Leu Val Glu Ser Gly Gly Gly Leu Val Gln Pro Gly Gly Ser
      5                  10                  15 ctg aga ctg agc tgt gcc gcc agc ggc ttc aac atc aag gac acc tac       1412
Leu Arg Leu Ser Cys Ala Ala Ser Gly Phe Asn Ile Lys Asp Thr Tyr
         20                  25                  30 atc cac tgg gtg cgc cag gcc cct ggc aag gga ctg gaa tgg gtg gcc       1460
Ile His Trp Val Arg Gln Ala Pro Gly Lys Gly Leu Glu Trp Val Ala
     35                  40                  45 aga atc tac ccc acc aac ggc tac acc aga tac gcc gac agc gtg aag       1508
Arg Ile Tyr Pro Thr Asn Gly Tyr Thr Arg Tyr Ala Asp Ser Val Lys
 50                  55                  60                  65 ggc cgg ttc acc atc agc gcc gac acc agc aag aac acc gcc tac ctg       1556
Gly Arg Phe Thr Ile Ser Ala Asp Thr Ser Lys Asn Thr Ala Tyr Leu
             70                  75                  80
```

```
cag atg aac agc ctg cgg gcc gag gac acc gcc gtg tac tac tgt agt    1604
Gln Met Asn Ser Leu Arg Ala Glu Asp Thr Ala Val Tyr Tyr Cys Ser
         85                  90                  95 aga tgg gga ggc gac ggc ttc tac gcc atg gac tat tgg ggc cag ggc    1652
Arg Trp Gly Gly Asp Gly Phe Tyr Ala Met Asp Tyr Trp Gly Gln Gly
            100                 105                 110 acc ctc gtg aca gtg tct agt gcg tcg acc aag gga cct tcg gtc ttc    1700
Thr Leu Val Thr Val Ser Ser Ala Ser Thr Lys Gly Pro Ser Val Phe
        115                 120                 125 ccc ctg gca ccc tcc tcc aag agc acc tct ggg ggc aca gcg gcc ctg    1748
Pro Leu Ala Pro Ser Ser Lys Ser Thr Ser Gly Gly Thr Ala Ala Leu
130                 135                 140                 145 ggc tgc ctg gtc aag gac tac ttc ccc gaa ccg gtg acg gtg tcg tgg    1796
Gly Cys Leu Val Lys Asp Tyr Phe Pro Glu Pro Val Thr Val Ser Trp
                150                 155                 160 aac tca ggc gcc ctg acc agc ggc gtg cac acc ttc ccg gct gtc cta    1844
Asn Ser Gly Ala Leu Thr Ser Gly Val His Thr Phe Pro Ala Val Leu
            165                 170                 175 cag tcc tca gga ctc tac tcc ctc agc agc gtg gtg acc gtg ccc tcc    1892
Gln Ser Ser Gly Leu Tyr Ser Leu Ser Ser Val Val Thr Val Pro Ser
        180                 185                 190 agc agc ttg ggc acc cag acc tac atc tgc aac gtg aat cac aag ccc    1940
Ser Ser Leu Gly Thr Gln Thr Tyr Ile Cys Asn Val Asn His Lys Pro
195                 200                 205 agc aac acc aag gtg gac aag aaa gtt gaa cca aag agc tgc gac aag    1988
Ser Asn Thr Lys Val Asp Lys Lys Val Glu Pro Lys Ser Cys Asp Lys
210                 215                 220                 225 acc cac acg tgt ccc ccc tgc cct gcc cct gaa ctg ctg gga ggc ccc    2036
Thr His Thr Cys Pro Pro Cys Pro Ala Pro Glu Leu Leu Gly Gly Pro
                230                 235                 240 agc gtg ttc ctg ttc ccc cca aag ccc aag gac acc ctg atg atc agc    2084
Ser Val Phe Leu Phe Pro Pro Lys Pro Lys Asp Thr Leu Met Ile Ser
            245                 250                 255 cgg acc ccc gaa gtg acc tgc gtg gtg gtg gac gtg tcc cac gag gac    2132
Arg Thr Pro Glu Val Thr Cys Val Val Val Asp Val Ser His Glu Asp
        260                 265                 270 cct gaa gtg aag ttt aat tgg tac gtg gac ggc gtg gaa gtg cac aac    2180
Pro Glu Val Lys Phe Asn Trp Tyr Val Asp Gly Val Glu Val His Asn
275                 280                 285 gcc aag acc aag ccc aga gag gaa cag tac aac agc acc tac cgg gtg    2228
Ala Lys Thr Lys Pro Arg Glu Glu Gln Tyr Asn Ser Thr Tyr Arg Val
290                 295                 300                 305 gtg tcc gtg ctg acc gtg ctg cac cag gac tgg ctg aac ggc aaa gag    2276
Val Ser Val Leu Thr Val Leu His Gln Asp Trp Leu Asn Gly Lys Glu
                310                 315                 320 tac aag tgc aag gtg tcc aac aag gcc ctg cct gcc ccc atc gag aaa    2324
Tyr Lys Cys Lys Val Ser Asn Lys Ala Leu Pro Ala Pro Ile Glu Lys
            325                 330                 335 acc atc agc aag gcc aag ggc cag ccc cgc gag cct cag gtc tac aca    2372
Thr Ile Ser Lys Ala Lys Gly Gln Pro Arg Glu Pro Gln Val Tyr Thr
        340                 345                 350 ctg ccc ccc agc cgg gaa gag atg acc aag aac cag gtg tcc ctg acc    2420
Leu Pro Pro Ser Arg Glu Glu Met Thr Lys Asn Gln Val Ser Leu Thr
355                 360                 365 tgc ctg gtc aag ggc ttc tac ccc agc gac atc gcc gtg gaa tgg gag    2468
Cys Leu Val Lys Gly Phe Tyr Pro Ser Asp Ile Ala Val Glu Trp Glu
370                 375                 380                 385 agc aac ggc cag ccc gag aac aac tac aag acc acc ccc cct gtg ctg    2516
Ser Asn Gly Gln Pro Glu Asn Asn Tyr Lys Thr Thr Pro Pro Val Leu
                390                 395                 400
```

| | |
|---|---|
| gac agc gac ggc tca ttc ttc ctg tat agc aag ctg acc gtg gac aag<br>Asp Ser Asp Gly Ser Phe Phe Leu Tyr Ser Lys Leu Thr Val Asp Lys<br>405 410 415 | 2564 |
| agc cgg tgg cag cag ggc aac gtg ttc agc tgc agc gtg atg cac gag<br>Ser Arg Trp Gln Gln Gly Asn Val Phe Ser Cys Ser Val Met His Glu<br>420 425 430 | 2612 |
| gcc ctg cac aac cac tac acc cag aag tcc ctg agc ctg agc ccc ggc<br>Ala Leu His Asn His Tyr Thr Gln Lys Ser Leu Ser Leu Ser Pro Gly<br>435 440 445 | 2660 |
| agaaagcgga gagccccgt gaagcagacc ctgaacttcg acctgctgaa gctggccggc | 2720 |
| gacgtggaaa gcaaccctgg ccctatgtac agaatgcagc tgctgctgct gatcgccctg | 2780 |
| agcctggccc tggtgaccaa cagc gat atc cag atg acc cag agc ccc agc<br>Asp Ile Gln Met Thr Gln Ser Pro Ser<br>450 455 | 2831 |
| agc ctg tct gcc agc gtg ggc gac aga gtg acc atc acc tgt aga gcc<br>Ser Leu Ser Ala Ser Val Gly Asp Arg Val Thr Ile Thr Cys Arg Ala<br>460 465 470 | 2879 |
| agc cag gac gtg aac acc gcc gtg gcc tgg tat cag cag aag cct ggc<br>Ser Gln Asp Val Asn Thr Ala Val Ala Trp Tyr Gln Gln Lys Pro Gly<br>475 480 485 490 | 2927 |
| aag gcc ccc aag ctg ctg atc tac agc gcc agc ttc ctg tac agc ggc<br>Lys Ala Pro Lys Leu Leu Ile Tyr Ser Ala Ser Phe Leu Tyr Ser Gly<br>495 500 505 | 2975 |
| gtg ccc agc aga ttc agc ggc agc aga tcc ggc acc gac ttc acc ctg<br>Val Pro Ser Arg Phe Ser Gly Ser Arg Ser Gly Thr Asp Phe Thr Leu<br>510 515 520 | 3023 |
| acc atc agc tcc ctg cag ccc gag gac ttc gcc acc tac tac tgc cag<br>Thr Ile Ser Ser Leu Gln Pro Glu Asp Phe Ala Thr Tyr Tyr Cys Gln<br>525 530 535 | 3071 |
| cag cac tac acc acc ccc cca aca ttt ggc cag ggc acc aag gtg gaa<br>Gln His Tyr Thr Thr Pro Pro Thr Phe Gly Gln Gly Thr Lys Val Glu<br>540 545 550 | 3119 |
| atc aag cgt acg gtg gcc gcc cca agc gtg ttc atc ttc cca cca agc<br>Ile Lys Arg Thr Val Ala Ala Pro Ser Val Phe Ile Phe Pro Pro Ser<br>555 560 565 570 | 3167 |
| gat gag cag ctg aag agc gga acc gcc agc gtg gtg tgc ctg ctg aac<br>Asp Glu Gln Leu Lys Ser Gly Thr Ala Ser Val Val Cys Leu Leu Asn<br>575 580 585 | 3215 |
| aac ttc tac cca cgg gag gcc aag gtg cag tgg aag gtg gat aac gcc<br>Asn Phe Tyr Pro Arg Glu Ala Lys Val Gln Trp Lys Val Asp Asn Ala<br>590 595 600 | 3263 |
| ctg cag agc gga aac agc cag gag agc gtg acc gag cag gat agc aag<br>Leu Gln Ser Gly Asn Ser Gln Glu Ser Val Thr Glu Gln Asp Ser Lys<br>605 610 615 | 3311 |
| gat agc acc tac agc ctg agc agc acc ctg acc ctg agc aag gcc gat<br>Asp Ser Thr Tyr Ser Leu Ser Ser Thr Leu Thr Leu Ser Lys Ala Asp<br>620 625 630 | 3359 |
| tac gag aag cac aag gtg tac gcc tgc gag gtg acc cac cag gga ctg<br>Tyr Glu Lys His Lys Val Tyr Ala Cys Glu Val Thr His Gln Gly Leu<br>635 640 645 650 | 3407 |
| agc agc cca gtg acc aag agc ttc aac cgc gga gag tgc tga taa<br>Ser Ser Pro Val Thr Lys Ser Phe Asn Arg Gly Glu Cys<br>655 660 | 3452 |
| agcggccgct tcgagcagac atgataagat acattgatga gtttggacaa accacaacta | 3512 |
| gaatgcagtg aaaaaaatgc tttatttgtg aaatttgtga tgctattgct ttatttgtaa | 3572 |
| ccattataag ctgcaataaa caagttaaca acaacaattg cattcatttt atgtttcagg | 3632 |
| ttcaggggga gatgtgggag gttttttaaa gcaagtaaaa cctctacaaa tgtggtaaaa | 3692 |

```
tcgataagga tcttcctaga gcatggctac gtagataagt agcatggcgg gttaatcatt    3752
aactacaagg aaccctagt gatggagttg gccactccct ctctgcgcgc tcgctcgctc     3812
actgaggccg ggcgaccaaa ggtcgcccga cgcccgggct ttgcccgggc ggcctcagtg    3872
agcgagcgag cgcgcagcct taattaacct aattcactgg ccgtcgtttt acaacgtcgt    3932
gactgggaaa accctggcgt tacccaactt aatcgccttg cagcacatcc ccctttcgcc    3992
agctggcgta atagcgaaga ggcccgcacc gatcgccctt cccaacagtt gcgcagcctg    4052
aatggcgaat gggacgcgcc ctgtagcggc gcattaagcg cggcgggtgt ggtggttacg    4112
cgcagcgtga ccgctacact tgccagcgcc ctagcgcccg ctcctttcgc tttcttccct    4172
tcctttctcg ccacgttcgc cggctttccc cgtcaagctc taaatcgggg gctcccttta    4232
gggttccgat ttagtgcttt acggcacctc gaccccaaaa aacttgatta gggtgatggt    4292
tcacgtagtg ggccatcgcc ctgatagacg ttttttcgcc ctttgacgtt ggagtccacg    4352
ttctttaata gtggactctt gttccaaact ggaacaacac tcaaccctat ctcggtctat    4412
tcttttgatt tataagggat tttgccga                                       4440
```

<210> SEQ ID NO 18
<211> LENGTH: 120
<212> TYPE: PRT
<213> ORGANISM: Artificial sequence
<220> FEATURE:
<223> OTHER INFORMATION: Synthetic Construct

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 19
<211> LENGTH: 329
<212> TYPE: PRT
<213> ORGANISM: Artificial sequence
<220> FEATURE:
<223> OTHER INFORMATION: Synthetic Construct

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 20
<211> LENGTH: 102
<212> TYPE: PRT
<213> ORGANISM: Artificial sequence
<220> FEATURE:
<223> OTHER INFORMATION: Synthetic Construct

<400> SEQUENCE: 20

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80
```

```
Glu Asp Phe Ala Thr Tyr Tyr Cys Gln Gln His Tyr Thr Thr Pro Pro
                85                  90                  95

Thr Phe Gly Gln Gly Thr
            100

<210> SEQ ID NO 21
<211> LENGTH: 112
<212> TYPE: PRT
<213> ORGANISM: Artificial sequence
<220> FEATURE:
<223> OTHER INFORMATION: Synthetic Construct

<400> SEQUENCE: 21

Lys Val Glu Ile Lys Arg Thr Val Ala Ala Pro Ser Val Phe Ile Phe
1               5                   10                  15

Pro Pro Ser Asp Glu Gln Leu Lys Ser Gly Thr Ala Ser Val Val Cys
            20                  25                  30

Leu Leu Asn Asn Phe Tyr Pro Arg Glu Ala Lys Val Gln Trp Lys Val
        35                  40                  45

Asp Asn Ala Leu Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 22
<211> LENGTH: 12
<212> TYPE: PRT
<213> ORGANISM: Artificial sequence
<220> FEATURE:
<223> OTHER INFORMATION: Peptide mimotope of HER2 epitope

<400> SEQUENCE: 22

Leu Leu Gly Pro Tyr Glu Leu Trp Glu Leu Ser His
1               5                   10

<210> SEQ ID NO 23
<211> LENGTH: 689
<212> TYPE: PRT
<213> ORGANISM: Artificial sequence
<220> FEATURE:
<223> OTHER INFORMATION: trastuzumab immunoglobulin H435A mutant

<400> SEQUENCE: 23

Gly Ala Gly Cys Cys Ala Ala Ala Thr Cys Thr Thr Gly Thr Gly
1               5                   10                  15

Ala Cys Ala Ala Ala Ala Cys Thr Cys Ala Cys Ala Cys Ala Thr Gly
            20                  25                  30

Cys Cys Cys Ala Cys Cys Gly Thr Gly Cys Cys Cys Ala Gly Cys Ala
        35                  40                  45

Cys Cys Thr Gly Ala Ala Cys Thr Cys Cys Thr Gly Gly Gly Gly Gly
    50                  55                  60

Gly Ala Cys Cys Gly Thr Cys Ala Gly Thr Cys Thr Thr Cys Cys Thr
65                  70                  75                  80

Cys Thr Thr Cys Cys Cys Cys Cys Cys Ala Ala Ala Ala Cys Cys Cys
                85                  90                  95
```

-continued

```
Ala Ala Gly Gly Ala Cys Ala Cys Cys Thr Cys Ala Thr Gly Ala
            100                 105                 110
Thr Cys Thr Cys Cys Cys Gly Gly Ala Cys Cys Cys Thr Gly Ala
            115                 120                 125
Gly Gly Thr Cys Ala Cys Ala Thr Gly Cys Gly Thr Gly Thr Gly
            130                 135                 140
Gly Thr Gly Gly Ala Cys Gly Thr Ala Gly Cys Ala Cys Gly
145                 150                 155                 160
Ala Ala Gly Ala Cys Cys Thr Gly Ala Gly Thr Cys Ala Ala
            165                 170                 175
Gly Thr Thr Cys Ala Ala Cys Thr Gly Gly Thr Ala Cys Gly Thr Gly
            180                 185                 190
Gly Ala Cys Gly Gly Cys Gly Thr Gly Gly Ala Gly Gly Thr Gly Cys
            195                 200                 205
Ala Thr Ala Ala Thr Gly Cys Cys Ala Ala Gly Ala Cys Ala Ala
            210                 215                 220
Gly Cys Cys Gly Cys Gly Gly Ala Gly Gly Ala Gly Cys Ala Gly
225                 230                 235                 240
Thr Ala Cys Ala Ala Cys Ala Gly Cys Ala Cys Gly Thr Ala Cys Cys
            245                 250                 255
Gly Thr Gly Thr Gly Gly Thr Cys Ala Gly Cys Gly Thr Cys Cys Thr
            260                 265                 270
Cys Ala Cys Cys Gly Thr Cys Thr Gly Cys Ala Cys Cys Ala Gly
            275                 280                 285
Gly Ala Cys Thr Gly Gly Cys Thr Gly Ala Ala Thr Gly Gly Cys Ala
            290                 295                 300
Ala Gly Gly Ala Gly Thr Ala Cys Ala Ala Gly Thr Gly Cys Ala Ala
305                 310                 315                 320
Gly Gly Thr Cys Thr Cys Cys Ala Ala Cys Ala Ala Ala Gly Cys Cys
            325                 330                 335
Cys Thr Cys Cys Cys Ala Gly Cys Cys Cys Cys Ala Thr Cys Gly
            340                 345                 350
Ala Gly Ala Ala Ala Ala Cys Cys Ala Thr Cys Thr Cys Cys Ala Ala
            355                 360                 365
Ala Gly Cys Cys Ala Ala Ala Gly Gly Gly Cys Ala Gly Cys Cys Cys
            370                 375                 380
Cys Gly Ala Gly Ala Ala Cys Cys Ala Cys Ala Gly Gly Thr Gly Thr
385                 390                 395                 400
Ala Cys Ala Cys Cys Cys Thr Gly Cys Cys Cys Cys Cys Ala Thr Cys
            405                 410                 415
Cys Cys Gly Gly Gly Ala Thr Gly Ala Gly Cys Thr Gly Ala Cys Cys
            420                 425                 430
Ala Ala Gly Ala Ala Cys Cys Ala Gly Gly Thr Cys Ala Gly Cys Cys
            435                 440                 445
Thr Gly Ala Cys Cys Thr Gly Cys Cys Thr Gly Gly Thr Cys Ala Ala
            450                 455                 460
Ala Gly Gly Cys Thr Thr Cys Thr Ala Thr Cys Cys Cys Ala Gly Cys
465                 470                 475                 480
Gly Ala Cys Ala Thr Cys Gly Cys Cys Gly Thr Gly Gly Ala Gly Thr
            485                 490                 495
Gly Gly Gly Ala Gly Ala Gly Cys Ala Ala Thr Gly Gly Gly Cys Ala
            500                 505                 510
```

```
Gly Cys Cys Gly Gly Ala Gly Ala Ala Cys Ala Ala Cys Thr Ala Cys
            515                 520                 525
Ala Ala Gly Ala Cys Cys Ala Cys Gly Cys Cys Thr Cys Cys Cys Gly
        530                 535                 540
Thr Gly Cys Thr Gly Gly Ala Cys Thr Cys Cys Gly Ala Cys Gly Gly
545                 550                 555                 560
Cys Thr Cys Cys Thr Thr Cys Thr Thr Cys Cys Thr Cys Thr Ala Cys
                565                 570                 575
Ala Gly Cys Ala Ala Gly Cys Thr Cys Ala Cys Cys Gly Thr Gly Gly
            580                 585                 590
Ala Cys Ala Ala Gly Ala Gly Cys Ala Gly Gly Thr Gly Gly Cys Ala
        595                 600                 605
Gly Cys Ala Gly Gly Gly Gly Ala Ala Cys Gly Thr Cys Thr Thr Cys
    610                 615                 620
Thr Cys Ala Thr Gly Cys Thr Cys Cys Gly Thr Gly Ala Thr Gly Cys
625                 630                 635                 640
Ala Thr Gly Ala Gly Gly Cys Thr Cys Thr Gly Cys Ala Cys Ala Ala
                645                 650                 655
Cys Gly Cys Cys Thr Ala Cys Ala Cys Gly Cys Ala Gly Ala Ala Gly
            660                 665                 670
Ala Gly Cys Cys Thr Cys Thr Cys Cys Cys Thr Gly Thr Cys Thr Cys
        675                 680                 685
Cys

<210> SEQ ID NO 24
<211> LENGTH: 689
<212> TYPE: DNA
<213> ORGANISM: Artificial sequence
<220> FEATURE:
<223> OTHER INFORMATION: immunoglobulin fragment with I253A mutant

<400> SEQUENCE: 24
gagcccaaat cttgtgacaa aactcacaca tgcccaccgt gcccagcacc tgaactcctg      60
gggggaccgt cagtcttcct cttccccccca aacccaagg acaccctcat ggcctcccgg    120
accctgagg  tcacatgcgt ggtggtggac gtgagccacg aagaccctga ggtcaagttc    180
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagccctcc cagcccccat cgagaaaacc    360
atctccaaag ccaagggcca gccccgagaa ccacaggtgt acaccctgcc cccatcccgg    420
gatgagctga ccaagaacca ggtcagcctg acctgcctgg tcaaaggctt ctatcccagc    480
gacatcgccg tggagtggga gagcaatggg cagccggaga acaactacaa gaccacgcct    540
cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga gagcctctc cctgtctcc                                       689

<210> SEQ ID NO 25
<211> LENGTH: 469
<212> TYPE: PRT
<213> ORGANISM: Artificial Sequence
<220> FEATURE:
<223> OTHER INFORMATION: Trastruzumab heavy chain
```

```
<400> SEQUENCE: 25

Met Tyr Arg Met Gln Leu Leu Ser Cys Ile Ala Leu Ser Leu Ala Leu
1               5                   10                  15

Val Thr Asn Ser Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415
```

```
Thr Pro Pro Val Leu Asp Ser Asp Gly Ser Phe Phe Leu Tyr Ser Lys
            420             425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly
465
```